US006562616B1

United States Patent
Toner et al.

(10) Patent No.: US 6,562,616 B1
(45) Date of Patent: May 13, 2003

(54) METHODS AND DEVICES FOR CELL CULTURING AND ORGAN ASSIST SYSTEMS

(75) Inventors: Mehmet Toner, Wellesley, MA (US); Martin L. Yarmush, Newton, MA (US); Ulysses J. Balis, Peabody, MA (US); Arno W. Tilles, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/599,297

(22) Filed: Jun. 21, 2000

Related U.S. Application Data

(60) Provisional application No. 60/140,125, filed on Jun. 21, 1999.

(51) Int. Cl.[7] .............................................. C12M 3/04
(52) U.S. Cl. ............................... 435/293.1; 435/293.2; 435/297.2; 435/370; 435/395; 604/5.04
(58) Field of Search ................................. 435/370, 395, 435/399, 401, 289.1, 402, 297.2, 297.4, 284.1, 293.1, 293.2; 604/5.04

(56) References Cited

U.S. PATENT DOCUMENTS

| | | | | |
|---|---|---|---|---|
| 4,937,196 A | * | 6/1990 | Wrasidlo et al. | 435/297.2 |
| 5,190,878 A | * | 3/1993 | Wilhelm | 435/297.2 |
| 5,270,192 A | * | 12/1993 | Li et al. | 435/174 |
| 5,459,069 A | * | 10/1995 | Palsson et al. | 435/289.1 |
| 5,605,835 A | * | 2/1997 | Hu et al. | 435/297.2 |
| 5,658,797 A | * | 8/1997 | Bader | 435/284.1 |

FOREIGN PATENT DOCUMENTS

| | | |
|---|---|---|
| WO | WO-96/34087 A1 * | 10/1996 |
| WO | WO 00/56870 | 9/2000 |

OTHER PUBLICATIONS

Smith MD, et al., "Development and characterization of a hybrid artificial liver bioreactor with integral membrane oxygenation," In: Bioartificial Liver Support Systems. The Critical Issues, Crepaldi G, Demetriou AA, Muraca M, Eds. 1997 Rome: CIC Edizioni Internazionali, pp. 27–35.

* cited by examiner

*Primary Examiner*—William H. Beisner
(74) *Attorney, Agent, or Firm*—Fish & Richardson P.C.

(57) ABSTRACT

The invention relates to new flow-through cell culturing devices that include plates arranged in parallel and spaced to control the flow patterns and velocity of liquid medium flowing between the plates. The devices can also include gas-permeable, liquid impermeable membranes arranged between the plates. The devices can be used to culture cells, such as hepatocytes, at high levels of mass transport of nutrients, oxygen, and waste products, yet low levels of shear stress for extended periods of time and with high levels of cell function, e.g., in organ assist systems. The invention also includes new culturing plates for use in the devices, and methods of manufacturing these plates.

42 Claims, 28 Drawing Sheets

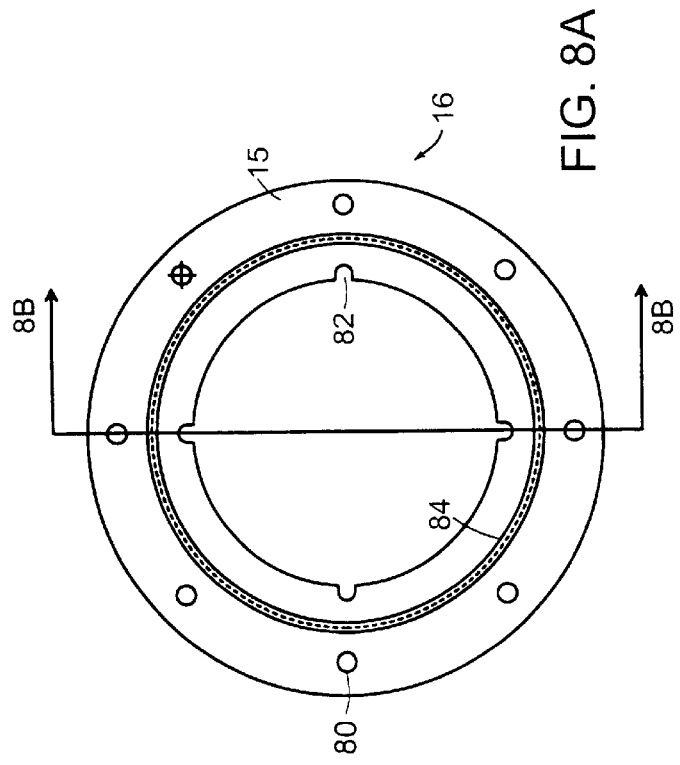
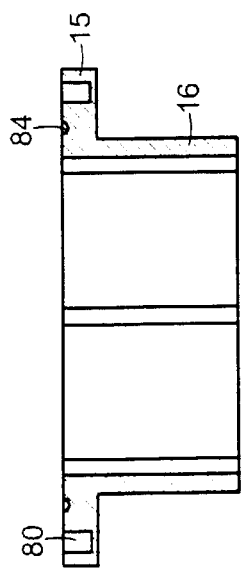
FIG. 8A
FIG. 8B

METHODS AND DEVICES FOR CELL CULTURING AND ORGAN ASSIST SYSTEMS

CROSS REFERENCE TO RELATED APPLICATIONS

This application claims priority from U.S. Provisional Application No. 60/140,125, filed Jun. 21, 1999. The content of this application is incorporated herein by reference in its entirety.

FIELD OF THE INVENTION

The invention relates to cell culturing methods and devices, and their use in organ, e.g., liver, assist systems, and methods of making and using such devices.

BACKGROUND OF THE INVENTION

Approximately 30,000 Americans die each year from liver diseases. Although liver transplantation has a survival rate in excess of 65%, many prospective recipients die while awaiting a donor. Attempts to develop extracorporeal devices and systems for liver replacement, such as microcarriers and hollow-fiber bioreactors, have shown only limited success. Some of these liver assist devices (LAD) have also been referred to as extracorporeal bioartificial livers (BAL). See, e.g., Uchino et al., ASAIO Transactions, 34(4): 972–977 (1988); Taguchi et al., Artificial Organs, 20(2): 178–185 (1996); Hu et al., U.S. Pat. No. 5,605,835; and Kelly, U.S. Pat. No. 5,290,684.

A BAL is an extracorporeal device used to replace liver function on a temporary basis. One embodiment of a BAL utilizes planar-configured cultures of one or more cell types. A BAL can support patients awaiting transplantation and can be used to stabilize patients during periods of recovery from fulminant hepatic failure.

SUMMARY OF THE INVENTION

The invention is based on the discovery that if the flow patterns and velocity of the liquid medium flowing between the plates in a flow-through cell culturing device are carefully controlled, the device can be used to culture cells at high levels of mass transport of nutrients, oxygen, and waste products, yet low levels of shear stress, which can limit cell survival and function. The invention is further based on the discovery that oxygenation of the cells can be further enhanced by separating the flow of culture medium and gas by a gas-permeable, liquid-impermeable membrane, thereby enabling low media flow rates to provide low shear stress, and high gas flow rates to provide a high level of oxygen to the cells.

Oxygen is delivered to cells by an oxygenated fluid. An oxygenated fluid can be gases or liquids and can include pure oxygen gas, air, oxygen-enriched air, and liquids that can be highly oxygenated.

The new flow-through cell culturing devices can thus be used to culture hepatocytes and fibroblasts for extended periods of time and with high levels of cell function in organ assist systems, such as hepatic function in liver assist systems.

The invention also includes new culturing plates for use in the flow-through culturing devices, and methods of manufacturing these plates.

In general, the invention features a flow-through cell culturing device including a housing with an inlet and an outlet; a first plate arranged within the housing; and a second plate arranged within the housing substantially in parallel with the first plate to create a chamber therebetween having a height of between about 25 and 500 microns, e.g., 50 to 100, 200, or 400 microns, wherein the chamber has a fluid entry and a fluid exit positioned such that fluid entering the housing through the inlet flows through the fluid entry of the chamber, flows through the chamber, exits the chamber through the fluid exit, and flows out of the housing through the outlet. The device can also include one or more cells, e.g., cultured, preserved (e.g., cryopreserved or dried), or freshly isolated hepatocytes or other cells, seeded onto a plate.

The device can further include a first manifold controlling the flow of liquid from the housing inlet directly to the fluid entry of the chamber; and a second manifold controlling the flow of liquid from the fluid exit of the chamber to the housing outlet. In this device, each plate can include a hole which serves as a fluid entry for the chamber below the plate, and as a second fluid exit from the chamber above the plate. The device can include any number of plates, all arranged within the housing in parallel, stacked one on top of the other.

Each plate in the device can be associated with at least three spacer elements located at three points in a plane on the plate, wherein all spacer elements have the same height. The plates can be made of, e.g., glass, polymethylmethacrylate, or polycarbonate. The spacer elements can be formed from the same or different material as the plates. For example, the spacer elements can be polymethylmethacrylate (PMMA), UV-cured acrylate adhesives, visible light curable adhesives, or polyurethane.

In another aspect, the invention features a flow-through cell culturing device including a housing with an inlet and an outlet; a first plate arranged within the housing; a second plate arranged within the housing substantially in parallel with the first plate to create a chamber therebetween; and a gas-permeable, liquid-impermeable membrane arranged between the first and second plates to create first and second compartments within the chamber, the first compartment having a height of about 5 microns to 5.0 millimeters, and the second compartment having a height of between about 25 and 500 microns, e.g., 50 to 100 or 200 microns, wherein the first compartment has a gas entry and a gas exit, and the second compartment has a fluid entry and a fluid exit positioned such that fluid entering the housing through the inlet flows through the fluid entry of the second compartment, flows through the second compartment, exits the second compartment through the fluid exit, and flows out of the housing through the outlet, and wherein the first compartment and the second compartment are not in fluid communication. The device can include one or more cells seeded onto the plate.

The gas-permeable, liquid-impermeable membrane can comprise polyurethane, polyolefin, polyethylene, polypropylene, polyvinylidene fluoride, polystyrene, nylon, silicone rubber, or mixtures or copolymers thereof. The device can include a substrate to support the membrane. The device can include additional plates and membranes arranged in a stack of alternating plates and membranes.

In another aspect, the invention features a method of microfabricating one or more uniform spacer elements on a plate, by depositing one or more separate volumes of a liquid polymer on a surface of the plate; curing the polymer to form one or more solid spacer elements; and machining the solid spacer elements to obtain a uniform height for each spacer element relative to the plate surface. The liquid polymer can be cured by exposure to UV light, air, or a catalyst. The spacer elements can be machined to a uniform height of between 10 and 200 microns, e.g, 50 microns. The liquid polymer can be, e.g., acrylate, siloxane, polyurethane, or epoxy resin.

The invention also features a method of microfabricating one or more uniform spacer elements on a plate by impressing a probe, e.g., a heated probe, into the surface of the plate with a sufficient force to form one or more microindentations with concomitant one or more micro-elevations; and machining the micro-elevations to obtain a uniform height for each micro-elevation relative to the plate surface, thereby forming the uniform spacer elements. The machining can include compressing top edges of the micro-elevations to obtain a uniform height for each micro-elevation relative to the plate surface, or removing top edges of the micro-elevations to obtain a uniform height for each micro-elevation relative to the plate surface.

In another aspect, the invention features an organ, e.g., liver, assist system including one or more of the new flow-through cell culturing devices described herein, a first conduit for conducting plasma from a patient to the housing inlet; a second conduit for conducting plasma from the cell culturing device to the patient; and a pump for moving plasma through the conduits and cell culturing device. The system can further include a plasma separator to remove blood cells from whole blood to provide plasma that is passed through the cell culturing device, and/or a bubble trap, to remove bubbles from the plasma in the first conduit prior to entering the cell culturing device.

The invention also includes a method of filtering a bodily fluid, e.g., blood or blood plasma, by seeding a cell culturing device as described herein with hepatocytes and/or fibroblasts or other cells; introducing the bodily fluid into the inlet of the device; and allowing the bodily fluid to flow through the device and exit through the outlet, thereby filtering the bodily fluid. The device can be seeded with 2 to 25 billion hepatocytes, e.g., porcine, human, bovine, ovine, equine, or murine hepatocytes. The bodily fluid can be introduced into the inlet at a flow rate of 0.05 to 400 ml/minute. The bodily fluid can be passed through a filter prior to introducing the bodily fluid into the inlet of the device.

In another embodiment, the invention features a modular device including a plurality of units, a fluid inlet conduit, and a fluid outlet conduit. Each unit includes a plate and a gas-permeable, liquid-impermeable membrane, e.g., with a substrate, arranged substantially in parallel with the plate and connected to the plate by an exterior wall to create a chamber therebetween having a height of between about 25 and 500 microns, wherein the chamber has a fluid entry connected to the fluid inlet conduit (e.g., via a valve) and a fluid exit connected to the fluid outlet conduit and positioned such that fluid entering the chamber flows through the chamber, exits the chamber through the fluid exit, and flows out of the modular device through the outlet. This modular device can be enclosed in a sealed container having a gas entry and gas exit.

The "dead volume" of a given device or system is the total liquid volume of the device including all fluid conduits and pumps that are part of the extracorporeal system. There is a limitation in this dead volume in a liver assist system. A large dead volume would cause dilution of the desired compounds produced by the hepatocytes within the liver assist system. The bioactivity of these compounds relies on a minimal critical concentration; therefore, dilution would compromise device performance.

When two plates are substantially in parallel, the plates have a distance between them that varies less than 20 percent from one end of the plates to the other. When two plates have a uniform distance between them, the distance does not vary by more than 10 percent from one end of the plates to the other.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The new flow-through cell culturing devices and liver assist systems provide numerous advantages. The new devices allow various cells to be cultured with high levels of mass transport and oxygenation while avoiding detrimental shear stress normally associated with high levels of mass transport. As a result, even shear-sensitive cells such as hepatocytes can be cultured for extended periods of time at high levels of function. This allows the new flow-through cell culturing devices to be used in organ, e.g., liver, assist systems.

In addition, the new cell culturing devices have an extremely small dead volume, which is important in organ assist systems, because it minimizes the amount of plasma or blood that is outside the body at any time, and also reduces dilutional effects.

The new methods of manufacturing the plates in the cell culturing devices are simple and economical, yet highly precise to provide the necessary control over flow patterns and dead volume in the new devices. Moreover, the new microindented spacers introduce no additional material to the biocompatible culture plates, and thus are inherently biocompatible.

Other features and advantages of the invention will be apparent from the following detailed description, and from the claims.

BRIEF DESCRIPTION OF THE DRAWINGS

FIG. 8A is a top plan schematic view of the housing of a cylindrical cell culturing device.

FIG. 8B is a schematic side cross-sectional view of the device housing of FIG. 8A, along section line 8B—8B.

DETAILED DESCRIPTION

The new flow-through cell culturing devices (also known as "bioreactors") are designed to carefully control the flow patterns and velocity of the liquid media flowing between the plates, and thus over the cells adhered to the plates, and to reduce the dead volume of the devices to a minimum. The new devices provide maximum mass transport and oxygenation while avoiding shear stress that can damage cells or inhibit cell growth and metabolism, e.g., function. Thus, the new flow-through cell culturing devices can be used to culture even delicate, anchorage-dependent cells such as hepatocytes for extended periods of time and with high levels of function, e.g., hepatic function, in organ assist systems.

Regardless of configuration, the new devices all embody several general design parameters and contain plates with spacers that can be made using new microfabrication methods, all described in further detail below. One embodiment, also described in further detail below, is a cylindrical device, but rectangular, serpentine, and other configurations are possible.

General Design Parameters of Cell Culturing Devices

The new flow-through cell culturing devices or bioreactors have at least the following three specific design features:

(1) the devices must guarantee an efficient mass transport to a large number of cells in a small volume;

(2) the devices must avoid exposing the cells, such as hepatocytes and fibroblasts, to deleterious flow conditions such as high shear stress and pressure drop; and (3) the devices must be suitable to culture large numbers of cells for extended periods of time, and at high levels of cell function, for example, hepatocytes must thrive and exhibit high levels of hepatic function.

Figure 1A:
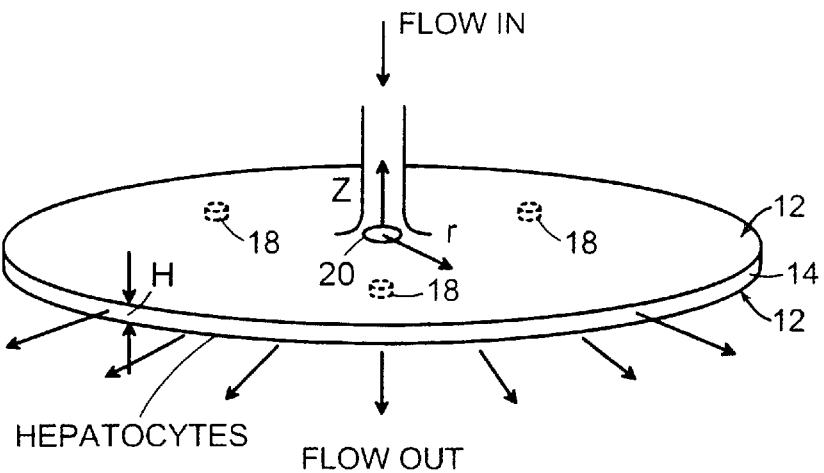
FIG. 1A is a schematic diagram of two plates of a new flow-through, single-compartment cell culturing device arranged in parallel to form a chamber with a height H.

These three design parameters are met by flow-through cell culturing devices shown in FIGS. 1A, 1B, 2A to 2C, and 3. A common feature of all of the new culturing devices is a series of plates 12, on which the cells are cultured, which are aligned in parallel within a housing or jacket 16 to form the culturing device. As shown in FIG. 1A, adjacent plates 12, are arranged in parallel to form a chamber 14, between the pair of plates, with a height H, determined by the height of one or more precisely machined spacer elements 18 located between each pair of plates. This height H is between 5.0 and 500 microns or more, e.g., 5, 50, 80, 100, 150, 200, or 400 microns, and is maintained uniformly, e.g., plus or minus 10 percent, or better, e.g., 5, 3, 2, or even 1 percent, throughout the entire surface area of the two plates.

Figure 2A:
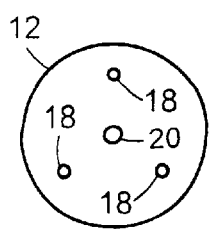
FIGS. 2A to 2C are schematic bottom plan views of various spacer element configurations on plates used in the culturing devices.
Figure 2B:
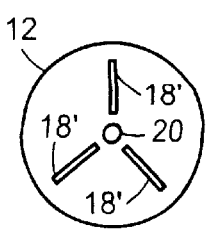
Figure 2C:
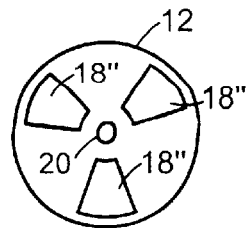

The spacer elements 18 also can have many configurations. For example, as shown in FIG. 2A, plate 12 can include at least three small, individual, circular spacer elements 18 located at three points in a plane on one surface of the plate on which the adjacent plate can rest to create the chamber. Other spacer element shapes are possible, as are different numbers and locations of spacers. Alternatively, the spacer elements can be ribs 18' extending radially from the center of each plate as shown in FIG. 2B. In another embodiment, the spacer elements can be pie-shaped 18", as shown in FIG. 2C.

Other spacer element shapes and configurations can be used. The common feature is that the spacer elements must be of a uniform height of from 5 to 500 microns, e.g., 25 to 200 microns or 50 to 100 microns, so the adjacent plates form a chamber of a uniform height throughout. In addition, the spacer elements should be shaped and located to take as little space as possible on the plates, and to provide adequate support for adjacent plates.

The plates, including the attached spacer elements are arranged in parallel as shown in FIG. 3 (in which the individual spacer elements are not shown for the sake of clarity). Cell culturing device 10 has a housing 16 in which plates 12 are stacked in "sandwich" fashion. Each plate has spacer elements on its bottom (or top) surface, so the plates are automatically set with the proper spacing when stacked in this manner, creating a chamber between each adjacent pair of plates having a uniform height H. The top plate 12', forms the bottom of the first chamber 14', and the bottom plate 12" forms the top of the last chamber 14". In this configuration n plates form n+1 chambers, i.e., twenty plates form twenty-one chambers, but only 20 chambers (on top of each plate) are seeded with cells. Other configurations are possible so that n plates can form n or n−1 chambers.

Figure 10A:
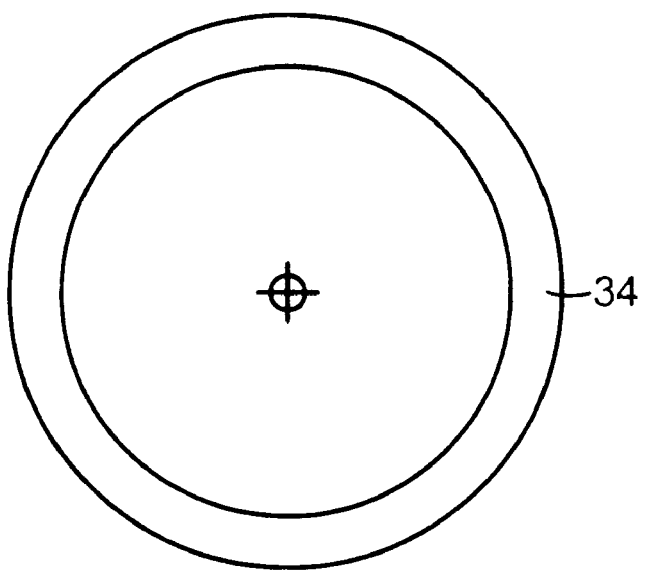
FIG. 10A is a top plan schematic view of a bottom of a cylindrical cell culturing device.

Device 10 includes a top cover 30 with an inlet 32, and a bottom 34 with an outlet 36 (see FIG. 10A). Cover 30 attaches to flange 15 of housing 16. In addition, the device can include a top manifold plate 38 (which includes spacer elements on its bottom surface), that is arranged on top of the top plate 12', and directs liquid entering inlet 32 through hole 39 in the top manifold plate, and thus into the first chamber 14'. The device can also include a bottom manifold plate 40 which does not have a central hole, and that is arranged beneath the bottom plate 12". This prevents liquid from flowing through hole 20 in plate 12" from directly through outlet 36, and instead passes through the last chamber 14" and then out through outlet 36.

Figure 9A:
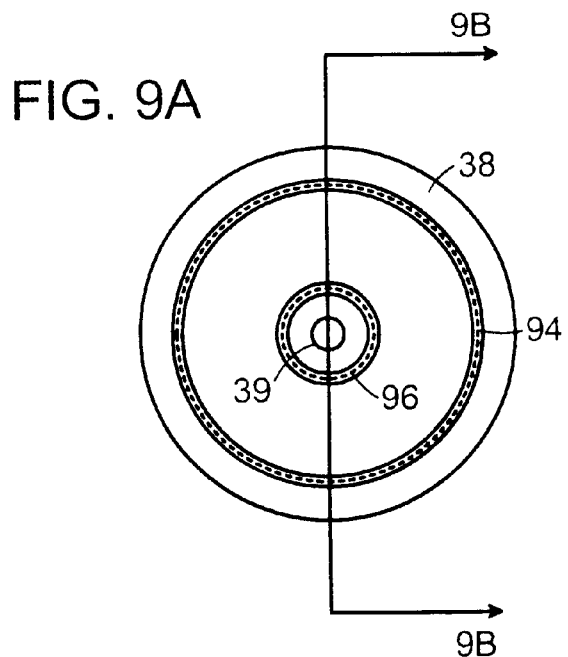
FIG. 9A is a top plan schematic view of a top manifold plate of a cylindrical cell culturing device.

As shown in FIGS. 3 and 9A, liquid media, e.g., culture media, plasma, or whole blood, flows into hole 39 in top manifold plate 38 (the fluid entry to chamber 14'), and flows through hole 20 in the adjacent top plate 12', as well as between the plates (in first chamber 14') and out at the edges of the plates (the fluid exit of the chamber). In the circular plates shown in FIGS. 1A and 3, the flow is in a radially outwardly direction from the central hole 20 to the periphery of the plates. In other embodiments, the hole can be located at one edge of the plate, and the flow would be lateral between the plates from one side to another.

Figure 4:
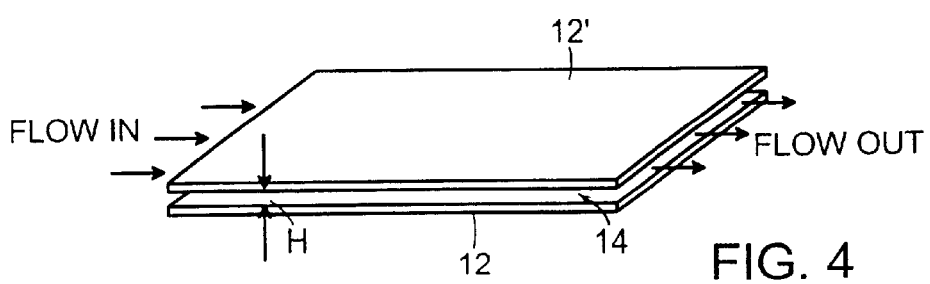
FIG. 4 is a schematic diagram of a rectangular embodiment of the two plates shown in FIG. 1A.

In addition, plates can be made in other shapes, for example, rectangular. In such embodiments, a hole can be located in the center, at an edge, or can be absent. A hole is not required if the medium is directed from one edge of a chamber 14 (the fluid entry) to the opposite edge (the fluid exit) between two rectangular plates 12, as shown in FIG. 4.

In a flow-through cell culturing device, every pair of adjacent plates creates a chamber, and the medium flows through each chamber. Thus, a portion of the medium flows through each hole 20 in each plate 12, to reach the next chamber, and a portion of the medium flows through each chamber 14 and out at the edge of the plates and down in space 17, along the wall of the housing 16, to the bottom of the housing and out through outlet 36. Once a portion of the medium flows through a chamber, it does not pass through another chamber, or through the same chamber again.

The space 17 between the stack of plates 12 and the housing 16 is carefully controlled to minimize the dead volume. This space is limited to about 500 microns or less, e.g., 50, 100, 250, 300, or 400 microns. This space can be maintained by inserting ribs or rods between the outer edges of the plates and the inner surface of the housing. These ribs or rods, e.g., of a hard, biocompatible plastic such as an acetal homopolymer resin like DELRIN® stainless steel, polysulfone, and polycarbonate, can be partially recessed in niches (82 in FIG. 8A) machined into the inside of the wall of the housing 16. It is also possible to cast the outer jacket 16 with the appropriate spacers in place using injection/molding techniques.

To ensure that adequate medium flows through each chamber, and not merely through the holes 20, the size of the holes in the plates (or the size of the space between the housing and the plates if no holes are used) i.e., the size of the fluid entry of each chamber, can be controlled, so that the hole in the top plate 12' is smaller than the hole in the bottom plate 12". The holes in the remaining plates are made gradually larger from top to bottom, forming an imaginary Venturi cone of holes. This Venturi system can be modeled using the parameters described herein and known numerical models of jet engine Venturi intake air manifolds.

The parameters described herein, e.g., of plate size and spacing, can be varied, as long as they scale to biological parameters encountered in vivo. For example, one can also vary chamber height (i.e., chamber 14' height smaller than chamber 14") to ensure uniform flow through each chamber.

Figure 1B:
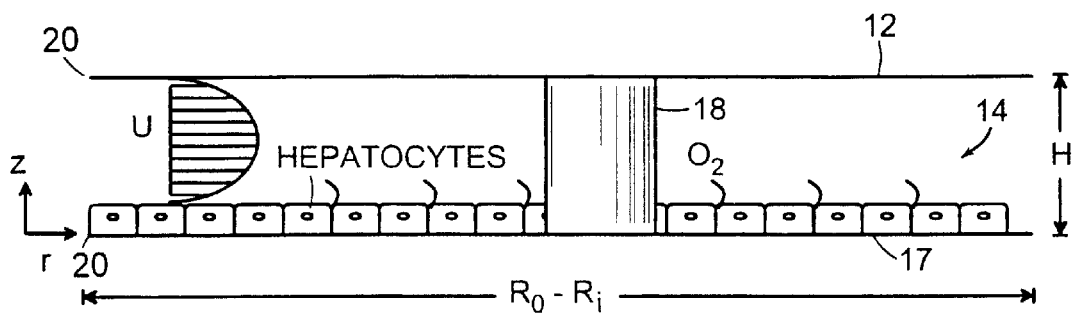
FIG. 1B is an enlarged side view of one half of the two plates of FIG. 1A.
Figure 1C:
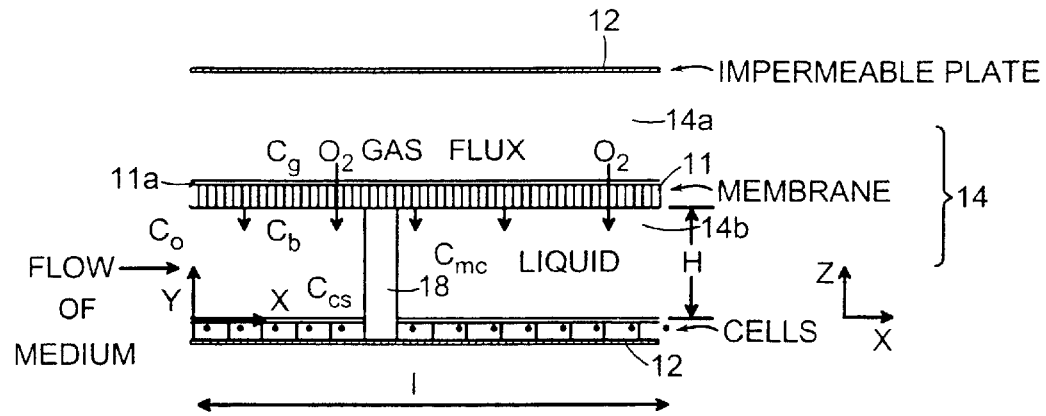
FIG. 1C is a schematic diagram of two plates of a new flow-through, two-compartment cell culturing device arranged in parallel to form a medium chamber with a height H.

A fourth design parameter is also important for optimum cell culturing conditions. To ensure a high level of oxygenation of the cells, while avoiding undesirable shear stress, the flow of medium should be separated from the flow of oxygen-containing gas, such as air. This separation of flows can be accomplished by inserting a gas-permeable, liquid-impermeable membrane 11 into chamber 14, as illustrated in FIG. 1C. Chamber 14 is thus separated into a gas compartment 14a and a medium compartment 14b to create a two-compartment bioreactor. Oxygenated gas can flow through the gas compartment 14a in the same or different directions compared to the flow of medium in medium compartment 14b. For example, flow can be in opposite directions, in the same direction, or at angles, e.g., perpendicular flow.

The gas-permeable membrane will typically require a support substrate 11a, such as a plastic or wire mesh, or a thin, perforated substrate made of metal or plastic. This support should be selected to have little or no effect on the transport, e.g., by diffusion, of oxygen from the gas compartment 14a through membrane 11. Alternatively, the membrane can be supported by multiple spacer elements that are set closely enough together to provide adequate support for the membrane, yet far enough apart that they will not significantly inhibit oxygen transport through the membrane. Spacer elements can be created using the new methods described herein.

As discussed in further detail below, fabricating a bioreactor having the new two-compartment configuration with an internal oxygen-permeable membrane significantly increases oxygen delivery to the cells compared to the single-compartment configuration. With decreasing flow rates, the oxygen delivery improvement over performance of the single-compartment reactor becomes increasingly marked. This two-compartment bioreactor design also benefits from the carefully controlled hydrodynamic height, H, of the medium compartment 14b, which is maintained at 50 to 500 microns, e.g., 80 to 200 microns. The height of the gas compartment 14a is less critical, and can be anywhere from 50 to 500 microns to several millimeters. Thus, overall oxygen maximal flux can geometrically increase with reducing height. The powerful combination of design elements in this bioreactor design enables surface-wide delivery of adequate oxygen to all cells, under a wide range of flow rates.

Methods of Manufacturing Cell Culturing Plates

The main component of the new cell culturing devices is the culturing plate, although the housing and manifold plates are also important in achieving the desired flow control, low shear stress, and low dead volume. Each device contains a number of plates, at least two, but typically more, for example, 10, 20, or even 100 or more plates, stacked one on top of the other. The total number of plates determine the total surface area available for cells. All plates in a given device have the same configuration, unless the holes, if present, are made of different sizes as described above.

The key to providing uniform, microspaced chambers between the plates is to have uniform spacer elements. These spacer elements are located between the plates, e.g., on the bottom or top of each plate, and can be manufactured using two new methods, microdeposition and microindentation, each with optional micromachining.

Plates

The plates can be circular or rectangular, or other shapes, and can be made from any solid, biocompatible, and preferably inert material to which mammalian and other cells can adhere, either directly or via a binding agent or cell matrix ligand such as extracellular matrix molecules, such as collagen (e.g., Type I), laminin, or fibronectin, or fragments of binding sites of extracellular matrix proteins, such as RGD sequence. Suitable materials for the plates include glass, ceramic, and plastics such as polymethylmethacrylate (PMMA), polycarbonate (e.g., LEXAN®), polystyrene, polyethylene teraphthalate, polyvinyl chloride (PVC), cPVC, fluorocarbon resins such as TEFLON®, and DELRIN®.

The plates can be anywhere from 0.1 to 2.0 mm thick, e.g., 1.0 mm, and can have a surface area of from 1 to 1000 $cm^2$. The optimal size of the plates depends upon the total number of cells to be cultured, and the total number of plates in a given cell culturing device.

The plates can be smooth or rough, to provide a surface to which cells can adhere. For example, the plate surface can include microgrooves about 10 to 100 microns in depth. The microgrooves can have various cross-sections, including rectangular, semicircular, or V-shaped.

Each plate can include one or more holes to allow liquid medium to flow from one chamber to the next, or can be manufactured without a hole, if the medium is directed to flow from one edge of a plate to the opposite edge. The presence or absence of a hole is dependent on the nature of the housing in which the plates are stacked.

Each plate includes one or more spacer elements, which can be created as a part of the material of each plate, or can be made of a separate material fixed to the plate. The spacer elements must be positioned on either the top or bottom surface of the plate to give a precise resting position for the adjacent plate when the plates are stacked. Thus, if the spacer elements are in the form of small circular elements, there should be at least three such elements, located in a plane on the plate surface, e.g., at the points of a triangle. Of course, more elements (e.g., 4, 5, 6, or 8) can be used to provide added support and structural strength for the plate stack.

Elongate ribs can be arranged in numerous configurations, e.g., in spoke-like fashion on a round plate, or in parallel on a square or a round plate. Ribs in the form of arcs can also be used if placed so as to provide a secure support for the adjacent plate, e.g., around the periphery of a circle.

The ribs can also be designed and located to direct the flow of the liquid medium as it passes through the flow-through cell culturing device at higher flow rates. However, the paramount goal is uniformity of flow coverage throughout the device.

The spacer elements can be initially all of the same height, or can have generally the same height and then be micromachined to a uniform height after being secured to the plate.

Microdeposited Spacer Elements

If spacer elements are made of a separate material and then attached to the plates, they can be made of a liquid polymer (e.g., polycarbonates, acrylates, e.g., DYMAX™ Corp. LIGHT WELD® series UV curable acrylate adhesives, visible light curable adhesives, or polyurethane) that is microdeposited onto the plates, e.g., with a microcapillary or micronozzle capable of delivering a controlled volume of polymer, to form spots or ribs that are between 5 or 10 and 100 microns in height. These spots or ribs are then cured (e.g., by UV light, air, or a catalyst) to become rigid and to adhere to the plate. All spacer elements on one plate can be deposited at the same time if the microcapillaries or micronozzles are arranged in a group that operates simultaneously.

Alternatively, the liquid polymer can be microdeposited by injection molding. In this method, a liquid polymer is injected into a mold of a spot or rib, or a whole series of spots or ribs, placed onto the top or bottom surface of a plate. After injection molding, the polymer is cured in the mold, and the mold is removed.

In another method, tiny, solid spacer elements can be attached to the surface of the plates by, e.g., adhesives, ultrasonic welding, or chemical solvents.

After the polymer spots or ribs are securely attached to the plate, and if necessary, solidified, they are typically micromachined to a uniform height. This can be accomplished using standard equipment, such as milling machines and surface grinders. Precision is ensured by using an accurate measurement device, such as a linear vertical micrometer. All of the spacer elements on a plate must be machined to a uniform height; however, if the individual spacers and any adhesive or other material used to fix them to the plate are already of a uniform height, then no micromachining is required.

Microindented Spacer Elements

The spacer elements can also be created directly on the bottom (or top) surface of the plate by microindentation. In this method, the spacer elements are made by using a probe of known geometry, and impressing the probe into the surface of the plate using a known force to create an indentation or crater with a concomitant raised annular spacing ring, in the surface of the plate. Probes can be made of any hard substance, for example, diamond, sapphire, or carbide. By using a known force and the same probe, or probes, a highly precise and repeatable set of craters can be generated in multiple plates. Plates for this method are made of plastics such as PMMA, glass, and other plate materials described herein, that can be indented with the probe, preferably at ambient temperatures, but also with a heated probe, or with a heated plate, or both.

Figure 6A:
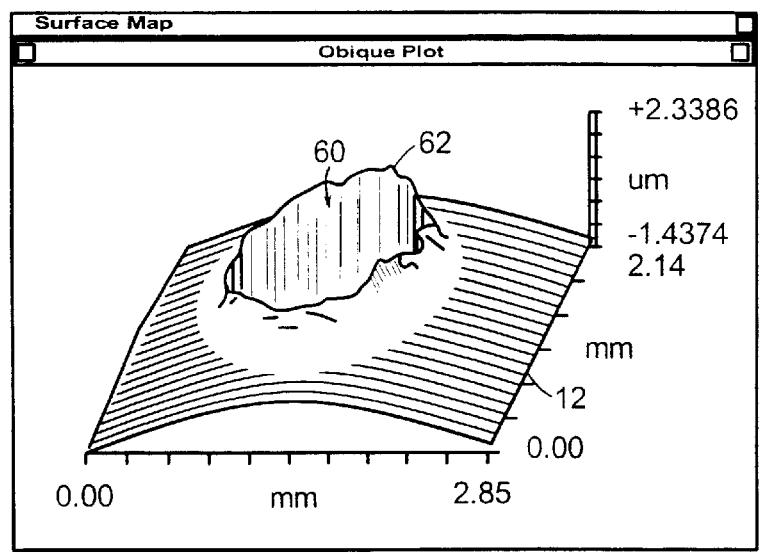
FIGS. 6A and 6B are computer generated and schematic diagrams, respectively, of one embodiment of a spacer element, the so-called "microindented" spacer element.
Figure 6B:
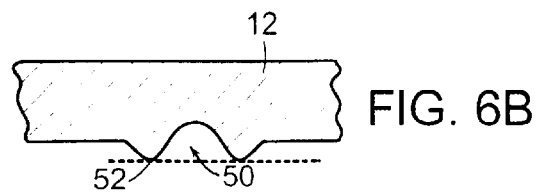

As shown in FIG. 6A, each crater 50 has a concomitant annular spacing ring 52 that is generated and forms the spacer element. As shown in FIG. 6A, these spacing rings may be somewhat jagged or variable, but can be simply compressed or flattened to a uniform height, or can be micromachined to the same height to achieve a uniform spacer element having a height H as shown in FIG. 6B.

The nature and height of the spacing ring can be determined by the shape and size of the probe, as well as the force applied to the probe. For example, the probe can be conical (e.g., with a conical slope of no more than 45 degrees) or spherical, and can be about 2 microns in size, or less, to create a spacer ring of 10 microns, 50 microns, or 100 microns in elevation. Typical forces required to create the craters and the annular spacing rings in PMMA plates follow a nonlinear transfer function.

The probe or probes, e.g., one for each indentation on a plate, are attached securely to a device that controls probe motion. This device then impresses the probes into the plate, preferably all at once, each with the same force, so that a number of identical, or essentially identical, craters are formed. The annular spacer rings that are formed simultaneously with the craters are then crushed or micromachined, e.g., with a surface-scoring carbon dioxide laser, to achieve a uniform height for all the spacer elements on a given plate, and for all the plates in a culturing device.

Although round craters are simple to prepare and create an effective spacer element, other configurations are possible. For example, dual elevated ribs formed on either side of an elongated indentation can be prepared using an elongate probe, such as a micro-chisel. Series of these dual ribs can be arranged on a plate in the same way as the solid, single ribs shown in FIGS. 2B and 2C.

The microindentation method provides several benefits. First, all the spacer elements on a given plate can be generated at the same time. Second, the method is very simple, and highly repeatable, and thus ideal for mass production. Third, the method introduces no additional materials to the plate, which avoids any possible incompatibility associated with added materials. In addition, the method can be used with many diverse materials.

Two-Compartment Bioreactors

There is a need to stabilize the gas permeable membrane by mechanical supports on the gas compartment side or on the liquid (cell) compartment side, or both. Several design alternatives can be used. For example, the top solid surface can be molded from a polymer (e.g., polysulfone, polystyrene, polycarbonate) which includes spacer elements to separate the membrane physically from the top solid surface and avoid collapse of the membrane resulting from pressure on the liquid side. Spacer elements can also be etched onto glass substrates, or spacers of woven nylon or metal mesh can be included in the gas compartment. The bottom solid surface can also include microspacers to support the membrane. Again, these structures can be molded into a plastic substrate or etched into glass, or created by other manufacturing processes, e.g., those described herein. It is also possible to match the location of all or some of the spacer elements in both the gas and liquid compartments to squeeze the membrane between two solid supports and physically prevent the large deformations of the membrane.

If the new microspacing techniques described herein are used, the result will be a controlled number of uniform spacer elements on the plates that support the gas-permeable, liquid-impermeable membranes. The resulting spacer elements provide a uniform height for the medium compartment 14b of chamber 14 created between plates. Each chamber 14 can be created with its own top and bottom plate, or chamber 14 can be formed by alternating plates with gas-permeable membranes.

Thus, different types of plates can be prepared. A first type of plate has spacer elements 18 on one side, and two plates are used to create each chamber, with the spacer elements facing each other, and sandwiching a membrane 11 between them as shown in FIG. 3B. The second kind of plate 12 has spacer elements 18 on both sides, and is used to assemble a bioreactor in which the plates are alternated with membranes 11 as shown in FIG. 3C.

Figure 3A:
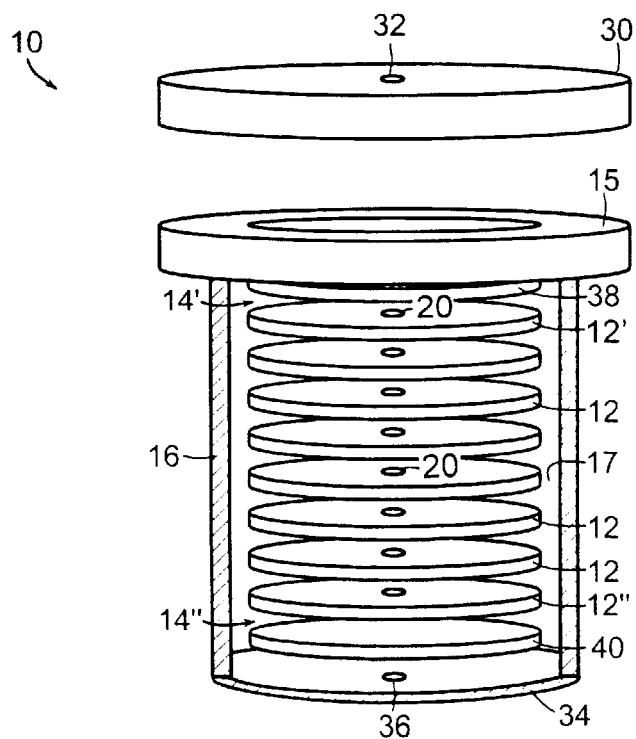
FIG. 3A is a schematic diagram of a cylindrical flow-through, single-compartment cell culturing device.
Figure 3B:
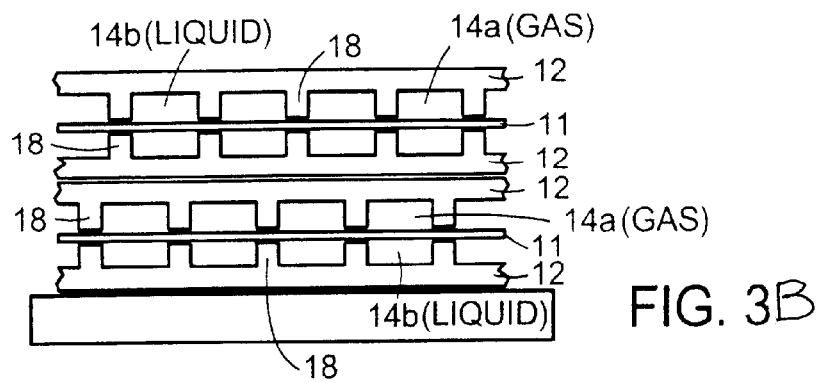
FIG. 3B is a schematic diagram of a flow-through, two-compartment cell culturing device.
Figure 3C:
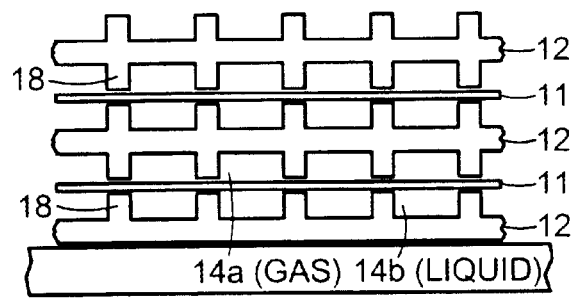
FIG. 3C is a schematic diagram of an alternative flow-through, two-compartment cell culturing device.
Figure 3D:
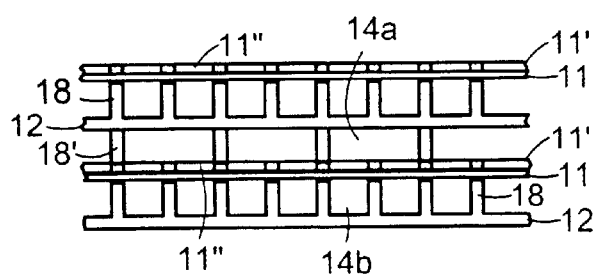
FIG. 3D is a schematic diagram of a flow-through, two-compartment cell culturing device including a perforated top plate and a common gas compartment.

Alternatively, as shown in FIG. 3D, each unit or cartridge can include a bottom (or top) plate 12 with spacer elements 18, a gas-permeable membrane 11, and a perforated metal or plastic plate 11' (with perforations 11") that is secured to the membrane, e.g., with an adhesive. In this embodiment, no top (or bottom) plate is required for the individual units, and all units are open to one, common gas compartment. The units are stacked on top of each other, and are spaced apart (by spacers 18') so that gas can enter between the units.

Figure 3E:
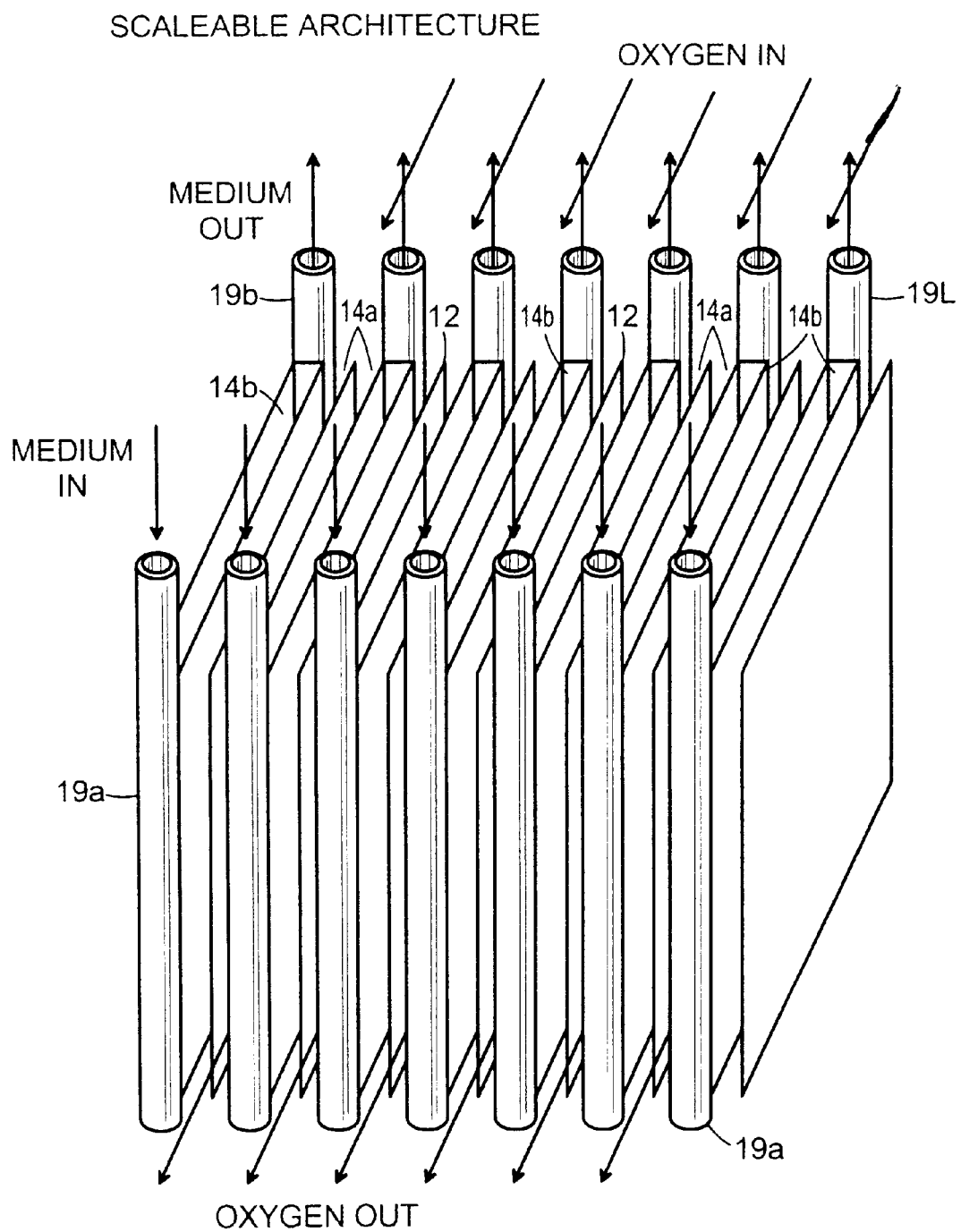
FIG. 3E is a schematic diagram of a flow-through, two-compartment cell culturing device including conduits to direct liquid medium into and out of individual units.

In another embodiment, shown in FIG. 3E, gas compartments 14a are located on either side of a solid plate 12, and liquid compartments 14b are arranged on either side of the two adjacent gas compartments. The liquid compartments are bounded by fluid entries and fluid exits 19a and 19b, which transport the liquid medium into and out of the liquid compartment, respectively. Gas can surround each of the units, e.g., in one, common gas space. Each of the units in this device can be removed, e.g., the device is a modular device wherein individual units can be added or removed as desired. For example, the fluid entries and fluid exits of each unit may be attached to a single conduit or manifold having multiple inlets and outlets for each of the units. The entries and exits of each unit can connect to an individual inlet and outlet by means of connecting valves. In one example, the connecting valves are designed so that they can be connected or disconnected without disturbing the functioning of the device, e.g., the flow of liquid in the device. This modular device permits a unit, e.g., a unit containing damaged or nonfunctional cells, to be removed without affecting the function of the device as mediated by the remainder of the units. In addition, the modular device permits additional units to be added to the device to increase the number of functioning cells in the device.

The plates in the two-compartment bioreactors are paired with gas-permeable, liquid-impermeable membranes. For example, a polyurethane gas permeable membrane (Breathe-Easy, Diversified Biotech, Boston, Mass.), having one side covered with an adhesive surface, can be used. The membrane is in planar, flat sheet configuration and extends in a plane to separate the cell compartment and the gas compartment. The membrane is gas-permeable to allow transport of oxygen from the gas compartment to the cells and from the cells to the gas compartment. The membrane must be impermeable to liquid but permeable to gas in the range from about 1 mL/m$^2$/day to about 10 L/m$^2$/day. The membrane must also be able to be sterilized, resistant to puncture, ripping, wrinkling, and handling during manufacture of the bioreactor device.

Membrane materials suitable for use in the invention include single layer and multi-laminate composites of non-porous or microporous materials such as polyolefin; polyethylene, such as TYVEK®, particularly TYVEK® 1073B, a microporous polyethylene (obtained from 3M; having mean pore size of 1.7 μm); polypropylene; polyvinylidene fluoride; Pall hydrophobic-treated nylon; inorganic polymers, such as silicone rubber and microporous inorganic polymers; a three-layered co-extruded film of styrene-butadiene-styrene/ethyl vinyl acetate/styrene-butadiene-styrene (SBS/EVA/SBS); and a two-layered co-extruded film of styrene-butadiene-styrene/polyethylene (SBS/PE). Hydrophobic films including silicone rubber (silastic), polyethylene, chloride polymers, and the like can also be used. Other materials for gas permeable membranes, including ceramic-based and metal sintered, rigid membranes, can also be used as long as they are biocompatible and not toxic to cells.

Membrane materials having the following characteristics are suitable for use in the invention: permeable to oxygen, hydrophobic (i.e., at least partially impermeable to water in the absence of large pressure drops across the material), non-cytotoxic to cells on at least one side (such that the attachment and function of the cells is not limited by the material), and non-degrading in the presence of gas and aqueous solutions. Membrane materials having these characteristics can be easily obtained commercially or prepared using standard techniques.

Each unit is formed of one gas and one liquid compartment separated by a membrane and stacked to achieve the appropriate cell mass. Each unit may have a separate inlet/outlet manifold for both the fluid and gas. The inlet (or outlet) to each cartridge may be from a larger distributing manifold that is connected to the main flow circuit. This will enable access to individual cartridge while the system is under operation. Alternatively, a gas compartment may be pooled to a one single compartment with one inlet-outlet which then flows in between each individual liquid compartments which includes a top gas permeable membrane.

In case the blood is preferred to be perfused through the reactor or direct exposure of hepatocytes to flow is not desirable, cells (xenogeneic or allogeneic) can be separated from direct contact with blood by a liquid permeable membrane, including, but not limited to hydrophilic films, cellulose, and the like.

Cell Culturing and Liver Assist Systems

In use, the new cell culturing devices or bioreactors are an integral part of a cell culturing system, or a liver (or other organ) assist system. For cell culturing, cells, such as hepatocytes, and other cells such as fibroblasts, Kupffer (macrophage-like cells), Ito (fat) cells, biliary ductal cells, endothelial cells, and a variety of associated stromal cells, are seeded onto the plates, and the system is filled with a culture medium that is circulated through the device to deliver nutrients to the cells and carry off waste products. The cells can be seeded onto the plates in the cell culturing devices and used immediately, or cryopreserved or lyophilized for storage prior to use.

For an organ assist system, organ cells, such hepatocytes, e.g., human, porcine, bovine, rabbit, or rat hepatocytes, or a combination of hepatocytes and fibroblasts, or other organ cells such as pancreas cells and kidney cells are seeded onto the plates in the device, and the device is connected to a patient in need of blood purification. The blood plasma of the patient is slowly circulated through the cell culturing device to allow the hepatocytes to provide a high level of hepatic function, thereby purifying the blood.

Figure 5A:
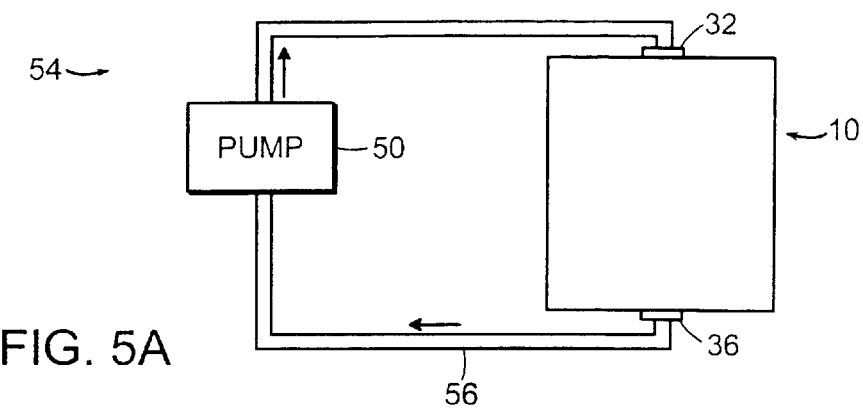
FIG. 5A is a schematic diagram of a flow-through cell culturing device used in a cell culturing system.

As shown in FIG. 5A, a cell culturing system 54 includes a flow-through cell culturing device 10, and fluid conduits 52 and 56 that connect device inlet 32 and device outlet 36, respectively, to a pump 50 that circulates culture medium through device 10. Oxygen and other nutrients are added continuously or periodically, for example into reservoirs within pump 50. Similarly, waste products and desired products secreted by the cells are collected and processed in the pump or are collected in a separate, standard filter mechanism located upstream of the pump and connected to conduit 56.

Figure 5B:
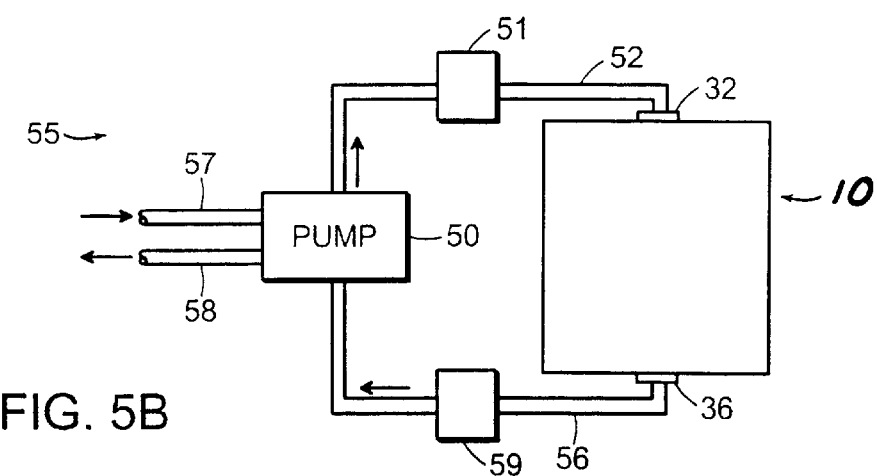
FIG. 5B is a schematic diagram of a flow-through cell culturing device used in a liver assist system.

As shown in FIG. 5B, a liver assist system 55 works in much the same way as a cell culturing system, except that additional fluid conduits 57, 58 connect the system to a patient in need of liver assistance. Blood plasma is separated from a patient's blood in a plasma separator (not shown) and is directed into pump 50 through conduit 57. The plasma is optionally passed through a charcoal filter (not shown), and a bubble filter or trap 51 (to remove air bubbles that could become lodged in the chambers), and is then directed into cell culturing device 10 through conduit 52. A bubble trap can also be used in a cell culturing device. The bubble trap can be a standard device with a mechanical action, or could disperse bubbles using a surfactant (e.g., a polaxamer) to reduce surface tension of the medium.

Once the plasma has passed through the cell culturing device 10, conduit 56 directs the plasma to an optional, but useful, filter 59, which removes waste products, especially cells detached from the device 10 fragments of lysed cells. Any filter designed for use with blood can be used. The purified and filtered plasma is then directed back to pump 50, e.g., via an optional temperature regulator and oxygenator (not shown) which provides a physiologic environment for the cells and the plasma, and is returned to the patient via conduit 58, which leads to the plasma separator (not shown) that recombines the patient's blood cells with the plasma, and directs the whole blood back into the patient. Standard blood handling devices, filters, and conduits can be used in conjunction with the new flow-through cell culturing devices.

The new liver assist systems can be used in the same manner as other known liver assist devices, but the new systems have a much lower dead volume, and thus remove a much smaller fraction of a patient's blood from the body at any given time. However, the new systems provide much higher levels of hepatic function because the hepatocytes thrive and function at a higher level in the new cell culturing devices. To further reduce the total dead volume of the system, which includes the cell culturing device dead volume and the circuit dead volume (e.g., the volume of all pumps, conduits, and other apparatus), the diameter of the conduits, and the size of the pumps, etc. should be kept to a minimum.

For example, for a system suitable for human use, the total dead volume of the cell culturing device should be 250 to 2000 ml, and the circuit dead volume should be about 250 to 500 ml for the extracorporeal conduits, pump, and other tubing, to provide a total dead volume of about 500 to 2500 ml.

The new flow-through cell culturing devices can be seeded with large numbers of cells. For example, a device with 20 plates having a total surface area of 20 cm², can be seeded with about 250,000 hepatocytes per plate and 750,000 fibroblasts per plate, to give a surviving and thriving population of about 5 million cells.

For use in human liver assist systems, approximately 5 to 25 billion hepatocytes are required, based on a total of 250 billion hepatocytes in a healthy human liver, and a fraction required for survival of about 2 to 10 percent. A device having a total surface area of about 2.0 to 10.0 m² can support this required number of hepatocytes, depending on cell mass. For example, if one chamber or unit has a surface area of 20×40 cm, i.e., a square area of 800 cm² (0.08 m²), then 25 units are required to obtain a total surface area of about 2.0 m², and 125 units are required for a total surface area of about 10.0 m².

One can also have smaller or larger individual units and accordingly increase or decrease the number of units in a given system to provide the required total surface area of 2.0 to 10.0 m².

Alternative Device Configurations

Other possible configurations included radial geometry, trapezoidal geometry, and square geometry.

EXAMPLES

The following examples and experimental methods and results are illustrative, but do not limit the scope of the invention described in the claims.

Example 1

Cylindrical, Single-Compartment Cell Culturing Devices

Figure 7A:
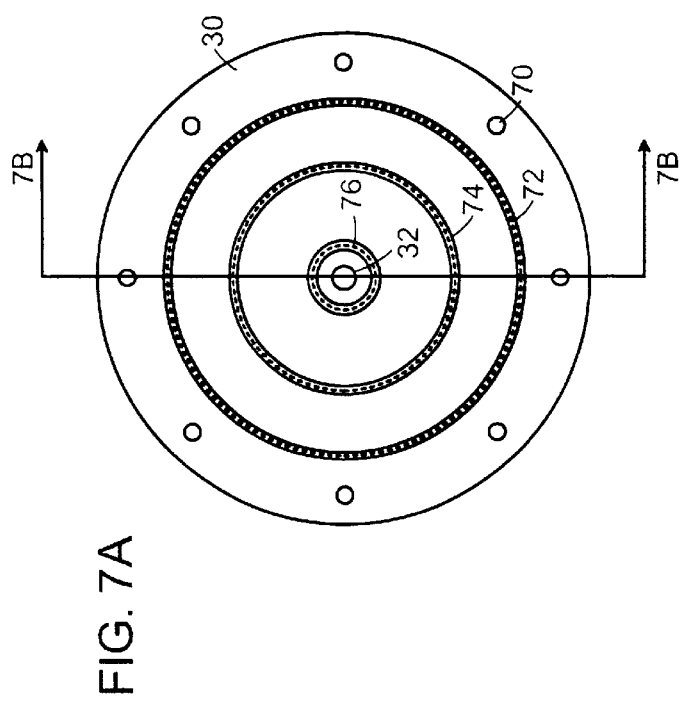
FIG. 7A is a top plan schematic view of a top of a cylindrical cell culturing device.
Figure 7B:
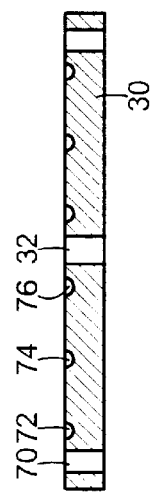
FIG. 7B is a schematic side cross-sectional view of the device top of FIG. 7A, along section line 7B—7B.

Specific cylindrical cell culturing devices shown generally in FIG. 3A were constructed and tested. The top cover 30 is shown in further detail in FIGS. 7A and 7B. The housing 16 is shown in further detail in FIGS. 8A and 8B. Flange 15 on housing 16 provides a surface to which cover 30 can be attached. Flange 15 includes holes 80 that correspond to through-holes 70 in cover 30. Cover 30 includes groove 72, that corresponds to groove 84 in flange 15 to accommodate an O-ring, e.g., of rubber or the like to provide a water-tight seal between the cover and the housing 16. Screws (not shown) can be used to secure cover 16 to flange 15 using these holes.

Figure 9B:
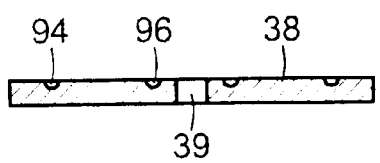
FIG. 9B is a schematic side cross-sectional view of the top manifold plate of FIG. 9A, along section line 9B—9B.

The top manifold plate 38 is shown in further detail in FIGS. 9A and 9B. The manifold plate includes grooves 94 and 96 which correspond to grooves 74 and 76 in top cover 30, to accommodate another O-ring to provide a water-tight seal between the cover and the manifold plate.

Figure 10B:
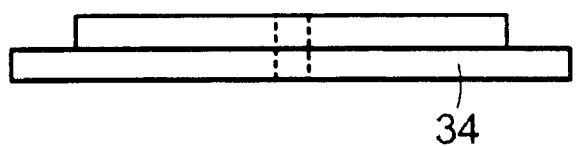
FIG. 10B is a schematic side elevation view of the device bottom of FIG. 10A.

The bottom 34 of the culturing device 10 is shown in further detail in FIGS. 10A and 10B. The bottom manifold plate (not shown) is one of the standard plates, but without a central hole. The spacer elements on the bottom of the bottom manifold plate are 500 microns in height.

Several cell culturing devices shown in FIGS. 7A to 10B were manufactured from PMMA or polycarbonate and had the following overall dimensions: housing, 1.25 inches high, by 2.5 inches outer diameter, 2.040 inches inner diameter; flange, 3.5 inches in diameter, by 0.25 inches high; top cover, 3.5 inches in diameter, 0.25 inches high, with an inlet hole (TAP 10-32, a standard thread specification for a luer fitting); top manifold plate, 2.0 inches in diameter, 0.125 inches high; bottom, 2.5 inches in diameter, by 0.125 inches high, with an outlet hole (TAP 10-32). Each device had a dead volume of 10 ml.

Each plate was made of glass and prepared with six spacer elements arranged on the bottom surface of each plate in two bolt-circles of 120 degree symmetry, i.e., spaced at 60° intervals. The spacer elements were made of UV cured acrylate cement and were microdeposited onto the plates. The plates were 2.0 inches in diameter, had a central hole of 3/16 of an inch diameter, and were 1.0 mm thick. Thus, each plate had an actual surface area of about 3.1 square inches, or about 20 cm².

The devices each contained 20 plates, plus a bottom and top pressure plate manifold plate, each with spacer elements 100 microns high, to create 20 seeded chambers with a uniform height of 100 microns.

Prior to assembly, each plate was rinsed in Chem-Solv® solution (which is an alkaline detergent that removes organic deposits from borosilicates) and then in deionized water, then in 3-[(2-aminoethyl)amino)]propyltrimethoxy-silane (2% v/v) for 30 seconds (to bind silane to the glass plates), and then in deionized water. The plates were then bathed in 2.5% glutaraldehyde in phosphate buffered saline (PBS) for 1 hour to later allow collagen to bind to the siloxane residues, and then rinsed in PBS. The plates were then rinsed in a 1:1 solution of 1 mg/ml collagen Type I:deionized water for 30 minutes at 37° C. to give the cells a binding agent to which they can become attached, rinsed in 70% ethanol for 10 minutes to become sterilized, rinsed in deionized water, rinsed in media (Dulbecco's Modified Eagle Medium (DMEM) with antibiotics and fetal bovine serum (FBS), and finally placed in sterile P60 dishes.

The plates were seeded with 250,000 rat hepatocytes per plate on Day 0. The cell culturing devices were seeded with rat hepatocytes, because these cells have already been shown to be compatible for use with both humans and animals. The choice of rat hepatocytes also complies with the requirement for large numbers of cells. On Day 1, murine 3T3 J2 fibroblasts were trypsinized and counted, treated with Mitomycin C (10 μ/ml), suspended in fibroblast media (880 ml DMEM, 100 ml bovine calf serum, and 20 ml penicillin/streptomycin), and seeded at 750,000 cells per plate, to give a total of about 5 million cells in one 20 plate device. On Day 3, the media was sampled to measure urea and albumin synthesis.

The entire assemblies, including housing, cover, top and bottom manifold plates, and conduits were sterilized in ethylene oxide, and the devices were assembled in a laminar flow hood. The flow circuits were primed with media and the housing (with bottom permanently attached) was filled with oxygenated media. The seeded glass plates were inserted individually, and stacked, one on top of the other, within housing 16, on top of bottom manifold plate 40, and then topped off with the top manifold plate 38.

DELRIN® rods were inserted into niches 82 in the housing wall before the plates were inserted, to assure an even space 17 between the plates 12 and the housing 16 around the entire periphery. The top cover was then attached to housing flange 15 with screws to seal the device, and conduits were attached to the inlet and outlet.

Example 2

Testing of Cylindrical Cell Culturing Devices

Once assembled, the cell culturing devices were tested for use in extracorporeal liver assist systems. Flow rates of 0.3, 1.0, and 6.0 ml/minute were tested.

A dispersion model was used to test the cell culturing devices. Dispersion measurement is used to evaluate stagnant fluid areas or bypassing of fluid within a bioreactor, which are undesirable. A small dispersion number indicates plug flow with minimal mixing, which is desirable.

Measurements were made by filling the bioreactor and flow circuit with water. Flow was initiated by setting the peristaltic pump for the desired flow rate; in this case two flow rates were used, 0.3 ml/min and 1.0 ml/min. The output of the reactor was connected to a flow-through spectrophotometer to measure the concentration of a protein solution (BSA, bovine serum albumin). The BSA was instilled into the flow circuit upstream of the reactor as a pulse input. The spectrophotometer was connected to a chart recorder so that a continuous measurement of the BSA output could be obtained over time. A dispersion coefficient was calculated using the equation:

$$v = 2Nd - 2Nd^2[1 - \exp(-1/Nd)]$$

where v=variance of outlet protein concentration measured by the spectrophotometer, Nd is the dispersion number (D/UL), D is the diffusion coefficient, U is the linear velocity (cm/sec), and L is the length. Results of these studies determined that the dispersion number was 0.0435 at a flow rate of 0.3 ml/min and 0.05 at a flow rate of 1.0 ml/min. These low dispersion numbers indicated that there is plug flow and minimal dispersion within the reactor.

Example 3

A Mathematical Model of a Cylindrical, Single-Compartment Cell Culturing Device A mathematical model was created to determine the effects of varying numerous parameters within a cylindrical cell culturing device. The model was based on a cylindrical device as shown in FIG. 3, with ten chambers, each chamber formed of an upper plate and a lower plate, as shown in FIGS. 1A and 1B. In the model, hepatocytes were seeded only on the lower disc (z=0) of each pair.

The plasma enters at $r=R_i$ (internal radius of the discs, the chamber inlet) and exits through the edges, $r=R_e$ (the chamber outlet). Thus, the cross section perpendicular to the flow increases proportionally with the radius as the flow proceeds from the center to the edge. Several chambers are connected in parallel, for example, one on top of the other, having a height H, that was generally set at 50 microns, but was varied from 25 to 100 microns for certain simulations as described below.

Each chamber had an internal radius, $R_i=0.3$ cm, and an external radius, $R_e$ of 2.55 cm. These dimensions provide an efficient distribution of the plasma among the chambers while keeping the dead volume small. The critical radius, $R_c$, determines the actual surface area of the plate, and is the external radius minus the internal radius. Thus, the $R_c$ was 2.25 cm, and the surface area of each plate was about 20.15 cm$^2$.

In the model the maximal allowable dead volume of the liver assist system was 3 ml. This represents roughly 30% of the total rat blood volume. Approximately 1 ml was allocated for the volume occupied by the chambers, and the rest was left for tubing, interconnects, and the volume inside the housing outside of the chambers.

The total plasma flow rate (Q) in an extracorporeal perfusion system connected to a rat (of about 200 g) is approximately 0.3 ml/min as reported by Stefanovich et al., J. Surg. Res., 66:57–63 (1996). This represents approximately 25% of the rat's arterial blood that enters the plasma separator, e.g., 25% of the blood entering the plasma separator, by volume, is filtered across the hollow fibers and becomes plasma, per unit time. The other 75% of the blood volume leaves the separator as concentrated red blood cells. For the model, the oxygenated plasma flow rate was varied between 0.3 and 1.2 ml/minute.

The gas flow to the cell culturing device was set to ensure adequate oxygen for the cells to survive and remain functional. A typical average post-seeding value of $V_{max}$ (maximal oxygen uptake rate, OUR) was used in the model. Specifically after the 8th day of culture, $V_{max}$ was set at 0.25 nmoles $O_2$/s/10$^6$ cells. Previous studies have shown that the oxygen uptake rate (OUR) vs. oxygen tension behavior of both murine and rat hepatocytes follow very closely a first-order Michaelis-Menten process. Therefore, Michaelis-Menten kinetics were used to accurately model the OUR of the hepatocytes. This model, depicted in Eq. (11), requires the knowledge of the oxygen partial pressure at which the OUR is half-maximal ($K_m$). In the model, $K_m$ was set to 5 mmHg, which is an average of the values previously reported after the 8$^{th}$ day of culture.

It has been postulated that the partial pressure of oxygen may have an important role in urea synthesis, lipid metabolism, cytochrome P-450 activity and gluconeogenesis both in vivo and in vitro. These specific liver functions are known to be localized within a specific zone of the sinusoidal endothelium, where the oxygen tension ranges between 90 and 5 mmHg. As a consequence, the preservation of the hepatocyte functions in a cell culturing device used in a liver assist system can be achieved by exposing the hepatocytes to an oxygen tension gradient similar to the one observed in vivo.

In the mathematical model the initial oxygen tension was set to 380 mmHg (50% oxygen dissolved in plasma) and a minimal (cut-off) oxygen tension ($K_m^*$) at the outlet was set to 5 mmHg. Although the inlet oxygen tension in the cell culturing device chambers is higher than that observed in vivo, such a high oxygen tension is required for chambers that are long enough to accommodate a sufficient number of hepatocytes.

Mathematical simulations were run using different hepatocyte densities ranging from 50,000 to 200,000 cells/cm². The results showed no significant differences in the total amount of cells without oxygen limitations.

The hepatocytes in the device will be subjected to a mechanical stress that might have detrimental effects on their function and viability. In the model a conservative threshold shear stress was set at 10 dyne/cm². In addition, typical in vivo values of pressure drop were used as an upper limit in the calculations. For example, a pressure drop between 1.5 and 9 mmHg from the portal vein to the hepatic vein has been reported. As a result, a conservative pressure drop was set at 8 mmHg (~10,000 dynes/cm²).

An adult rat liver has approximately 350 million hepatocytes. It has been estimated that the minimal fraction of liver mass necessary for survival ranges between 2–12%. Therefore, an intermediate value, namely, 6% of the total number of hepatocytes in the liver was used in the experiments. This estimate gives a total of about 20 million hepatocytes in the cell culturing device necessary to support a living rat.

The mathematical simulations were developed in a two-dimensional domain as shown in FIG. 1B. The flow is two-dimensional because it is independent of the angular coordinate (i.e., axy-symmetric). The model was simplified by assuming that the flow originated at a segment of the axis of symmetry, r=0. In other words, the possible transitions between axial and radial flow were neglected.

The set of dimensionless conservation equations for mass, momentum, and species (oxygen) that correspond to the configuration shown in FIGS. 1A and 1B are:

$$\frac{\partial \tilde{v}_r}{\partial \tilde{r}} + \frac{\tilde{v}_r}{\tilde{r}} + \frac{\partial \tilde{v}_z}{\partial \tilde{z}} = 0 \tag{1}$$

$$\tilde{v}_r \frac{\partial \tilde{v}_r}{\partial \tilde{r}} + \tilde{v}_z \frac{\partial \tilde{v}_r}{\partial \tilde{z}} = -\frac{\partial \tilde{p}}{\partial \tilde{r}} + \frac{1}{Re_D}\left(\frac{\partial^2 \tilde{v}_r}{\partial \tilde{r}^2} + \frac{1}{\tilde{r}}\frac{\partial \tilde{v}_r}{\partial \tilde{r}} - \frac{\tilde{v}_r}{\tilde{r}^2} + \frac{\partial^2 \tilde{v}_r}{\partial \tilde{z}^2}\right) \tag{2}$$

$$\tilde{v}_r \frac{\partial \tilde{v}_z}{\partial \tilde{r}} + \tilde{v}_z \frac{\partial \tilde{v}_z}{\partial \tilde{z}} = -\frac{\partial \tilde{p}}{\partial \tilde{z}} + \frac{1}{Re_D}\left(\frac{\partial^2 \tilde{v}_z}{\partial \tilde{r}^2} + \frac{1}{\tilde{r}}\frac{\partial \tilde{v}_z}{\partial \tilde{r}} + \frac{\partial^2 \tilde{v}_r}{\partial \tilde{z}^2}\right) \tag{3}$$

$$\tilde{v}_r \frac{\partial \tilde{C}}{\partial \tilde{r}} + \tilde{v}_z \frac{\partial \tilde{C}}{\partial \tilde{z}} = \frac{1}{Re_D}Sc\left[\frac{1}{\tilde{r}}\frac{\partial}{\partial \tilde{r}}\left(\tilde{r}\frac{\partial \tilde{C}}{\partial \tilde{r}}\right) + \frac{\partial^2 \tilde{C}}{\partial \tilde{z}^2}\right] \tag{4}$$

where Eqs. (2)–(3) are the Navier-Stokes equations of fluid motion in steady state assuming nearly constant properties evaluated at 37° C.

The nondimensional variables used for writing Eqs. (1)–(4) are:

$$(\tilde{r}, \tilde{z}) = \frac{(r, z)}{D_h} (\tilde{v}_r, \tilde{v}_z) + \frac{(v_r, v_z)}{U} \tag{5}$$

$$\tilde{p} = \frac{p}{U^2 \rho} \tilde{C} = \frac{C}{C_i} \tag{6}$$

$$Re_D = \frac{U D_h}{v} Sc = \frac{v}{D} \tag{7}$$

where Sc is the Schmidt number, $Re_D$ is the Reynolds number based on the hydraulic diameter, v is the kinematic viscosity ($v=\mu/\rho=0.01$ cm²/s), C is the oxygen concentration, $C_i$ is the inlet oxygen concentration, $D_h$ is the hydraulic diameter ($D_h=2H$), U is the mean velocity at the inlet (r=$R_i$), p is the pressure, D is the diffusivity of oxygen in plasma ($2 \times 10^{-5}$ cm²/s), and $\rho$ is the density of the fluid.

The numerical work was conducted in a two-dimensional computational domain represented by one chamber [($R_e$−$R_i$)×H] fitted with a downstream section $L_d$×H. This allowed appropriate outflow boundary conditions to be imposed [Eq. 10]. $L_d$ was chosen based on accuracy tests described below. Its dimensionless value was $L_d/L=0.05$.

The flow boundary conditions were: uniform horizontal velocity at the channel inlet; no slip and no penetration on the walls of the channel; and zero shear at the outlet. In addition, the boundary conditions for Eq. (4) are:

$$\tilde{C}=\tilde{C}_0 \, at \, \tilde{r}=0 \tag{8}$$

$$\frac{\partial \tilde{c}}{\partial \tilde{r}} = 0 \, at \, \tilde{z} = \tilde{h} \tag{9}$$

$$\frac{\partial \tilde{C}}{\partial \tilde{r}} = 0 \, at \, \tilde{r} = \tilde{L} \tag{10}$$

The boundary condition at z=0 is the OUR of the hepatocytes. It is not constant because cells adapt to depletion of oxygen by reducing their OUR. Hence, the oxygen concentration profile C(r,z) in the chamber is a function of the oxygen concentration at the surface with attached cells, $C_s(r)$. Using Michaelis-Menten kinetics the OUR of the hepatocytes is modeled as:

$$D\left(\frac{\partial C(r, z)}{\partial z}\right)_{z=0} = V_{max} \frac{C_s(r)}{K_m + C_s(r)} \tag{11}$$

Equations (1)–(4) were solved using a Galerkin finite element code (FIDAP, Fluid Dynamics International, Evanston, Ill. 06020 (1993)), and a sufficiently fine grid with quadrilateral elements and biquadratic interpolating functions for the velocities and oxygen concentration. The pressure was eliminated using the penalty formulation and reduced integration with a penalty parameter $\epsilon=10^{-8}$. The results were shown to be nearly insensitive to the penalty parameter. An attenuation factor of 0.5 was applied to all the degrees of freedom to maintain the convergence under control. The Stokes problem was solved first to obtain a good initial guess for the velocity field. Subsequently, the velocities converged in less than 5 successive substitution iterations. The convergence for the species equation (4) took roughly between 40 and 60 Broyden (quasi-Newton) itera tions. The following criteria were used to stop the simulations:

$$\frac{\|\Delta u_i\|}{\|u\|} \leq 10^{-3} \text{ and } \frac{\|R(u_i)\|}{\|R_0\|} \leq 10^{-3} \quad (12)$$

where $\|\cdot\|$ is the Euclidean norm, $u_i$ is the solution vector at iteration i, and $R(u_i)$ is the residual vector. The fast convergence of the velocity field in the Navier-Stokes equations is due to the use of the Stokes solution as an initial guess. However, such a good initial guess to start the iterative process could not be provided with the species equation [Eq. (4)].

The mesh was uniform in r with 401 nodes and nonuniform in z with between 29 and 37 nodes. Accuracy tests showed that the solutions are mesh independent. The grid fineness was increased until the relative changes on the integrated mean oxygen concentration in all the computational domain was less than 0.1 percent when the number of nodes was increased by 25 percent in each direction. Another set of accuracy tests indicated that the integrated mean oxygen concentration was relatively insensitive to doubling of the downstream length ($L_d$) of the computational domain.

Example 4

Mathematical Results: Oxygen Transport Inside the Chambers

Low oxygen tension decreases viability and function of hepatocytes, which mandates that the hepatocyte-seeded surfaces in the new cell culturing device be efficiently oxygenated. The constraints on device dimensions and flow conditions imposed by the oxygen consumption of hepatocytes inside the chamber of FIG. 1A were modeled. The objective was to find the optimal plasma flow rate that would guarantee that 20 million hepatocytes in the bioreactor are exposed to a minimal acceptable oxygen tension, $K_m^*=5$ mmHg. Other parameters were varied to study their impact on the oxygen transport in the chambers.

The Effect of the Plasma Flow Rate

Figure 11:
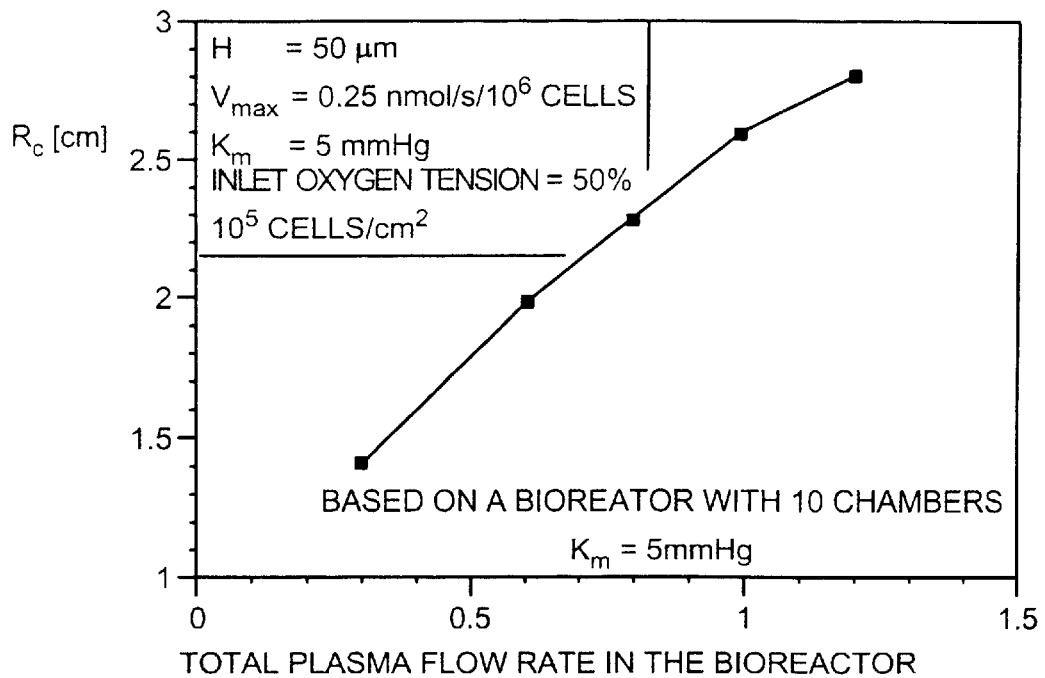
FIG. 11 is a graph of total plasma flow rate in a mathematical model of the new cell culturing device vs. critical radius of plates within the device.

The achievable chamber radius or critical radius, $R_c$, is the radius at which the oxygen tension at the surface with attached hepatocytes is equal to $K_m^*$, the minimal acceptable oxygen tension. FIG. 11 depicts $R_c$ as a function of the total plasma flow rate in the device. Higher plasma flow rates provide a larger $R_c$ and more cells exposed to oxygen tensions above $K_m^*$ due to the increase of the oxygen convection. Moreover, to have 20 million hepatocytes ($R_c$= 2.55 cm, when cells are seeded at $10^5$ cells/cm$^2$) exposed to an oxygen tension above $K_m^*$, Q must be about 1 ml/min. In other words, each chamber must be perfused with plasma at 0.1 ml/min. Generally, higher plasma flow rates (faster circulation of the plasma in the chambers) increase the levels of oxygen concentration in the plasma.

Sensitivity of the Model to the OUR Parameters, $V_{max}$ and $K_m$ $V_{max}$ and $K_m$ are experimentally determined variables subject to variability depending on the duration of culture, and the cell microenvironment. As a result, the effect of varying $V_{max}$ and $K_m$ were investigated. Although these parameters cannot typically be manipulated or changed via design of the device, it is critical to define the sensitivity of the model to these parameters.

Figure 12:
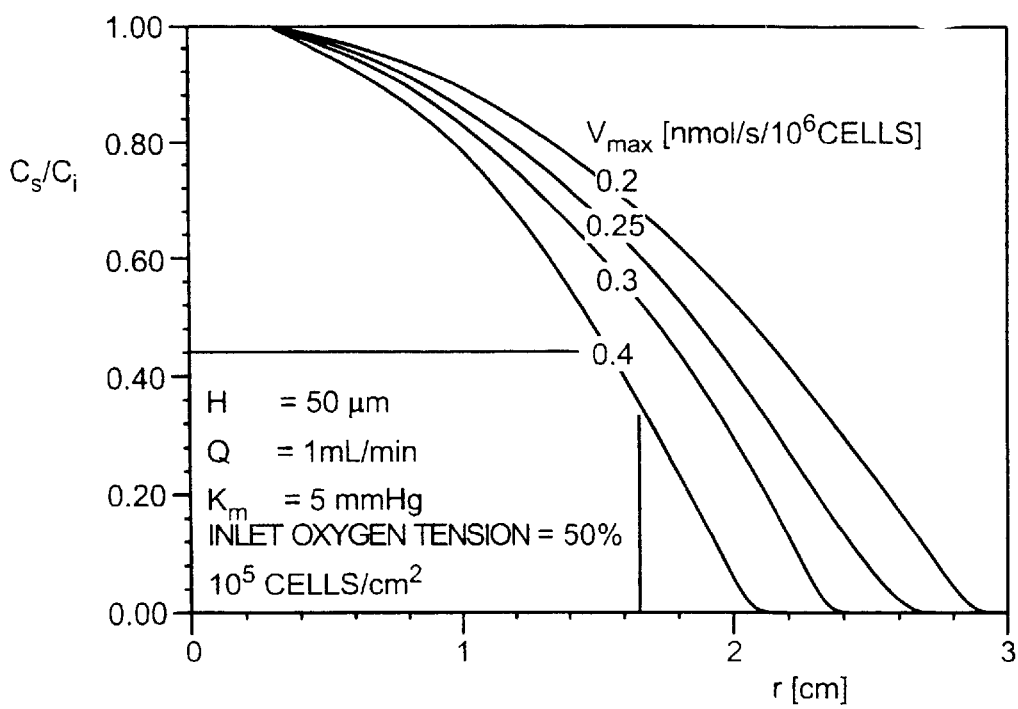
FIG. 12 is a graph of the radius of plates vs. normalized oxygen tension at the plate surface in a mathematical model of the new device, with $V_{max}$ (maximal oxygen uptake rate (OUR)) varied from 0.2 to 0.4 nmol/s/$10^6$ cells.

The total plasma flow rate into the cell culturing device is kept constant at 1.0 ml/min because it has already been found in FIG. 11 that such Q can maintain a device with 10 chambers having $R_c=R_e=2.55$ cm (20 million cells exposed to an oxygen tension above $K_m^*$). In FIG. 12, $V_{max}$ is varied from 0.2 to 0.4 nmol/s/$10^6$ cells, because these values bracket the experimentally determined baseline $V_{max}$ of 0.25 nmoles/sec/$10^6$ after 8 days of hepatocyte culture. The values shown in the ordinate represent the oxygen tension at the surface of the chamber with attached hepatocytes, normalized with respect to the initial (inlet) oxygen tension.

Perturbations in $V_{max}$ have a dramatic effect on reactor design. The critical radius increases from 2.1 cm when $V_{max}=0.4$ nmol/s/$10^6$ cells, to 2.9 cm when $V_{max}=0.2$ nmol/s/$10^6$ cells, corresponding to an increase in viable cell number from 13.5 to 26.1 million. These results show that identification of $V_{max}$ is critical to the proper design of the device flow length and geometry. Improper design would lead to hypoxic cell conditions and massive cell death within the cell culturing device.

Figure 13:
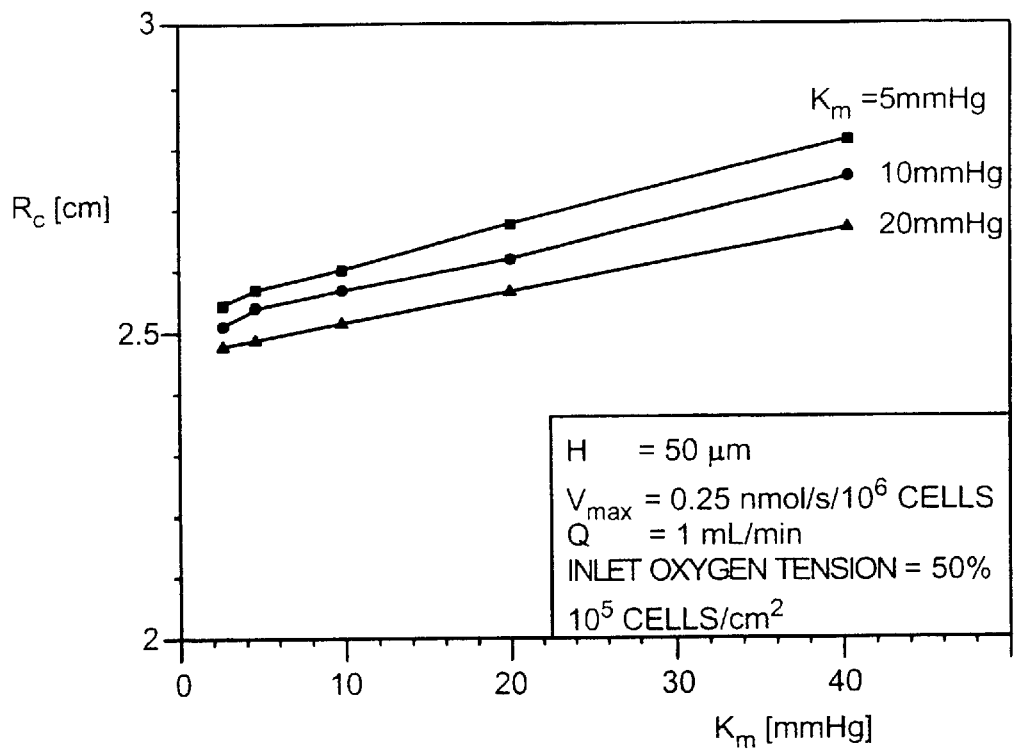
FIG. 13 is a graph of oxygen tension ($K_m$) vs. critical radius ($R_c$) of the plates in a mathematical model of the new device, showing that $R_c$ is quite insensitive to $K_m$.

The sensitivity of the oxygen profile to variations in $K_m$ is shown in FIG. 13. The ordinates depicts the critical radius for different values of $K_m^*$. The variation in $R_c$ between 2.5 and 2.8 cm only make the number of hepatocytes operating above $K_m^*$ increase from 19.3 million to 24.3 million. The fact that $R_c$ is almost insensitive to $K_m$ becomes more clear if oxygen tension $K_m$ itself is chosen as a minimum (cut-off), in other words, $K_m^*=K_m$. Reading $R_c$ from FIG. 13 it appears that in the range $5<K_m<20$ mmHg, $R_c$ will always be close to 2.55 cm, given $K_m^*=K_m$.

Oxygen Tension at the Chamber Inlets

The plasma can be easily oxygenated in the extracorporeal circuit by either incorporating a membrane oxygenator or through use of gas permeable tubing. Although oxygen tension is a potentially well-regulated factor in the device design, a few aspects should be taken into account before choosing an inlet oxygen tension for the operation of the device in a liver assist system. Increases in inlet oxygen tension will increase the number of hepatocytes that are exposed to oxygen tensions above $K_m^*$. While, it is not certain whether high oxygen tensions could have a negative effect on the cells, it has been hypothesized that high levels of oxygen may cause oxidative damage by free radicals. Therefore, the highest oxygen tension at the inlet of the chambers should be limited to that required to achieve our desired chamber length with all hepatocytes above $K_m^*$.

Figure 14:
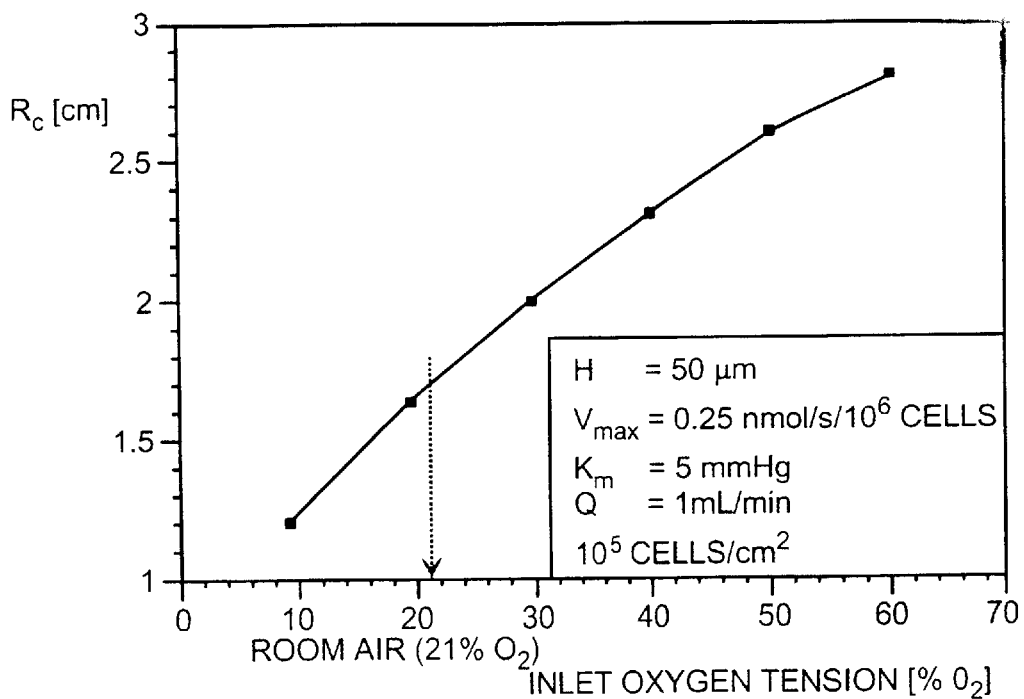
FIG. 14 is a graph of inlet oxygen tension v. $R_c$ which shows that the $R_c$ increases as the inlet oxygen tension increases in a mathematical model of the new device.

The range between 10–60% (76–456 mmHg) of oxygen dissolved in plasma at the inlet of the chambers was studied in the model. FIG. 14 shows the increase in the critical radius as the inlet oxygen tension becomes higher. For example, if room air is used to oxygenate the plasma, the critical radius is approximately 1.6 cm (~7.8 million hepatocytes above $K_m^*$). However, if the inlet oxygen tension is increased to 60%, the total number of hepatocytes above $K_m^*$ would be nearly 23 million at a critical radius of 2.8 cm. This three-fold increase in the total number of hepatocytes corroborates that, at least in theory, the initial oxygen tension is an excellent regulator of the oxygen distribution in the device chambers.

Since an inlet oxygen tension of 380 mmHg is required to obtain 20 million viable cells ($R_c=2.55$ in FIG. 14), the possibility of oxidative damage becomes an important issue. In fact, the oxygen tension needs to be monitored to keep this level below about 150 mmHg, because at an oxygen tension above about 154 mmHg, oxygen is toxic to cells.

The Effect of Chamber Height

Figure 15:
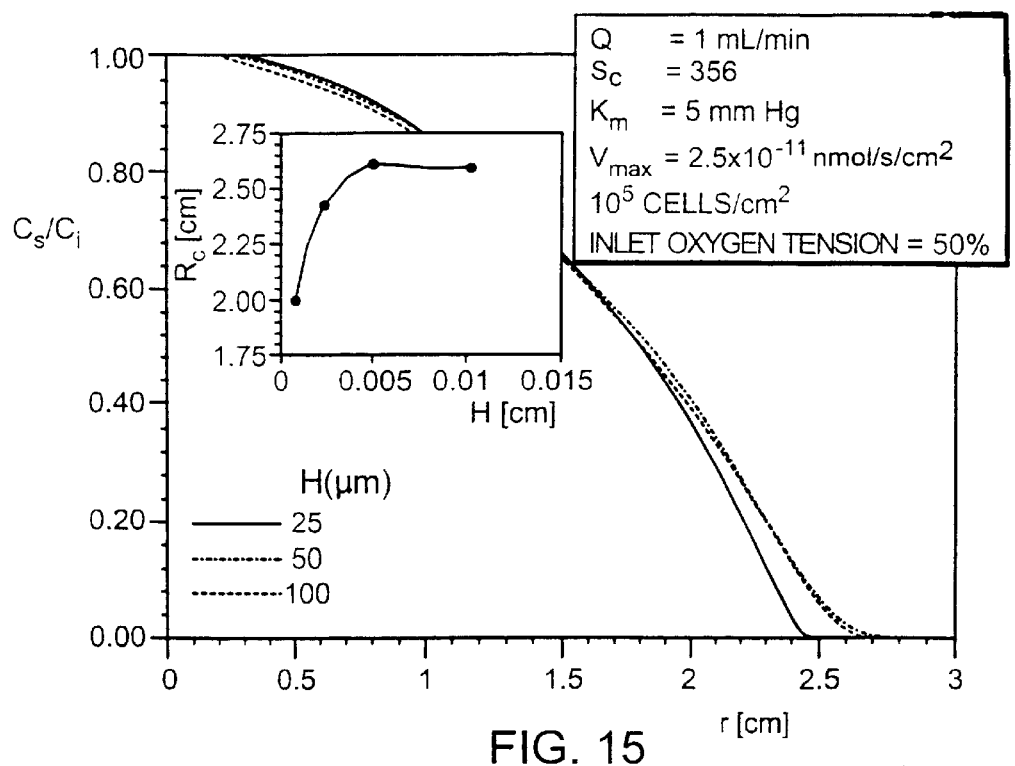
FIG. 15 is a graph of the radius of the plates in a mathematical model of the new cell culturing device vs. normalized oxygen tension at the plate surface, with height of the chambers (H) varied from 25 to 100 microns.

The influence of H on the oxygen tension under a constant plasma flow rate of 1 ml/min (0.1 ml/min on each chamber)

was also studied in the model. FIG. 15 depicts the dimensionless oxygen concentration profile at the plate surface covered with cells. The results show that H has a weak effect on the oxygen concentration profile at the surface with attached cells. It is worth noting that $R_c$ has a shallow maximum at an H of about 50 µm (shown as an inset in FIG. 15). This can be explained with the asymptotic behavior of the oxygen transport. When H is large, the flow velocity becomes very slow and the oxygen transport is diffusion-limited. In the other extreme, when H is small, the flow velocity becomes large, but the plasma volume vanishes as does the oxygen.

These results have several implications. First, in the studied range, the height of the chambers does not play an important role in the efficiency of the oxygen transport. However, it imposes a constraint when keeping the dead volume of the cell culturing device small, which is important to overall design. As discussed below, H also has an important effect on both the shear stress and the pressure drop inside the bioreactor chambers.

Shear Stress and Pressure Drop

The constraints in the cell culturing device imposed by the hydrodynamics of the plasma flow within the chambers were also modeled. The following solution for creeping flow between to parallel plates with radial flow was used to unveil the most important parameter affecting both the shear stress and pressure drop:

$$\tau_w = \frac{3\mu Q}{\pi H^2 r} \quad (13)$$

where $\tau_w$ is the shear stress. Similarly, the pressure drop is also inversely proportional to the chamber height, $\Delta P \sim 1/H^3$. As a result, the variation of the shear stress and pressure drop in the chambers will be strongly affected by the height of the chambers, H.

The shear stress at the lower disc is obtained from the numerical results as:

$$\tau = \tau_{rz} = -\mu \frac{\partial v_r}{\partial z} \quad (14)$$

Additionally, the pressure solution is recovered from the formulation of the penalty function:

$$\frac{\partial v_r}{\partial r} + \frac{V_r}{r} + \frac{\partial v_z}{\partial z} = -\varepsilon p \quad (15)$$

Figure 16:
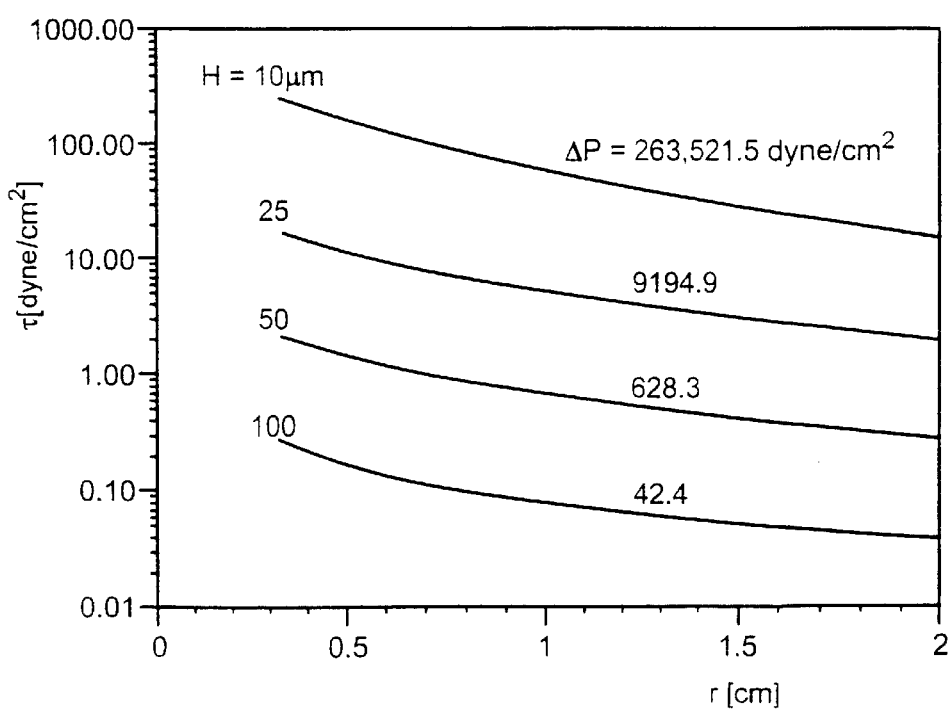
FIG. 16 is a graph of pressure drop and shear stress as a function of plate radius in a mathematical model of the new device, with H varied from 10 to 100 microns.

FIG. 16 depicts both the pressure drop and shear stress as a function of the chamber radius for four different values of H. The plasma flow rate in the cell culturing device is 1 ml/min (0.1 ml/min in each chamber). In addition, the pressure drop values are based on a chamber with $R_c = 2.5$ cm. The qualitative predictions of Eq. (13) are corroborated by the curves shown in FIG. 16. Reducing the chamber height from 50 to 25 µm produces an increase from roughly 2 to 15 dyne/cm$^2$ in the maximal shear stress, which occurs at the inlet of the chamber. A similar steep change can be observed in the pressure drop across the chamber. When H is lower than 25 µm the pressure drop becomes higher than 10,000 dyne/cm$^2$ and the hepatocytes can be negatively affected. The shear stress when H is lower than 25 µm is also undesirable.

In brief, observing the effect of H on the oxygen transport (inset of FIG. 15) and hydrodynamics, H can be chosen to be between 25–500 µ(with 25 to 100 or 200 being the practical boundaries). If 50 µis used, for example, the contribution of the chambers to the dead volume is only 1 ml, leaving 2 ml for additional void space in the cell culturing device.

Example 5

Two-Compartment Cell Culturing Devices

Materials

William's Medium E, 4-{2-Hydroxyethyl}-1-piperazine-ethane-sulfonic acid (HEPES), L-glutamine, glucose, and collagenase were purchased from Sigma (St. Louis, Mo.), newborn calf serum (NBCS), penicillin, and streptomycin were purchased from Life Technologies (Gaithersburg, Md.), hydrocortisone from Abbott Laboratories (North Chicago, Ill.), epidermal growth factor (EGF) from Collaborative Research (Bedford, Mass.), glucagon from Eli Lilly and Co. (Indianapolis, Ind.) and porcine insulin from Novo Nordisk A/S (Bagsuaerd, Denmark). Culture medium for experiments consisted of William's E medium supplemented with 1% (v/v) NBCS, 200 units/mL penicillin, 200 units/mL streptomycin, 7.5 mg/mL hydrocortisone, 20 ng/mL EGF, 7 mg/mL glucagon, 0.5 units/mL insulin, 10 mM HEPES, 4 mM L-glutamine and 4.5 g/L glucose. The pH of the culture medium, when equilibrated with 10% CO2, was 7.4. Gas mixtures were obtained from BOC Gases (Hingham, Mass.), and gas compositions were certified to be accurate to within 0.05 mmHg. Ultrapure nitrogen for oxygen exclusion jacketing was certified to be 99.998% pure (Grade "4.8"; 20 ppm total impurities, 5 ppm oxygen, 1 ppm hydrocarbons, and 3 ppm water).

Hepatocyte Isolation and Culture

Porcine hepatocytes were isolated from 8.3+/−3.0 kg Yorkshire/Hampshire hybrid pigs (Parsons, Inc., Hadley, Mass.) using standard techniques. Briefly, pigs were anesthetized, heparinized, and the portal vein of the exposed liver was cannulated. Four to 5 liters of cold (4° C.) Ringers Lactated Buffer (RLB) was infused at a rate of 200 to 250 mL/min. One liter of 0.2% EDTA, maintained at 37° C., was then infused at a rate of 150 mL /min. This was followed by enzymatic digestion with perfusion of buffered collagenase, pH 7.4, at a flow rate of 150–200 mL/min. The tissue was then progressively processed through 200 and 100 micron stainless steel sieves and washed in cold medium. Typically, between 3.0×10$^9$ and 14×10$^9$ cells were obtained (mean= 6.7×109) with viabilities ranging from 65 to 90% (average: 85%), as determined by trypan blue staining. The resulting hepatocyte stock solution was diluted in William's E medium to a concentration of 1×10$^6$ cells/mL.

Porcine hepatocytes were cultured on 25×75 mm glass slides (Baxter Diagnostics, Inc., Deerfield, Ill.) coated with a 1:5 solution of 1.2 mg/mL Type I collagen and DI water, prepared using a procedure modified from Elsdale and Bard, *J Cell Biol.*, 54:626–637 (1972), as described by Dunn et al., *Biotechnology Progress*, 7:237–245 (1991), with the key modification being the titration of the resulting solution to pH 5.0. Following a 1 hour incubation at 37° C., the slides were washed twice with William's E medium. Prior to collagen coating, each glass slide was placed in a custom molded polydimethylsiloxane (PDMS, Sylgard 184, Dow Coming, Lansing, Mich.) seeding chamber and this assembly was sterilized using 70% ethanol in water for 1 minute and rinsed twice with William's E medium. The assembly was then placed in a sterile P100 tissue culture dish (Falcon, Lincoln Park, N.J.). Placement of the slides in the PDMS seeding chambers allowed for collagen coating and seeding of the slide with hepatocytes without spillage over the edges of the slide. Since the goal of the seeding was to obtain a confluent layer of cells on the glass slide, porcine hepatocytes were subsequently seeded twice on the precoated glass slides with 2 mL of a $1\times10^6$ cell/mL suspension. Between each seeding cultures were incubated at 37° C. with a 10% $CO_2$ environment for 1 hour. After the first seeding, the media was aspirated and 2 mL of the same hepatocyte suspension was again placed on the slides. The cultures were again incubated at 37° C. in a 10% $CO_2$ environment and allowed to stabilize for 24 hours prior to their use for experiments.

Two-Compartment Parallel-Plate Bioreactor with an Internal Membrane Oxygenator

Figure 17A:
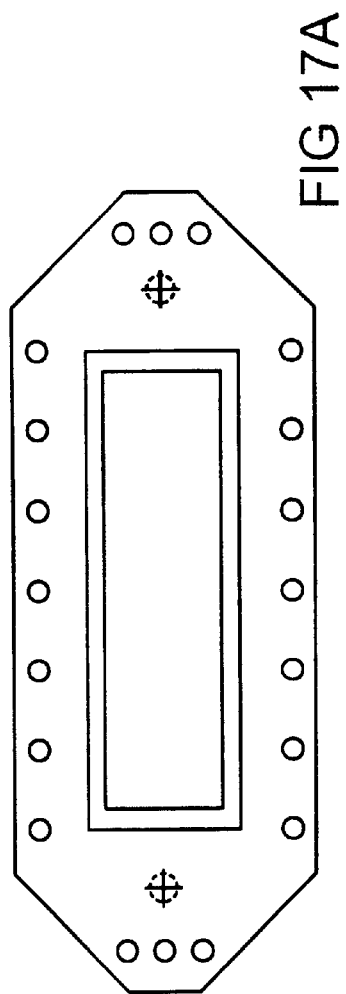
FIGS. 17A and 17B are schematic diagrams of a top plate of a two-compartment cell culturing device in top and side views, respectively.
Figure 17B:
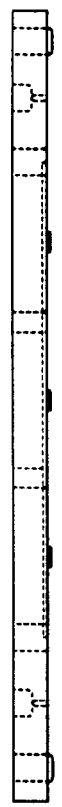
Figure 17C:
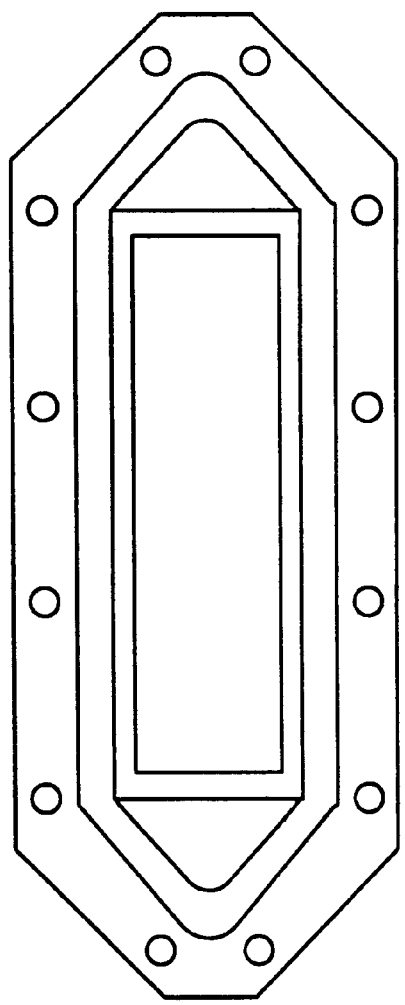
FIGS. 17C and 17D are schematic diagrams of a bottom plate of a two-compartment cell culturing device in top view and side view, respectively.
Figure 17D:
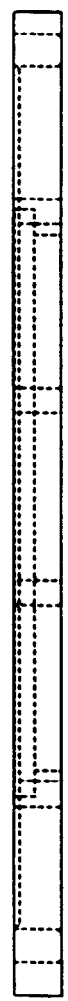

The bioreactor with the internal oxygenation membrane consisted of a custom-machined polycarbonate upper and lower plate. These upper and lower plates are shown in FIGS. 17A and 17B, respectively. As shown in FIG. 17A, the upper plate contained Luer inlet and outlet ports and a 25 mm×75 mm recess milled out and replaced with a glass slide secured and embedded with silicone sealant (734 RTV Sealant, Dow Corning, Midland, Mich.). The glass slide window was sealed in so that it was under flush to the lower surface. A 25 mm×75 mm stainless steel woven screen (Small Parts Inc., Miami Lakes, Fla.) was silicone sealed to the glass slide so that it was flush to the lower surface of the plate. Inlet and outlet ports for oxygenating gas flow were placed, adjacent to the ends of the glass window, into the polycarbonate. A polyurethane gas permeable membrane (Breathe-Easy, Diversified Biotech, Boston, Mass.), in which one side had an adhesive surface, was attached to the lower surface of the upper plate, including the stainless steel woven screen. This membrane allowed for the separation of oxygenating gas above the membrane and flowing medium below the membrane.

As shown in FIG. 17B, the lower plate had a 25 mm×75 mm recess milled out to accept a glass slide that was silicone sealed in place, but this slide was one slide thickness under flush to the upper surface of the plate. These silicone-sealed glass slides functioned as windows that allowed for transillumination viewing under a microscope. A 0.25 mm thick medical-grade silicone gasket (Specialty Silicone Fabricators, Inc., Paso Robles, Calif.) separated the two plates and was seated into a recess milled into the lower plate. The assembled device held a 25 mm×75 mm×1.0 mm glass slide (Baxter Diagnostics Inc., Deerfield, Ill.) with a confluent layer of cultured hepatocytes. The effective chamber dimensions were 25 mm×75 mm×0.1 mm (w×l×h). The width of the chamber gradually expanded from 3 mm at the inlet and outlet regions to 25 mm at the glass slide, with this expansion allowing for the establishment of uniform flow conditions.

During assembly, the bottom plate of the bioreactor was filled with medium and the glass slide with cultured hepatocytes was placed into proper position. The inlet port in the upper plate was connected to the flow circuit, which was already being perfused with medium. The upper plate was then lowered onto the lower plate at a slight angle to allow medium to overflow so that entrapment of air bubbles could be avoided. Pressure was applied to the upper plate as the thumbscrews were tightened and secured, to prevent the introduction of bubbles during the final assembly process.

To ensure that the bioreactors were well perfused and free of stagnant flow regions, flow visualization was employed. Trypan blue was introduced at the bioreactor inlet at a flow rate of 1.0 mL/min, displacing DI water already present within the chamber, and the flow pattern was visually observed. The moving dye front remained flat and was uniformly distributed in the bioreactor. There were no visible regions of back-mixing or stagnant flow.

To quantify the leakage rate of oxygen out of the flow circuit, a standard curve was generated by setting up the flow circuit as previously described with the one-compartment bioreactor and without hepatocytes. All tubing, the bioreactor, and the Clark electrode were placed into a shroud, which was continuously purged with high-purity nitrogen gas (<0.05 mmHg PO2) throughout the duration of the experiment. The medium was equilibrated with 21% $O_2$, 10% $CO_2$, 69% $N_2$. The outlet $PO_2$ was measured at medium flow rates ranging from 0.1 mL/min to 1.0 mL/min. At a flow rate of 1.0 mL/min, the outlet $PO_2$ was 153.5 mmHg. For flow rates between 0.5 mL/min and 0.9 mL/min, the outlet $PO_2$ remained stable between 146 mmHg and 150 mmHg, respectively. At 0.1 mL/min, the outlet $PO_2$ decreased to 115.5 mmHg. Potential sources of leakage within the flow circuit included the PHAR-MED tubing interconnecting the stainless steel tubing to the Luer fitting tube barbs, the bioreactor itself at the silicone sealant interface between the glass windows, the polycarbonate top and bottom plates, the silicone gasket separating the top and bottom plates of the bioreactor, and/or the flow-through housing of the Clark electrode. From this standard curve, the difference between the inlet PO2 and the outlet PO2, for each flow rate from 0.5 mL/min to 0.9 mL/min, was added to the measured outlet PO2 values obtained for each corresponding flow rate used in the outlet oxygen experiments. The difference between inlet PO2 and the outlet PO2 at 1.0 mL/min measured on the standard curve was added to all values of outlet PO2 measured at flow rates of 1.0 mL/min and above. For values of outlet PO2 at 0.1 mL/min, no correction factor was necessary as the oxygen leakage out of the flow circuit at this low flow rate was minimal due to the small driving force (i.e., low PO2 inside the flow circuit due to oxygen consumption by the hepatocytes and low PO2 outside in nitrogen shroud). This is supported by the fact that the outlet PO2, of the one-compartment bioreactor with hepatocytes, at a flow rate of 0.1 mL/min was close to 0 mmHg.

Alternative Two-Compartment Bioreactors

Figure 18:
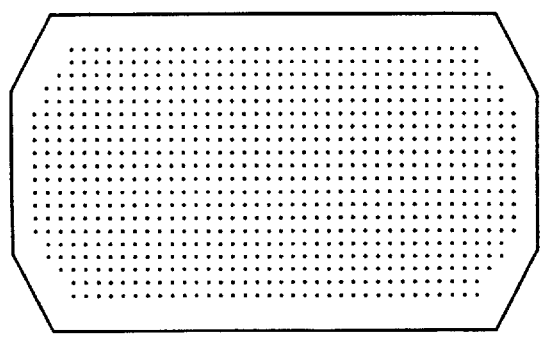
FIG. 18 is a schematic top view of a perforated support plate.

Alternative bioreactor designs include a solid, perforated substrate to support the gas-permeable membrane. Such a solid support is shown in FIG. 18. The metal plate is perforated by over 700 holes of 0.0485 inch diameter, separated from each other by 0.1454 inches. A gas-permeable membrane is adhered to such a metal support plate, and the holes allow easy transport of oxygen through the membrane. Support plates need to be mechanically rigid to support the membrane, non-cytotoxic to cells through degradation products, and non-degrading in the presence of gas. Typical materials include polymers, plastics (e.g., polycarbonates, PMMA, polystyrene), and metals (e.g., stainless steel, aluminum). Other materials described herein for the manufacture of the cell culturing plates can also be used for the support plate.

Figure 19B:
FIGS. 19A, 19B and 19C are schematic diagrams of a top plate of a two-compartment cell culturing device, including integral spacer elements, in top and end views, respectively.
Figure 19A:
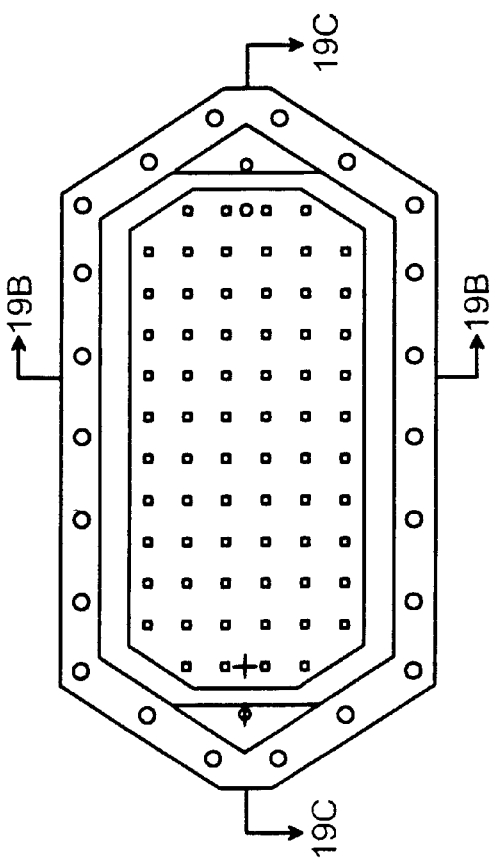
Figure 19C:
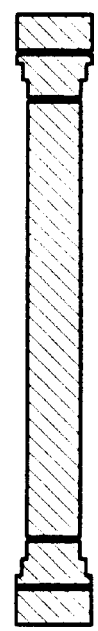

In yet another embodiment, the top plate is machined to include hundreds of spacer elements that are set close enough together to support the gas-permeable membrane without the need for a separate support plate. As shown in FIGS. 19A and 19B, such a plate can include about 70 spacer elements, each about 0.1 inch on a side and spaced about 0.5 inches apart, for a plate having an overall size of 8.5×4.75 inches. The membrane can be adhered to the spacer elements, e.g., with separate adhesive, or by using a sticky membrane, such as the BREATHE-EASY membrane described above. If a non-sticky membrane is used without adhesive, then the membrane must be supported from above and below, e.g., as shown in FIGS. 3B and 3C.

Example 6

Outlet Oxygen Measurements of Porcine Hepatocytes

All experiments including device characterization and calibration were conducted in a warm room at 37° C. Polarographic oxygen electrodes were prepared as per the manufacture's operating instructions. Briefly, the acrylic housing with affixed Teflon membrane was filled with oxygen electrolyte solution. The housing was then inserted onto the oxygen electrode and screwed into the body of the electrode making sure that no air bubbles were trapped near the electrode tip.

A Clark electrode was calibrated at 0 and 159 mmHg partial pressure of oxygen (PO2) prior to outlet oxygen measurements. The 0 mmHg PO2 calibration point was obtained by making a supersaturated solution of sodium sulfite (10% w/v) in deionized water and injecting it into the flow-through housing of the electrode. The 159 mmHg PO2 calibration point was obtained by initiating medium flow at 1.0 mL/min through the calibration circuit in which the medium had been equilibrated with 21% O2 and 10% CO2. This calibration circuit allowed for on-line electrode calibration at any time during the experiments to check for electrode drift. Typically, electrode calibration was performed prior to starting the experiments, at least once during data acquisition, and finally at the conclusion of data collection. In all experiments, the electrode drift was less than 2%.

Prior to connecting the bioreactor to the entire perfusion circuit, the latter was primed with medium and the bioreactor was assembled with a glass slide coated with cultured hepatocytes as described above. In all experiments for outlet PO2 measurement, the initial medium flow rate was set at 1.0 mL/min. To assure adequate development of flow parameters and steady-state outlet PO2 conditions, five mean residence time volumes were allowed to pass through the reactor at each flow rate prior to changing flow rate settings. Steady-state outlet PO2 was confirmed graphically on a computer monitor for each flow rate. The flow rate was then reduced to either 0.5 or 0.6 mL/min. Once a steady-state was achieved, the flow rate was then reset to 1.0 mL/min. In all cases, this outlet PO2 matched the initial outlet PO2 value at 1.0 mL/min to within 10%. For the same glass slide, outlet PO2 was then measured at higher flow rates, starting at a maximum of 3.5 mL/min and decreasing down to 0.1 mL/min.

Figure 20:
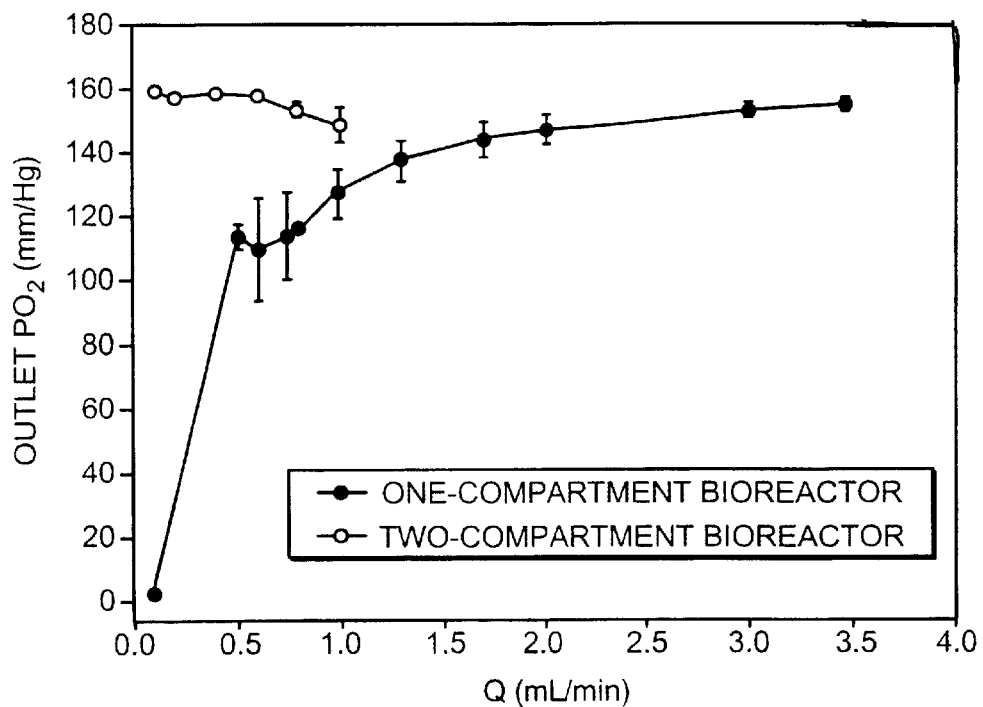
FIG. 20 is a graph of outlet partial pressure of oxygen at varying medium flow rates for single and two-compartment bioreactors.

The graph in FIG. 20 summarizes the effects of media flow rates upon outlet oxygen partial pressure, for both one and two-compartment bioreactors seeded with $2 \times 10^6$ porcine hepatocytes. In the one-compartment bioreactor (which is essentially the same as the two-compartment bioreactor but lacks the gas-permeable membrane), the outlet oxygen tension decreases gradually from what is very close to the inlet tension, with a value of 154.13±1.88 mmHg at a flow rate of 3.5 mL/min to 114.00±4.0 mmHg at a flow rate of 0.5 mL/min, with an approximate overall decrease of 26%. As the flow rate was further decreased to 0.1 mL/min, output oxygen tension precipitously decreases to 2.13±2.46 mmHg, which is 1.4% of the highest flow condition measured.

On the other hand, in the case of the two-compartment bioreactor, the variability of outlet PO2 tension across all flow rates was minimal as compared to that exhibited by the one-compartment bioreactor, with average values ranging from 148.0±5.5 at 1.0 mL/min to 159.5±0.75 at 0.1 mL/min. Flow rates between 0.1 and 1.0 mL/min were selected because of the low oxygen tensions encountered in the one-compartment bioreactor at these flow rates. At the lowest flow rate, the resulting mean output oxygen tension of the two-compartment bioreactor demonstrated a 75-fold improvement over its simpler, single-compartment counterpart ($p<0.000001$).

Statistical significance was also seen between the performances of the two reactors for the 0.5–0.6 mL/min flow range ($p=0.012$), and for the 0.75 to 0.8 flow range ($p=0.015$), as determined by simple one-way ANOVA. There was no statistical difference in the performances of the two bioreactors at 1.0 mL/min. As a result, the single-compartment device can be used for flow rates higher than about 1.0 mL/minute, and smaller scale culturing and organ assist applications.

Example 7

Comparison of Single and Two-Compartment Bioreactor Designs

In a single-compartment design, convection is sufficient at high flow rates to compensate for the high OUR exhibited by porcine hepatocytes. However, with reduction in flow rates to avoid shear stress, the system becomes increasingly dominated by diffusion, and oxygen utilization of cells exceeds the locally available supply. Outlet oxygen tensions can then decrease beneath $K_{0.5}$ values. This shortfall is most apparent at the lowest tested flow rate of 0.1 mL/min, where the system is dominated by diffusion over convection, with a resulting average oxygen tension of 2.13 mmHg. This is less than the mean $K_{0.5}$ value (2.7 mmHg) from Days 2 and 4 post-seeding for porcine hepatocytes (Balis, et al 1999), and is strong evidence for oxygen substrate-limited conditions in the single-compartment bioreactor during sufficiently slow flow conditions.

These results can be generalized to larger bioreactor systems. For example, extracorporeal BAL support of a young adult rat between 200 and 250 grams would have fundamental operating conditions initially derived from total blood volume and resting cardiac output. With typical values of about 17–23 mL and 5 mL/min, respectively, a maximal safe extracorporeal plasmapheresis rate would be 1.0 mL/min, representing 20% of the resting cardiac output. As crossflow plasma separators typically filter at no more than at 20% efficiency, a realistic plasma flow rate would be between 0.1 and 0.2 mL/min, with the former representing a reliable, conservative general case choice.

As the young adult rat liver has between 2 and $4 \times 10^8$ hepatocytes, the minimum number of cells representing the necessary 10% liver biomass for adequate extracorporeal support would be between 20 and 40 million cells. This equates to a BAL design requiring at least $2 \times 10^7$ cells covering 200 cm², assuming a nominal seeding density of $1 \times 10^5$ cells/cm². The results described herein indicate that there are substantial constraints on the ability to change the system to increase oxygenation and maintain high cell function. For example, the OUR of hepatocytes and diffusivity of the device are intrinsic properties that can not be substantially altered. Of the three possible variables (oxygen concentration, cell density, and chamber height H), none can be significantly altered without imposing difficulties.

For example, lowering cell seeding density is undesirable, because it lowers bioreactor efficiency. An increase in inlet oxygen concentration may harm the cells, because higher than ambient oxygen tensions have been shown to be toxic to hepatocytes. Finally, lowering chamber (hydrodynamic) height substantially increases fluid sheer at the cell surface, which is harmful to hepatocytes, and additionally, increases the bioreactor fabrication difficulty.

Thus, for large-scale systems, e.g., bioreactors of biologically relevant size, the effective oxygenation will be inadequate for a single compartment bioreactor, unless the cells are protected from fluid shear and higher medium flow rates are used. The incorporation of an oxygen-permeable membrane is an effective solution to providing adequate oxygen tensions to all cells at low flow rates.

Example 8

Assaying Hepatocyte Viability and Function in the Two-Compartment Bioreactor

Figure 21A:
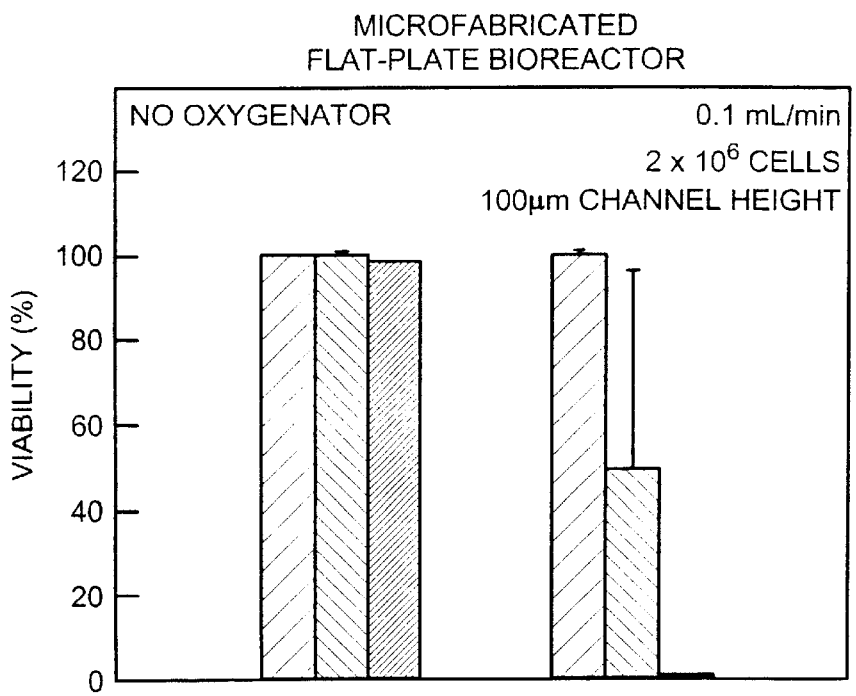
FIGS. 21A and 21B are a pair of graphs illustrating cell viability in single-(21A) and two-compartment (21B) cell culturing devices at zero hours, and after 8 hours.
Figure 21B:
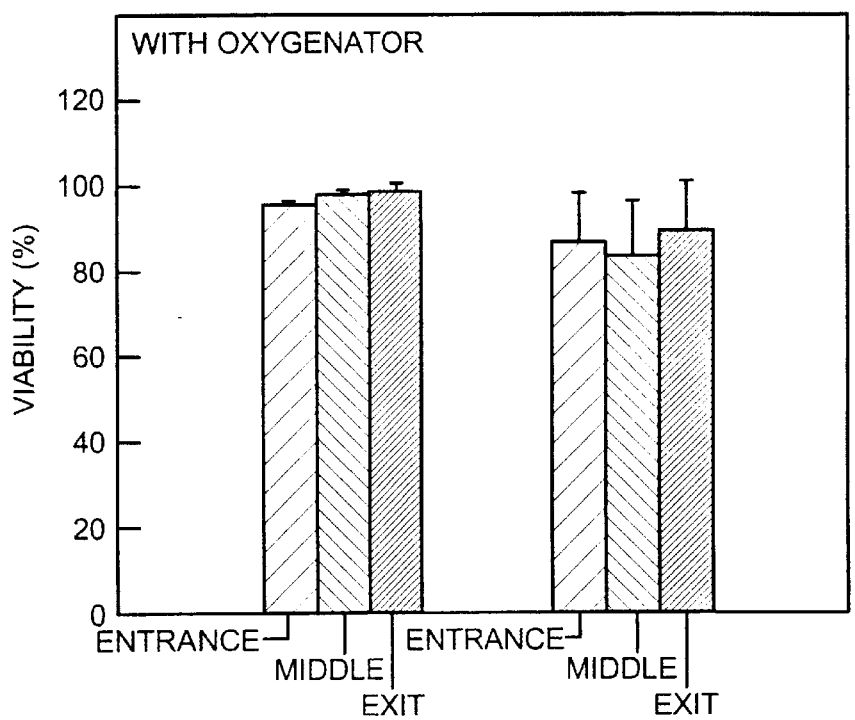

In an attempt to further test the utility of membrane oxygenation, the 2 million cell small device was used to evaluate the effect of the oxygenation membrane on hepatocyte viability and function. As can be seen in FIGS. 21A and 21B, cell viability in the bioreactor decreased dramatically from about 100%, 100%, 100% at the locations in the vicinity of the reactor entrance, middle, and exit to about 100%, 50%, and 0% after 8 hours perfusion with oxygenated (154 mmHg) medium, respectively (FIG. 21A). This result clearly indicates that, as the model predicts, cells at the inlet utilize most of the oxygen in the liquid and thus the down stream cells towards the reactor outlet are oxygen-limited and die. As shown in FIG. 21B, when a membrane oxygenator was added (as described in the FIG. 20), the cells in the reactor with the oxygenator survived over an 8 hour perfusion, with only a slight decrease over time, and little difference between the entrance, middle, and exit.

Figure 22:
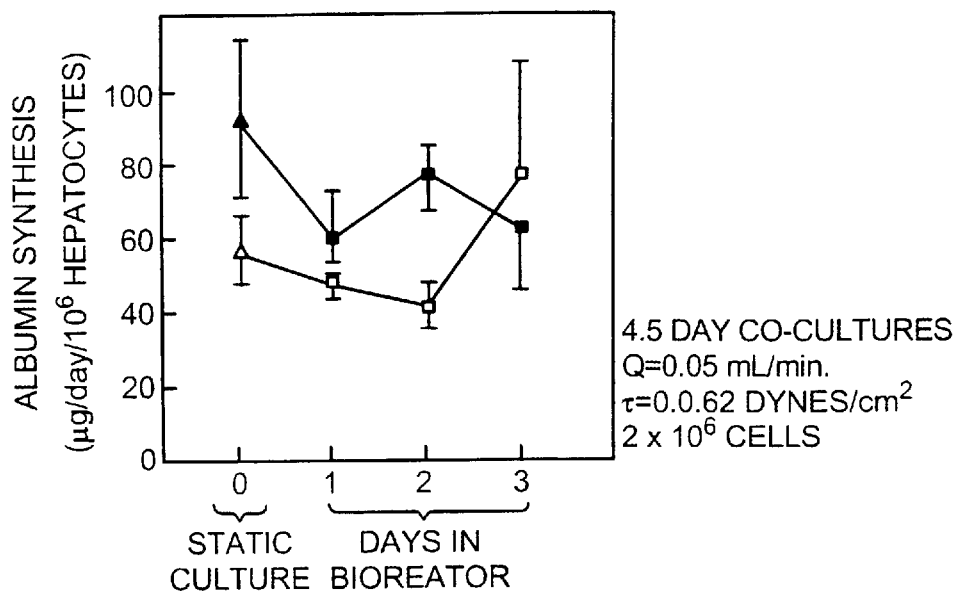
FIG. 22 is a graph illustrating cell function (as measured by albumin synthesis) in two separate experiments in a two-compartment bioreactor.

Next, the beneficial effect of the membrane oxygenator was tested on long-term hepatocyte specific function. After culturing 2 million hepatocytes under static culture for 5 days to get the cells to achieve a stable level of function, the cells were placed into a reactor with the membrane oxygenator and cultured them for an additional 3 days at a flow rate of 0.05 mL/min. As can be seen in FIG. 22, cells remained functioning in the membrane oxygenator reactor during the perfusion culture. Results were repeated in 2 different experiments. Since cells died in 8 hours in the absence of the membrane oxygenator there was no need to perform similar function experiments of the reactor with no membrane.

These two sets of experiments clearly indicate that cells become oxygen-limited in even a small 2 million cell reactor in the absence of an internal oxygenator. On the other hand, the addition of an internal oxygenator provides adequate oxygenation to cells, and proves the principal of the two-compartment bioreactor.

Example 9

Long-Term Function of Hepatocyte Co-Cultures in a Microchannel Bioreactor With An Internal Membrane Oxygenator In the previous example, a flat-plate microchannel bioreactor demonstrated that, in the absence of internal membrane oxygenation, oxygen limitations occurred at a low medium flow rate whereas no oxygen limitations occurred in the bioreactor with the internal membrane oxygenator for the same medium flow rate.

The present study evaluated the viability and synthetic function of rat hepatocytes in microchannel, flat-plate bioreactors with and without internal membrane oxygenation, varying flow rates and bioreactor channel heights to test the effects of various wall shear stresses.

Reagents and Solutions

Dulbecco's Modified Eagle's Medium (DMEM, with 25 mM glucose and 4 mM glutamine), fetal bovine serum (FBS), ethylenediaminetetraacetic acid (EDTA), phosphate buffered saline (PBS), penicillin, streptomycin, and trypan blue solution were purchased from Life Technologies (Gaithersburg, Md.). Hydrocortisone was obtained from Abbott Laboratories (North Chicago, Ill.), epidermal growth factor (EGF) was obtained from Collaborative Research (Bedford, Mass.), and glucagon was obtained from Eli Lilly and Co. (Indianapolis, Ind.). Insulin was obtained from Novo Nordisk A/S (Bagsuaerd, Denmark), bovine calf serum (BCS) was obtained from JRH Biosciences (Lenexa, Kans.), collagenase was obtained from Sigma Chemical Company (St. Louis, Mo.) and trypsin was obtained from ICN Biomedicals (Costa Mesa, Calif.). Calcein acetoxymethyl ester (calcein-AM) ethidium homodimer-1 and Hoechst 33258 DNA stain were purchased from Molecular Probes (Eugene, Oreg.).

Hepatocyte culture medium for experiments consisted of DMEM supplemented with 10% (v/v) FBS, 200 U/mL penicillin, 200 µg/mL streptomycin, 7.5 µg/mL hydrocortisone, 20 ng/mL EGF, 14 ng/mL glucagon, and 0.5 U/mL insulin. Fibroblast culture medium consisted of DMEM supplemented with 110 mg/L sodium pyruvate, 10% BCS, 200 U/mL penicillin and 200 µg/mL streptomycin. The pH of the culture mediums, when equilibrated with air containing 10% $CO_2$, was 7.4. Gas mixtures were obtained from BOC Gases (Hingham, Mass.), and gas compositions were certified to be accurate to within 0.05 mmHg.

Hepatocyte Isolation and Culture

Hepatocytes were isolated from 2–3 month-old female Lewis rats (Charles River Laboratories, Wilmington, Mass.) weighing 180–200 g, by a modified procedure of Seglen, Methods Biol., 13:29–83 (1976), and was previously described by Dunn et al., Biotechnology Progress, 7:237–245 (1991). Approximately 200–300 million hepatocytes were collected in a single isolation, with cell viabilities ranging between 85% and 95%, as determined by trypan blue exclusion. Nonparenchymal cells, as judged by their size (less than 10 µm in diameter) and morphology (nonpolygonal or stellate) were less than 1% of the isolated cells.

NIH 3T3-J2 Fibroblast Culture

NIH 3T3-J2 fibroblasts were cultured at 37° C. in 175 $cm^2$ tissue culture flasks (Fisher, Springfield, N.J.) equilibrated in a humidified atmosphere with 10% $CO_2$/90% air. The cells were typically grown to preconfluence and passaged by trypsinization in 0.01% trypsin /0.01% EDTA solution in PBS for 5 minutes at 37° C. The cell suspension was diluted 1:1 with fibroblast culture medium and centrifuged at 800 RPM for 5 minutes. After aspiration of the supernatant, the pellet was resuspended in fibroblast culture medium and approximately 10% of the cells were inoculated into each fresh tissue culture flask. Cells were passaged at preconfluency no more than 12 times.

Substrate Preparation

Hepatocyte monolayers and co-cultures were performed on 25×75 mm glass slides as described in Example 5.

For the viability experiments, which used glass slides cultured with hepatocyte monolayers, the glass slides were seeded with $2 \times 10^6$ hepatocytes in 2 mL of hepatocyte culture medium and incubated at 37° C. After 1 hour, the medium was aspirated and another 2 mL of the above suspension was placed on the slide. After 24 hours, the glass slides were removed from their PDMS seeding inserts and placed in new P-100 dishes with 5 mL of fresh hepatocyte culture medium. This double seeding allowed for a confluent monolayer of hepatocytes to be achieved.

For the co-culture experiments for synthetic function, the glass slides were seeded with $0.5 \times 10^6$ hepatocytes in 2 mL hepatocyte culture medium and incubated at 37° C. The following day, fibroblasts were trypsinized, counted on a hemocytometer, and suspended in fibroblast culture medium at a concentration of $0.375 \times 10^6$ cells/mL. Two mL of the fibroblast suspension was placed on each hepatocyte-seeded slide after removal of the previous day's medium. Twenty four hours later, the glass slides were removed from their PDMS seeding inserts and each slide was placed in a new P-100 tissue culture dish with 5 mL of fresh hepatocyte culture medium. The culture medium (5 mL) was subsequently replaced daily for each slide. Glass slides that were used for controls remained in the P-100 dishes throughout the duration of the experiments. Typically, glass slides were placed into the bioreactors on days 4 or 5 post-isolation. Medium sampling occurred daily starting two days prior to placement into the bioreactor, i.e., while the slides were in non-perfused conditions in P-100 dishes, and occurred daily for the duration of the experiment.

Flat-Plate Microchannel Bioreactor Designs

The bioreactor with an internal membrane oxygenator used in these experiments is described in Example 5. The bioreactor without an internal membrane oxygenator was constructed in essentially the same manner as the bioreactor with an internal membrane oxygenator, with the exception being the use of an impermeable upper plate in the former.

The actual flow channel height of each bioreactor (with and without internal membrane oxygenator) was measured on an inverted microscope equipped with a digital indicator capable of 1 $\mu$m resolution. The focusing knob of the microscope was rotated so that the focal plane of a scribed mark on the top surface of a glass slide in the assembled position was brought into focus and the digital indicator was set to zero. The focusing knob was then rotated further in the same direction so that a scribed mark on the undersurface of the glass window of the upper plate was just brought into focus. The reading on the digital indicator was the height of the channel in microns. Reported channel heights are the average of three locations along the length of the glass slide within a bioreactor. Typically, the measurements along the length of the channel varied by less then 20%.

Flow Circuit Apparatus

The flow circuit used in the experiments using the bioreactor without the internal membrane oxygenator consisted of a reservoir containing medium which was pumped through #13 Masterflex silicone tubing by a digital variable-speed peristaltic pump drive (Masterflex L/S, Cole-Parmer, Vernon-Hills, Ill.). The medium then flowed to an external shell and tube gas exchanger, consisting of 8 meters of SILASTIC® tubing (I.D. 0.50 mm and O.D. 0.94 mm) (Konigsberg Instruments, Inc., Pasadena, Calif.), for equilibration with 21% $O_2$ and 10% $CO_2$. It then entered a bubble trap, which was connected to the bioreactor inlet. Upon exiting the outlet port of the bioreactor, the medium flowed back into the reservoir for recirculation.

In experiments using the bioreactor with the internal membrane oxygenator, the flow circuit was identical to the one described above with the exception of the external gas exchanger. In these experiments, the external gas exchanger was removed from the flow circuit and oxygenating gas flow was established through the chamber above the internal membrane of the bioreactor itself. All pump drives used in these experiments were calibrated for volumetric flow rates according to manufacturer's instructions. Medium samples were obtained daily from the reservoir and the total volume of the flow circuit was replaced daily with fresh medium.

All experiments were conducted in a warm room at 37° C. Prior to connecting the bioreactor to the entire perfusion circuit, the latter was primed with medium and the bioreactor was assembled containing a glass slide with either a monolayer of cultured hepatocytes (for viability studies) or co-cultures of hepatocytes and 3T3-J2 fibroblasts (for function studies) as described above.

Albumin and Urea Assays

Media samples were collected daily and stored at 4° C. for subsequent analysis of albumin and urea content. Albumin secretion rates were measured by enzyme-linked immunosorbent assays (ELISA), as described by Dunn et al. (1991) *Biotechnology Progress* 7:237–245. Rat albumin and anti-rat albumin antibodies were purchased from Cappel Laboratories (Aurora, Ohio). Urea synthesis was analyzed with a commercially available assay kit (Sigma Diagnostics, St. Louis, Mo.).

DNA Measurement

Glass slides with attached fibroblasts and/or hepatocytes were incubated with 0.1% (w/v) type 4 collagenase in Kreb's Ringers Buffer at 37° C. for 30 min, to release the cell layer from the underlying substrate. The suspension was centrifuged for 5 minutes at 1200 g and the resulting pellet was resuspended in 2 mL of PBS. Samples were stored at −80° C. until DNA analysis. The cell pellets were washed twice with PBS and resuspended in 1 mL of sodium dodecyl sulfate (SDS) buffer (0.1% SDS, 1 mM EDTA, and 100 mM Tris, pH 7.4). The cell suspension was incubated at room temperature overnight. Samples (40 $\mu$L) were alliquoted in triplicate into 96-well microtitre plates along with DNA standards (prepared from calf thymus DNA) between 0 and 100 $\mu$g/mL. Salt/dye buffer (1 mM EDTA, 2 M NaCl, and 10 mM Tris, and 1.6 $\mu$M Hoechst 33258) was added to each well and the plate was incubated in the dark at room temperature for 30 minutes prior to reading on a fluorescence plate reader (Molecular Devices, San Luis Capistrano, Calif.) with excitation and emission frequencies of 360 and 460, respectively.

To quantify the initial numbers of hepatocytes and fibroblasts present on a slide, 10 slides seeded with hepatocytes and 10 slides seeded with co-cultures of hepatocytes and fibroblasts were analyzed for DNA. For initial number of hepatocytes, hepatocytes were seeded onto glass slides treated with collagen as described above. Twenty four hours after seeding, hepatocytes were harvested by scraping the surface of the slide, followed by rinsing thrice with phosphate-buffered saline (PBS). For total number of cells, hepatocytes were seeded onto the glass slides and 24 hours later, fibroblasts were seeded. The following day, these slides were harvested by scraping the cells from the surface.

Viability Assay

Viability was measured using a live/dead staining assay with calcein AM and ethidium homodimer. Stock solutions (1 mM in dimehtylsulfoxide) of each dye were diluted in hepatocyte culture medium for a final concentration of 5 $\mu$M. Viability of hepatocytes at 0 and 8 hours of perfusion was obtained by taking phase contrast and fluorescent images to determine total and live/dead cell numbers per field of view, respectively. Viabilities are reported in percent and are the average number of living cells in three microscope fields at each position (entrance (10 mm downstream from inlet), middle (37 mm from inlet), and exit (10 mm upstream from outlet)).

Statistical Analysis

Experiments for synthetic function rates at specific wall shear stresses and microchannel heights were conducted in duplicate or triplicate. These rates were then averaged across replicate runs. Values are reported as means±standard deviations (run to run). Statistical analysis of data was performed using Lotus 1-2-3 (Lotus Development Corporation, Cambridge Mass.) and SigmaStat (SPSS, Inc., San Rafael, Calif.), and subsequently plotted with SigmaPlot (SPSS, Inc., San Rafael, Calif.). Statistical significance of difference in means was assessed by use of ANOVA, with p values of less than 0.05 being considered significant.

Figure 23A:
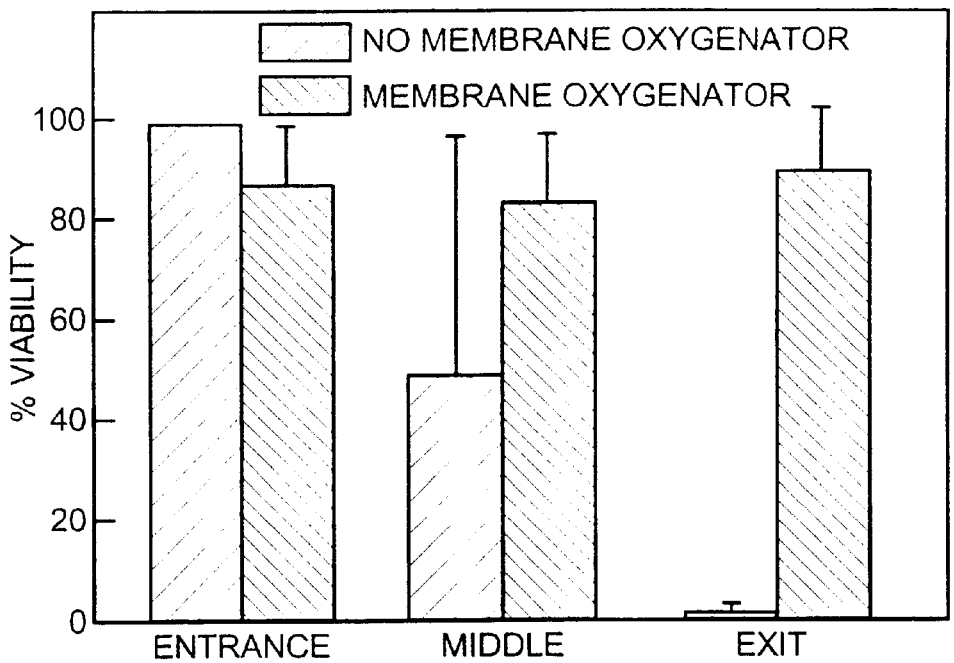
FIG. 23A is a graph of the viability of hepatocytes cultured at the entrance (left), middle (center), and exit (right) of a bioreactor with or without an internal membrane oxygenator.

Comparison of Microchannel Bioreactors With and Without An Internal Membrane Oxygenator To characterize the effect of the internal membrane oxygenator, a series of experiments were conducted that assessed and compared the viability of rat hepatocytes cultured as monolayers ($2.0 \times 10^6$ hepatocytes/collagen treated glass slide) within the flat-plate microchannel bioreactors with and without the internal oxygenator. The medium volumetric flow rates were set at 0.1 mL/min and the bioreactor channel heights were maintained at 100 $\mu$m, resulting in a wall shear stress of 0.4 dynes/cm². Phase contrast photomicrographs were prepared with superimposed fluorescence visualization to indicate dead hepatoycytes located at the entrance (2 cm from entrance), middle (5 cm from entrance), and exit (2 cm from exit) positions in both bioreactor configurations after 8 hours of continuous perfusion. Most of the hepatocytes were non-viable in the bioreactor without the internal membrane oxygenator at the middle and exit positions. In the bioreactor with the internal membrane oxygenator, most of the cells were viable at all three locations within the bioreactor. These results are quantitated in FIG. 23A, which shows that, at 8 hours in the bioreactor without the internal membrane oxygenator, the viability at the entrance position (left) remained greater than 98% but dropped to 48% at the middle position (center). At the exit position (right), there were no viable cells at 8 hours and many had detached from the glass slide. For the bioreactor with the internal membrane oxygenator, the viabilities at 8 hours were greater than 85%, 82%, and 87% at the entrance (left), middle (center), and exit (right) positions, respectively (FIG. 23A).

Figure 23B:
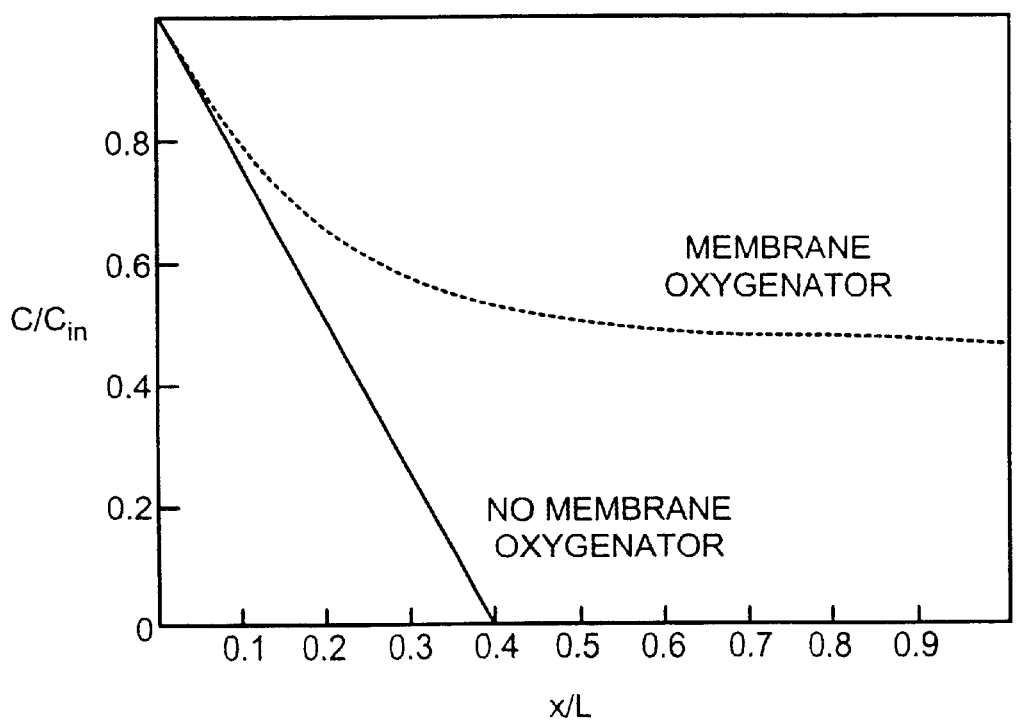
FIG. 23B depicts the predicted outlet oxygen tension along the channel length in a bioreactor with and without an internal membrane oxygenator.

These findings correlate with the results of a mathematical model for predicting outlet oxygen tension in each bioreactor configuration (FIG. 23B). In the bioreactor without the internal membrane oxygenator, the model predicts that hepatocytes would be oxygen depleted starting at approximately 40% of the nondimensionalized channel length (solid line). The model also predicts that the bioreactor with the internal membrane oxygenator would supply sufficient oxygenation throughout the entire channel length (dashed line).

The viability results from this study are consistent with the findings from studies using porcine hepatocytes, which showed that at a volumetric flow rate of 0.1 mL/min/$2 \times 10^6$ hepatocytes, which is a conservative upper limit for extracorporeal plasma flow, the outlet oxygen tension ($PO_2$) in the bioreactor without the internal membrane oxygenator fell below oxygen limiting levels ($K_{0.5}$) for the hepatocytes. In the bioreactor with the internal membrane oxygenator, the outlet $PO_2$ remained essentially equivalent to the inlet $PO_2$ for volumetric flow rates ranging from 0.1 to 1.0 mL/min.

Figure 24:
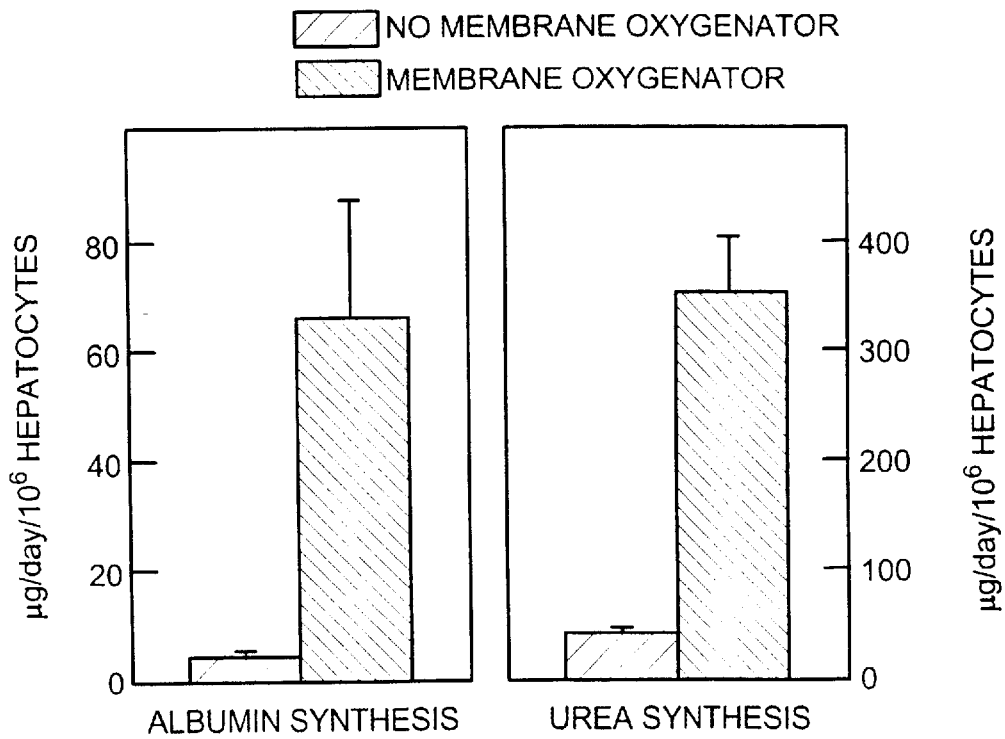
FIG. 24 is a graph of albumin and urea synthesis on day 3 by rat hepatocytes co-cultured with 3T3-J3 fibroblasts in bioreactors with or without an internal membrane oxygenator.

To assess the effect of internal membrane oxygenation on the function of hepatocytes within the two bioreactor configurations, albumin and urea synthesis rates of rat hepatocytes seeded on collagen coated glass slides co-cultured with 3T3-J2 murine fibroblasts were measured in the bioreactor with and without the internal membrane oxygenator. Volumetric flow rates were maintained at 0.06 mL/min in each of the bioreactors. The channel height for the bioreactor without the internal membrane oxygenator was 130 $\mu$m with a corresponding wall shear stress of 0.14 dynes/cm² and the channel height of the bioreactor with the internal membrane oxygenator was 115 $\mu$m with a corresponding wall shear stress of 0.18 dynes/cm². FIG. 24 shows the albumin (left) and urea (right) synthesis rates on day 3 of perfusion within the two bioreactors. The albumin synthesis rate (left) for the bioreactor without the internal membrane oxygenator was 4.75 $\mu$g/day/$10^6$ hepatocytes and was 65.86 $\mu$g/day/$10^6$ for the bioreactor with the internal membrane oxygenator. The urea synthesis rate (right) was 38.71 $\mu$g/day/$10^6$ in the bioreactor without the internal membrane oxygenator and was 347.16 $\mu$g/day/$10^6$ in the bioreactor with the internal membrane oxygenator. This corresponds to an increase of greater than 1300% in the albumin synthesis rate and an increase of greater than 500% in the urea synthesis rate within the bioreactor with the internal membrane oxygenator as compared to the bioreactor without the internal membrane oxygenator.

Figure 25A:
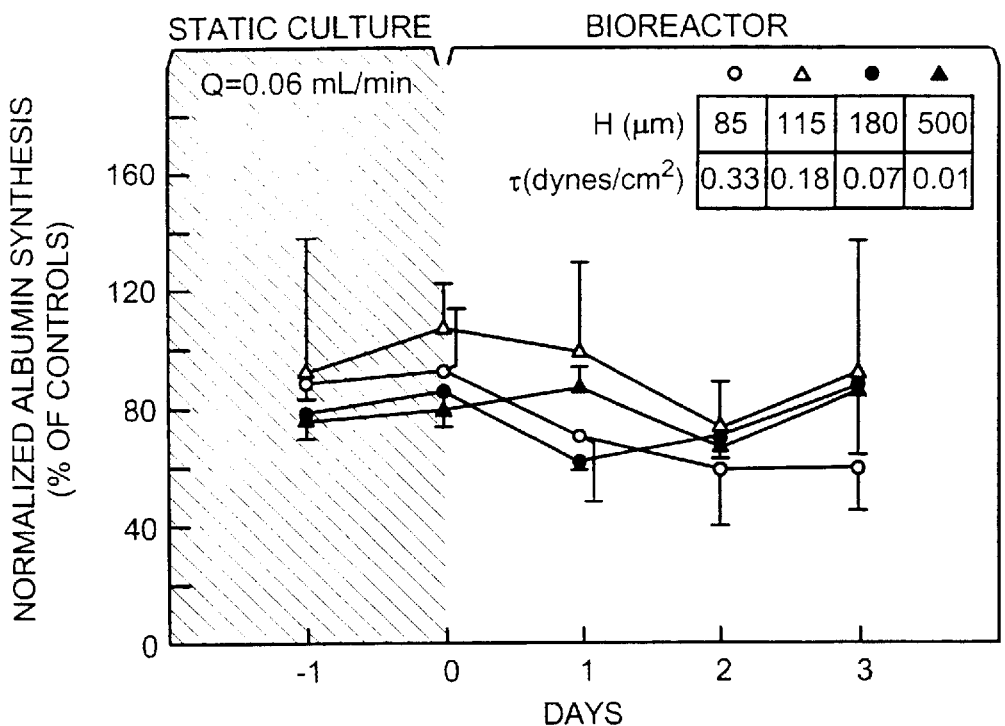
FIGS. 25A and 25B are graphs of normalized albumin synthesis at low (A) and high (B) shear stress by rat hepatocytes co-cultured with 3T3-J2 fibroblasts in a bioreactor with an internal membrane oxygenator.
Figure 25B:
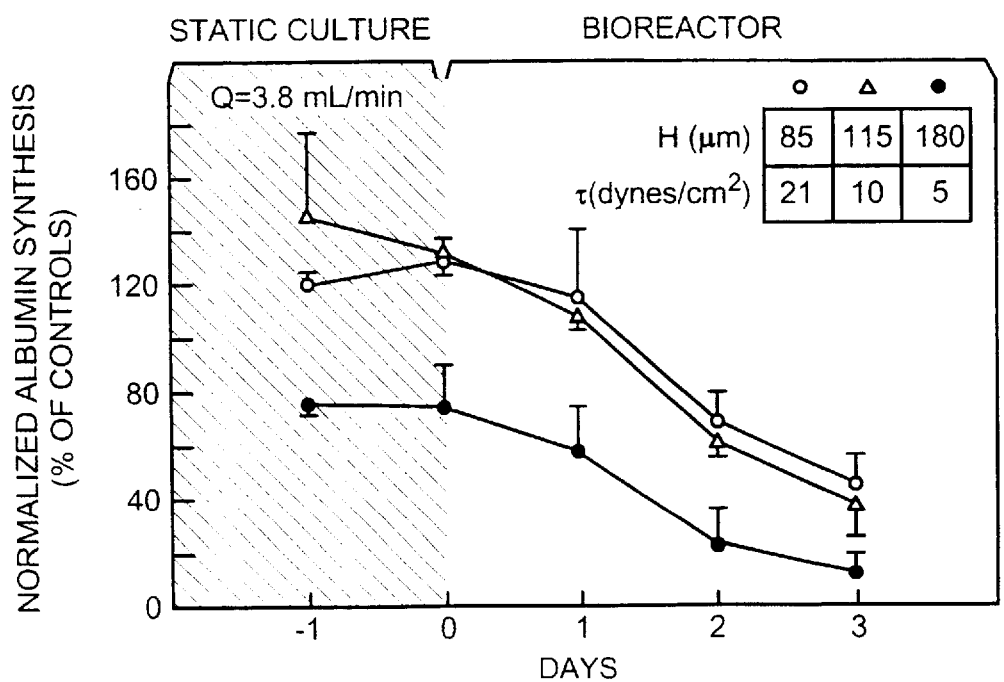
Figure 26A:
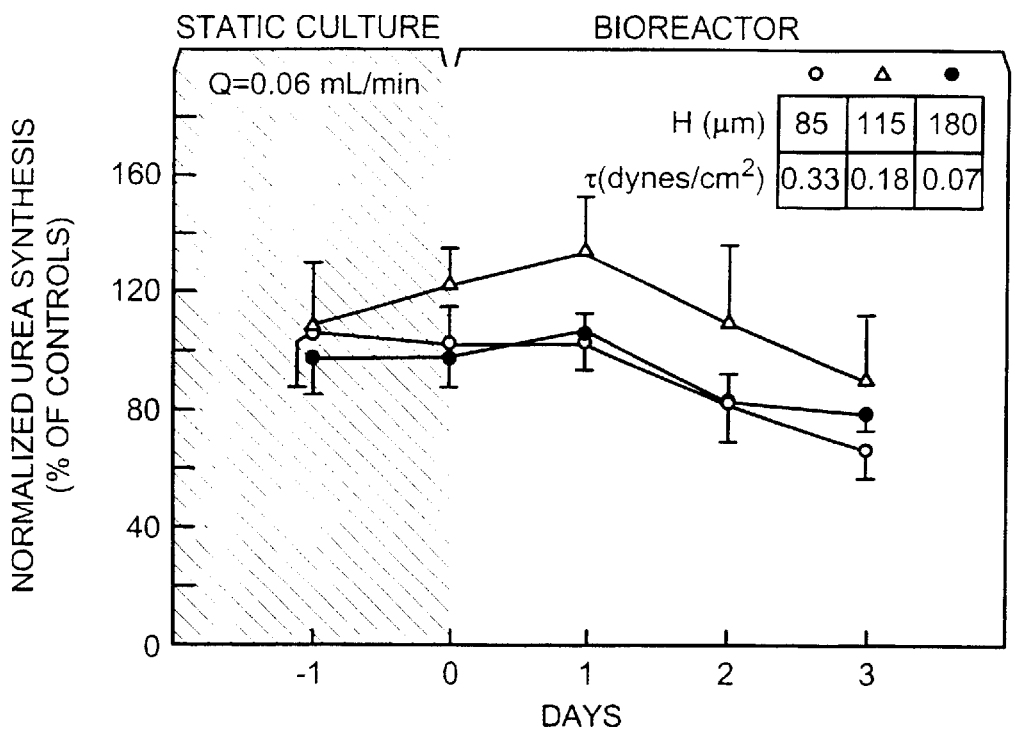
FIGS. 26A and 26B are graphs of normalized urea synthesis at low (A) and high (B) shear stress by rat hepatocytes co-cultured with 3T3-J2 fibroblasts in a bioreactor with an internal membrane oxygenator.
Figure 26B:
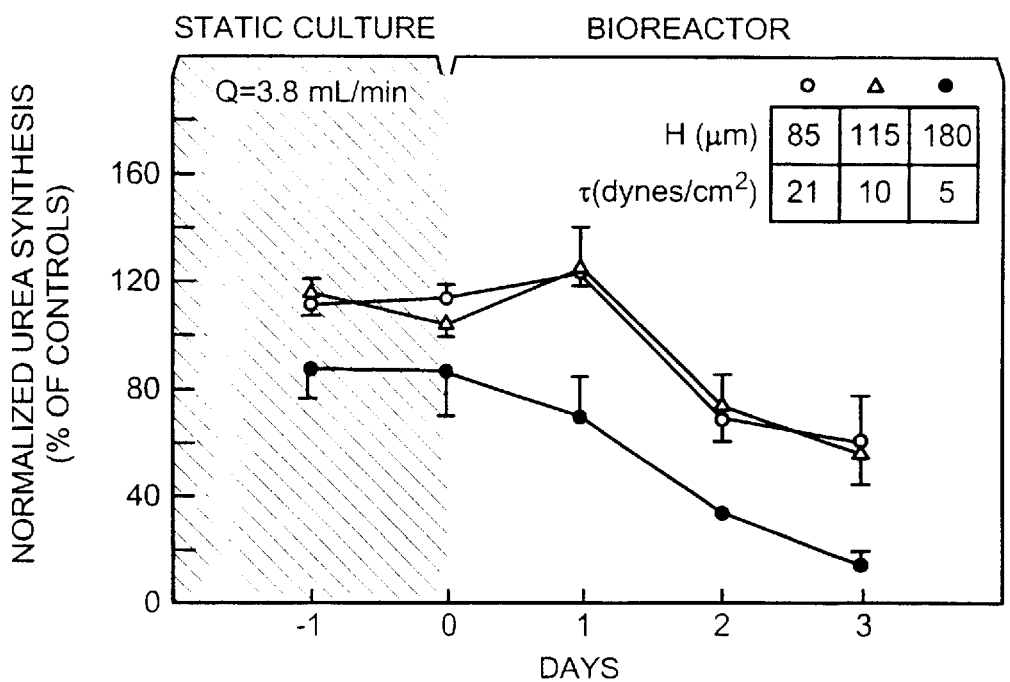

Effect of Flow Conditions on Hepatocyte Function in Bioreactors With An Internal Membrane Oxygenator Experiments to determine the effects of various flow conditions were conducted in the bioreactor with the internal membrane oxygenator. The flow rate (mL/min)—channel height ($\mu$m) combinations used to asses the effect of flow conditions on the function were: 0.06—85, 0.06—115, 0.06—180, 0.06—500, 4.18—180, 3.46—115, and 3.82—85, which corresponded to wall shear stresses of 0.01, 0.07, 0.18, 0.33, 5, 10, and 21 dynes/cm², respectively. In order to evaluate the effect of shear stress, a low shear stress group (0.01–0.33 dynes/cm²) and a high shear stress group (5–21 dynes/cm²) were formed. FIGS. 26A and 26B show the results of daily albumin synthesis rates, presented as percentages of the corresponding daily static controls, at both the low (FIG. 25A) and high (FIG. 25B) shear stresses. For flow conditions that resulted in low shear stresses (FIG. 25A), the normalized daily albumin synthesis rates were not significantly different throughout the three days in the bioreactors across the four shear stresses tested (ANOVA, p=0.12). There also were no statistical differences between the normalized daily albumin synthesis rates for day 3 and day 0 (non-perfused, prior to placement into bioreactor) across any of the four shear stresses. For flow conditions that resulted in high wall shear stresses (FIG. 25B), the normalized daily albumin synthesis rates decreased throughout the three days in the bioreactor for the three wall shear stresses tested (ANOVA, p<0.01). Across the group, the day 3 normalized daily albumin synthesis rates were statistically lower than those on day 0 (Tukey's test, p<0.05).

Figure 27A:
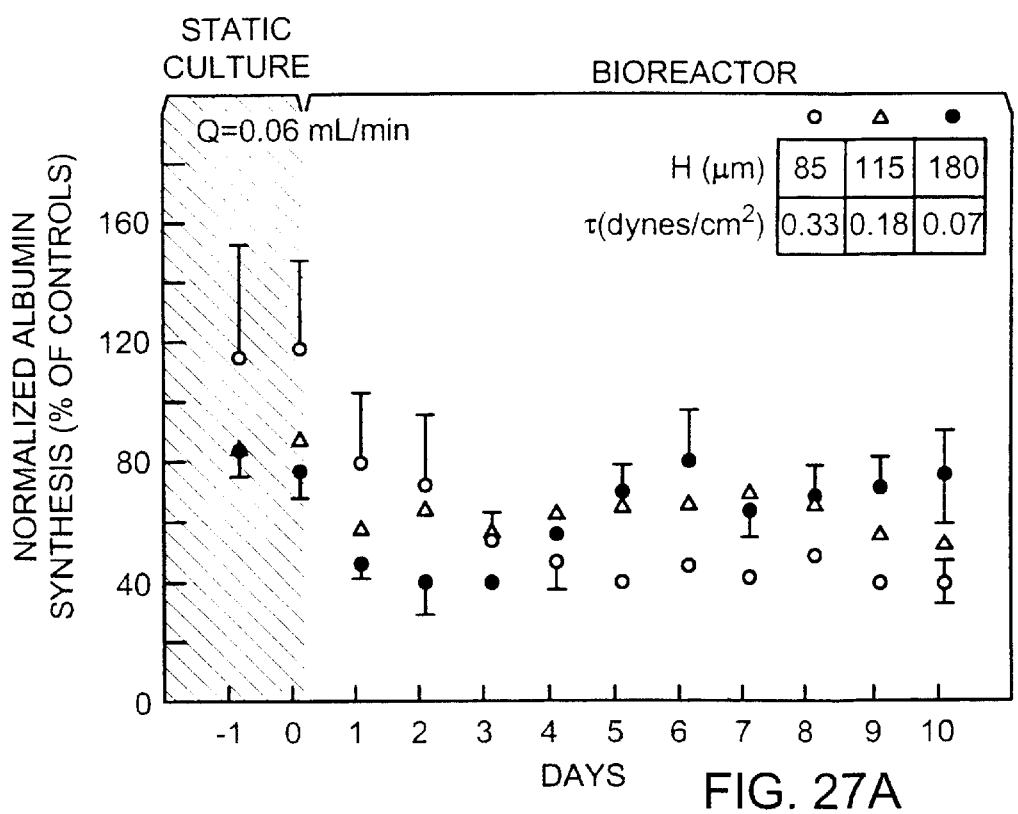
FIGS. 27A and 27B are graphs of albumin (A) and urea (B) synthesis by rat hepatocytes co-cultured with 3T3-J2 fibroblasts for ten days of continuous perfusion in a bioreactor with an internal membrane oxygenator.
Figure 27B:
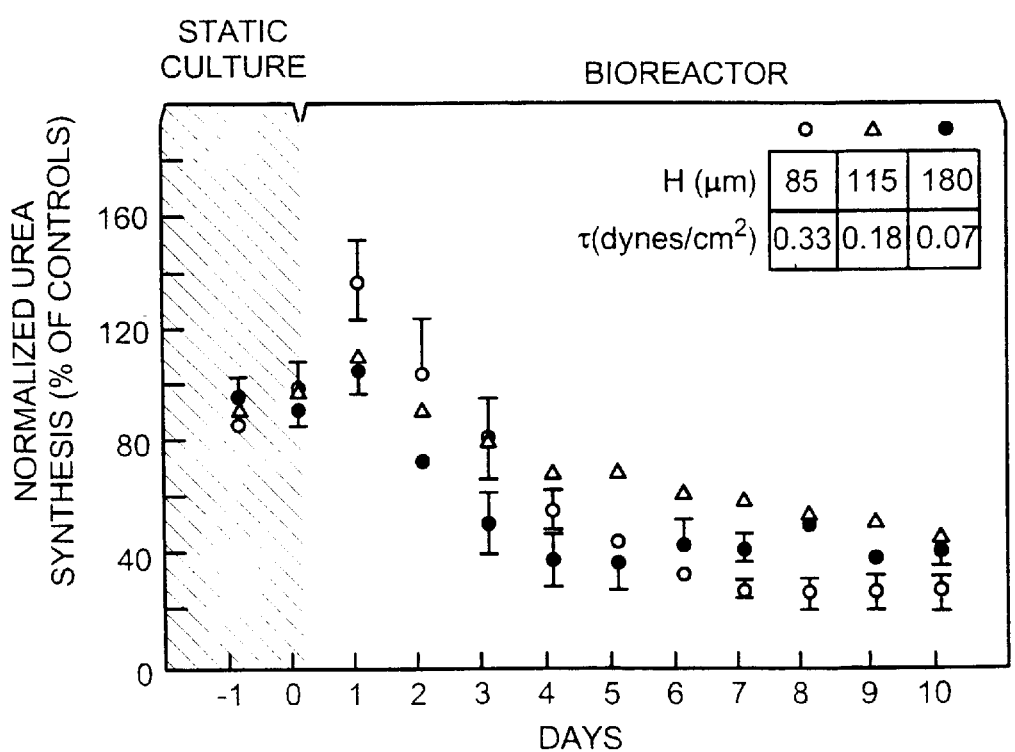

Urea synthesis rates decreased throughout the three days of perfusion in both the low and high shear stress groups (ANOVA, p<0.05) (FIGS. 27A and 27B). In the high shear stress group (FIG. 26B), there was also a statistically significant decrease in the normalized daily urea synthesis rates on day 3 compared to day 0, whereas in the low shear stress group (FIG. 26A), there were no statistically significant differences between day 3 and day 0 urea synthesis rates (Tukey's test, p<0.05). Comparison of day 3 results between low and high shear stress groups showed that albumin and urea production rates were 2.6 and 1.4 times greater, respectively, in the low shear stress group as compared to the high shear stress group (t-Test, p<0.01).

Long-Term Bioreactor Function

To assess the effect of long term perfusion on the synthetic function of rat hepatocytes co-cultured with 3T3-J2 fibroblasts, experiments were conducted for 10 days duration using the bioreactors with internal membrane oxygenator. Volumetric flow rates were set at 0.06 mL/min and channel heights of 85 µm (0.33 dynes/cm$^2$), 115 µm (0.18 dynes/cm$^2$), and 180 µm (0.07 dynes/cm$^2$) were used, corresponding to the low shear stress group. FIGS. 28A and 28B show the daily albumin and urea synthesis rates, presented as percentages of the corresponding daily static controls, for the 10 days of continuous medium perfusion. Albumin synthesis was shown to remain stable throughout the 10 days of perfusion (FIG. 27A) (ANOVA, p=0.08). There was also no statistical difference between the normalized albumin synthesis rates for day 10 and day 0 (static condition, prior to placement into bioreactor) (FIG. 28A). Urea synthesis rates declined during perfusion in the bioreactors, but remained stable from day 4 to day 10 (Tukey's test, p>0.05) (FIG. 27B).

These experiments show that the bioreactor without an internal membrane oxygenator resulted in significantly decreased viability and function of hepatocytes, whereas the hepatocytes in the bioreactor with the internal membrane oxygenator were able to maintain their viability and function. The shear stress calculations showed that at lower wall shear stresses (0.01–0.33 dynes/cm$^2$), hepatocyte functions, measured as albumin and urea synthesis rates, were as much as 2.6 and 1.9 times greater, respectively than those at higher wall shear stresses (5–21 dynes/cm$^2$). Stable albumin and urea synthesis rates were also demonstrated in the bioreactor with internal membrane oxygenator.

Example 10

Enhanced Oxygenation in a Membrane Based Bioartificial Liver Reactor

Oxygen transfer to cultured hepatocytes in membrane based bioartificial liver (BAL) reactor microchannels was investigated with a mathematical model. Models presented in previous examples were based on reactors lacking an internal membrane oxygenator. The consumption of oxygen by hepatocytes is assumed to follow Michaelis-Menten kinetics. Three important dimensionless numbers influence the oxygen gradients formed within the reactor: (1) the membrane Sherwood (Sh) number, defined as the ratio of mass transfer by permeation to mass transfer by diffusion of molecular oxygen (Sh=σH/D$_z$); (2) the Damkohler (Da) number, defined as the relative importance of reaction rate to diffusion (Da=(V$_m$H)/(D$_z$C$_{in}$)); and (3) the Peclet (Pe) number, defined as the relative importance of convective flow to diffusion (Pe=U$_a$H/D$_z$). The Reynolds number is defined as the relative importance of inertial forces to viscous forces (Re=U$_a$H/ν).

This study employed a fixed Damkohler number (=0.11, corresponding to rat hepatocytes) and low Peclet numbers (<50) to highlight the effect of two parameters, the membrane Sherwood number and the gas phase oxygen partial pressure.

Model Formulation

The physical system depicted in FIG. 1C comprises a Newtonian fluid undergoing pressure (P) driven flow between two flat plates in a positive x direction. The steady state continuity and momentum conservation equations (neglecting inertia) are (Batchelor (1967) An Introduction to Fluid Dynamics, Cambridge University Press):

$$\nabla \cdot \tilde{U}=0,$$

$$\mu m \nabla \cdot (\nabla \tilde{U}) = \nabla P \qquad (16)$$

subject to the no-slip boundary condition. The fully developed velocity profile is that of Poiseuille flow (Batchelor supra):

$$\tilde{U} = \tilde{i} 6 U_a \bar{z}(1-\bar{z}) \qquad (17)$$

where, U$_a$ is the average velocity and $\bar{z}$=z/H. The special feature of this problem is that the length (L) of the channel is much larger than its height (H) or L/H>>1. The lower plate contains a monolayer of hepatocytes, while the upper plate is permeable to oxygen (permeability σ). The distribution of oxygen within the reactor is obtained from the solution of the mass conservation equation at steady state (Probstein (1989) Physiochemical Hydrodynamics, Butterworth Publishers)

$$\nabla \cdot \tilde{J}=0 \qquad (18)$$

where, $$\tilde{J} = \tilde{U}C - \underline{\underline{D}} \cdot \tilde{\nabla} C \qquad (19)$$

with, C(x,z) as oxygen concentration and the gradient operator defined in cartesian coordinates as $$\tilde{\nabla} = \tilde{i}\frac{\partial}{\partial x} + \tilde{k}\frac{\partial}{\partial z}.$$

The translational diffusion dyadic for oxygen is $$\tilde{\tilde{D}} = \tilde{i}\tilde{i}D_x + \tilde{k}\tilde{k}D_z.$$

The boundary conditions are derived from: a) constant oxygen concentration (C$_{in}$) at inlet; b) a Danckwerts boundary condition at the reactor outlet; c) Michaelis-Menten kinetics of oxygen uptake by hepatocytes; and d) constant gas phase partial pressure of oxygen.

$$C(0,z)=C_{in} \qquad (20)$$

$$\frac{\partial C(L,z)}{\partial x} = 0 \qquad (21)$$

$$D_z \frac{\partial C(x,0)}{\partial z} = \frac{V_m C(x,0)}{K_m + C(x,0)} \qquad (22)$$

$$D_z \frac{\partial C(x,H)}{\partial z} = \sigma[C_g - C(x,H)] \qquad (23)$$

Numerical Simulation

Equations (16)–(23) were solved in nondimensional form. The Galerkin finite element code (FIDAP, Fluid Dynamics International, Evanston, Ill. 06020 (1993)) implemented nine-node quadrilateral elements and biquadratic interpolating functions for the velocities and concentrations. As convergence criteria, the Euclidean norm ratios of both the solution and residual vectors were required to be less than 10$^{-5}$. Grid optimization was carried out by increasing the number of nodes until the relative concentration change at each node decreased to 0.1 percent.

Diffusion Solution

For the case of Peclet numbers (Pe)<<L/H, the oxygen transport problem may be simplified to 1 dimensional (z directed) diffusion subject to boundary conditions, Eqn.(22) and Eqn.(23). The dimensionless cell surface oxygen concentration may then be written as:

$$\overline{C} = \frac{1}{2}\left\{(\overline{C}_g - \overline{K}_m) - \left(\frac{Da}{Sh}\right)(1 + Sh) \pm \sqrt{\left[\left(\frac{Da}{Sh}\right)(1 + Sh) - (\overline{C}_g - \overline{K}_m)\right]^2 + 4\overline{C}_g\overline{K}_m}\right\} \quad (24)$$

The concentrations are made dimensionless by $C_{in}$. Our numerical calculations were verified against the diffusion solution at low Peclet numbers.

Zero Order Oxygen Flux

For the simple case of uniform flow (constant velocity) in the positive x direction and only diffusive mass transport in the z direction, an analytical solution may be obtained assuming constant uptake of oxygen by the cells. The dimensionless concentration distribution of oxygen within the reactor is then (Carslaw and Jaeger, *Conduction of Heat in Solids*, Oxford University Press (1959)):

$$\overline{C}(x, z) = \overline{C}_g - Da + zDa - \frac{Da}{Sh} + \sum_{n=1}^{\infty} B_n \cos(\lambda_n z)\exp\left[-\frac{L\lambda_n^2 \overline{x}}{HPe}\right] \quad (25)$$

where $\lambda_n$ are roots of the transcendental equation tan $$(\lambda_n) = \frac{Sh}{\lambda_n}; \text{ and } B_n = \frac{4Da(1 - \cos\lambda_n) + 4\lambda_n \sin\lambda_n(1 - \overline{C}_g + (Da/Sh))}{[\lambda_n \sin 2\lambda_n + 2\lambda_n^2]} \quad (26)$$

The concentrations are made dimensionless with respect to the inlet concentration ($C_{in}$) of oxygen and x and z are made dimensionless by L and H respectively. The numerical calculations were found to agree well with the analytical solution at Sh=1.0 and 0.7.

Bioreactor Oxygenation

The function and viability of hepatocytes within a bioreactor depend critically upon the availability of oxygen. In a reactor with oxygen impermeable surfaces, the flowrate or Peclet number is a primary way to control oxygenation. By introducing a membrane on the upper surface of the reactor, additional means become available of controlling oxygen transfer to the cells. The steady state oxygen gradient within a reactor having an internal membrane oxygenator is established via an interplay of Sherwood, Damkohler and Peclet numbers. The Reynolds number is always within laminar flow range (<10) owing to the small hydrodynamic height in the reactor, which also reduces the entrance length significantly. The range of Damkohler and Peclet numbers may be limited by scale-up or other transport considerations. Thus, the Sherwood number and gas phase oxygen partial pressure become important parameters controlling cell oxygenation (see Eqn. (23)).

The role of these two parameters is elucidated by assuming a Damkohler number of 0.11 (corresponding to rat hepatocytes, (Rotem et al., *Biotechnology and Bioengineering*, 40:1286 (1992)) for the numerical calculations. From a previous study of impermeable plate reactors, we found that cell surface oxygen was depleted when $$\left(\frac{L}{H}\right)\frac{1}{Pe} + \frac{1}{3} \geq \frac{1}{Da}. \quad (27)$$

Given a L/H value of 750, Peclet was chosen to be 3.3 and 33.3 to highlight the benefits of membrane oxygenation. Other important constants in the simulations were, $K_m$=6.664 nmol/mL (Rotem et al. supra) and $C_{in}$=183.26 nmol/mL.

Effect of Membrane Sherwood Number

Figure 29:
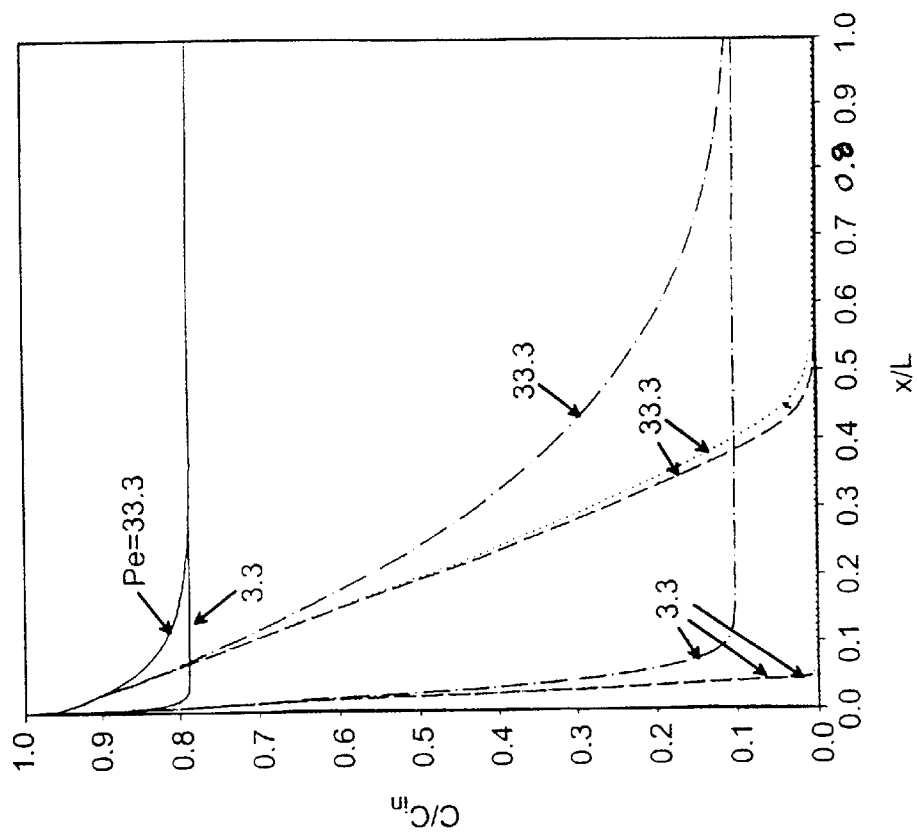
FIG. 29 is a graph of cell, surface oxygen concentration as a function of length along the reactor (gradients in the impermeable plate reactor, Da-0.11, are represented by dashed lines; gradients in the membrane reactor, Da=0.11 and $C_g=C_{in}$, are represented by dotted lines for Sh=0.01, dot-dashed lines for Sh=0.1, and solid lines for Sh=1.0).
Figure 28:
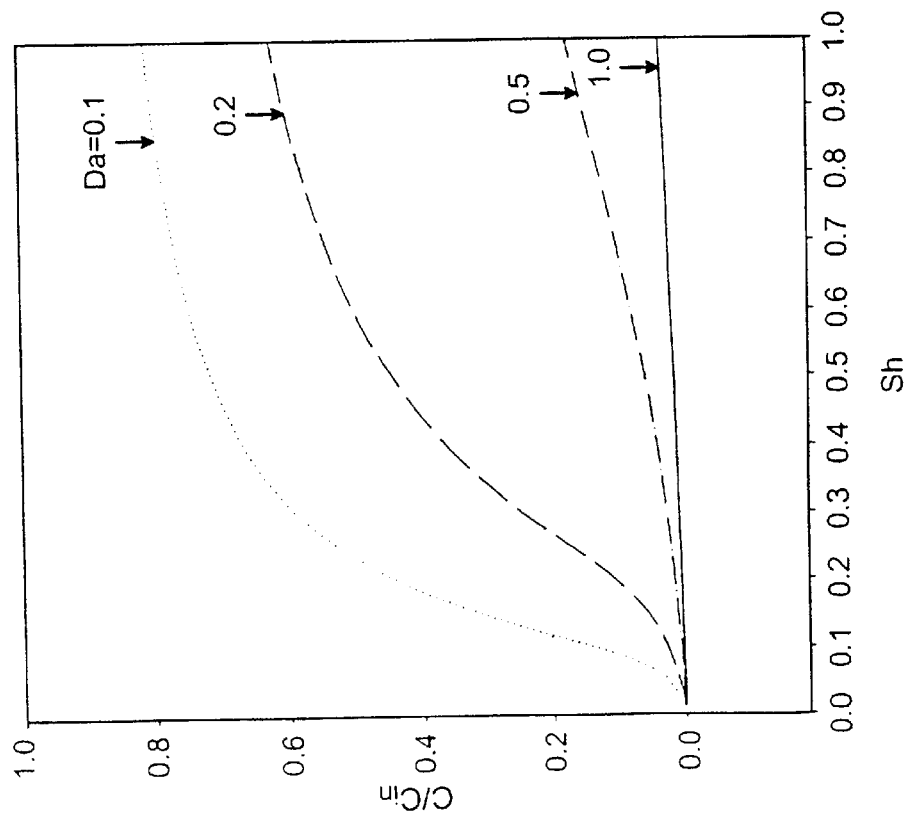
FIG. 28 is a graph of oxygen gradients on cell surfaces in a membrane reactor as function of the membrane Sherwood (Sh) number and Damnkohler (Da) number.

The Sherwood number is the ratio of mass transfer by permeation to mass transfer by diffusion of molecular oxygen. In the limit of very low Peclet numbers, the bioreactor behaves as a diffusion chamber for oxygen. In FIG. 28, cell surface oxygen tension (from Eqn. 24) increases with Sherwood number for all Da<1. Cell hypoxia (C<<$K_m$) occurs when: a) there is diffusion limitation (Da>1); or b) when permeability is very low (Sh<0.01). The effect of Sherwood number is further illustrated at finite Peclet numbers in FIG. 29. A comparison is made between reactors with and without a permeable surface. In the case of the reactor with impermeable surfaces, roughly 50% of the reactor is oxygen depleted at Pe=33.3 and the depletion increases to more than 90% at Pe=3.3. On the other hand, at Sherwood numbers Sh>0.1, the membrane reactor is well oxygenated throughout its length. It is only at very low Sherwood numbers (<0.01) that oxygen depletion occurs in the reactor. For a given Peclet number, oxygen gradients within the reactor can be regulated simply by changing the Sherwood number as discussed below. At low Peclet numbers (e.g., 3.3 and 33.3), the diffusion concentration (Eqn. 24) exists over a significant length of the reactor. The effect of flow (or Peclet number) is to increase cell surface oxygen beyond the diffusion concentration.

Effect of Gas Phase Oxygen Partial Pressure

Figure 31:
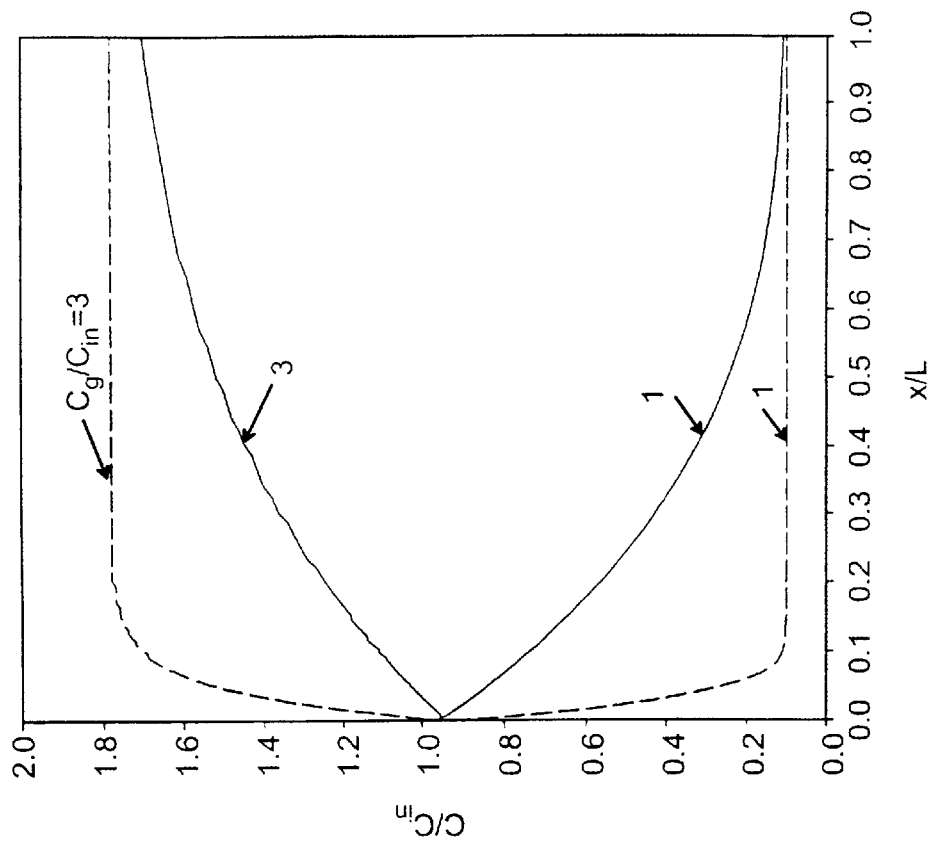
FIG. 31 is a graph of oxygen concentration profiles experienced by cells along the length of a membrane reactor, Da=0.11 and Sh=0.1, as the gas phase oxygen partial pressure changes (dashed lines represent Peclet(Pe)=3.3; solid lines represent Pe=33.3).
Figure 30:
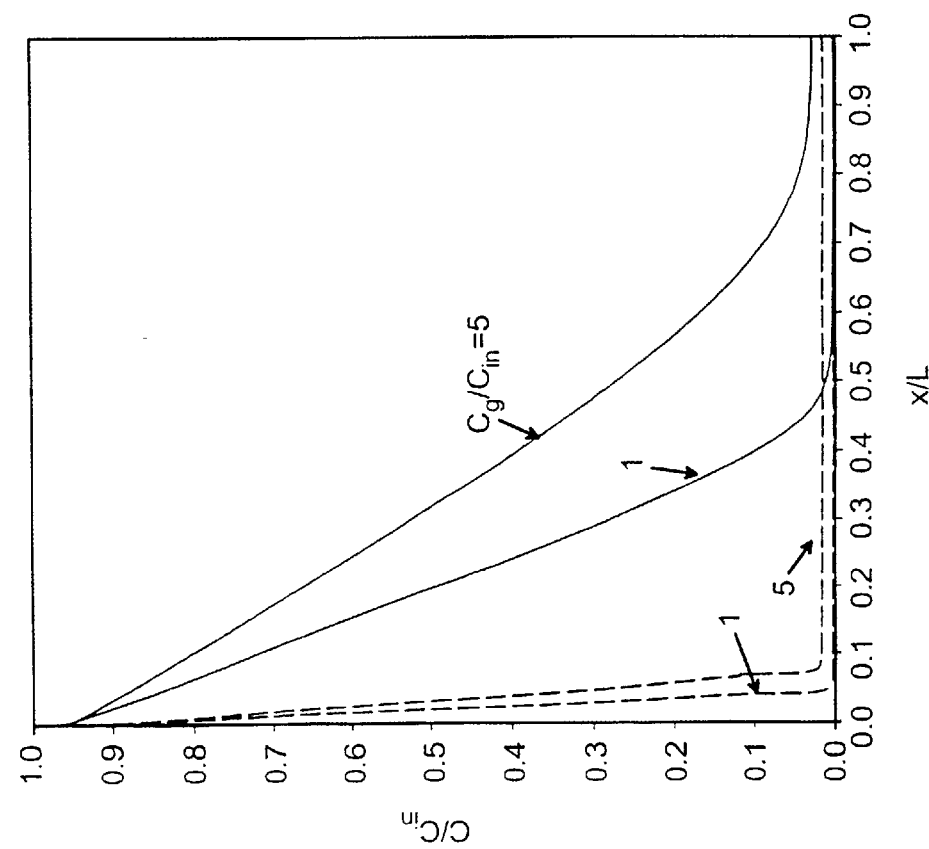
FIG. 30 is a graph of oxygen gradients experienced by cells along the length of a membrane reactor, Da=0.11-1 and Sh=0.01, as the gas phase oxygen partial pressure changes (dashed lines represent Pe=3.3; solid lines represent Pe=33.3).

The mass flux of oxygen into the reactor can also be enhanced by increasing the gas phase oxygen partial pressure (from Eqn.(23)). According to FIG. 30, at low Sherwood numbers (Sh<0.01), cells in the membrane reactor are hypoxic (C<<$K_m$) when gas phase oxygen pressure is low. Oxygen transfer to the cells can be increased in two ways. Firstly, by increasing the gas phase oxygen partial pressure and secondly, by increasing the Peclet number (see FIG. 31). This is also true at higher Sherwood numbers (Sh>0.1) and although there is no oxygen depletion in this case (see FIG. 31), it is possible to establish very high oxygen tensions within the reactor simply by increasing the oxygen partial pressure in the gas phase. Also, at low Peclet numbers, the diffusion concentration (Eqn. 24) is rapidly attained within the reactor. Thus, under conditions of fixed Sherwood and Peclet numbers, cell oxygenation can be controlled by changing the molar ratio of oxygen in the gas phase.

Under certain limiting conditions the membrane reactor may develop anoxic regions. When the cells consume oxygen with Michaelis-Menten kinetics, oxygen depletion occurs only for Da>1 and/or Sh<0.01 (FIG. 28). The analytical solution presented in Eqn. (25), assumes that the cells consume oxygen at a constant rate ($\overline{K}_m$=0). For flowrates at which Pe<<L/H, Eqn. (25) yields a simple criteria for the development of cell anoxia $$Da \geq \frac{Sh\overline{C}_g}{(1 + Sh)} \quad (28)$$

Our numerical calculations agreed well with the predictions of Eqn. (28) in the range 0.08<Sh<10 with $C_g$=$C_{in}$ (results not shown). For very high Sherwood numbers, Eqn

(28) becomes Da>1, which implies that anoxia occurs only when the transfer of oxygen to the cells is diffusion limited. At very low Sherwood numbers (Sh<0.01), Eqn. (25) predicts anoxia when Da≧Sh$\overline{C}_g$.

Oxygenation in Membrane Bioreactors

The effective transfer of oxygen to a monolayer of hepatocytes in reactor microchannels is vital for the proper functioning of a BAL device. Flowrate is the main parameter controlling cell oxygenation based on studies of parallel plate bioreactors. The results in the present study suggest additional ways to control oxygenation by using a membrane reactor. The two parameters that provide additional control are the membrane Sherwood number and the gas phase oxygen partial pressure. The Sherwood number may be changed by changing the effective permeability ($\sigma_e$) of the membrane, and the effective permeability can be varied by introducing a porosity factor, $p_f$ (such that $\sigma_e = p_f \sigma$; Sh=$\sigma_e$H/$D_z$).

Bioreactors having an impermeable plate (Sh=0) were shown to have no viable rat hepatocytes near the reactor outlet after 8 hours. Considering the dimensions and flowrate of the impermeable plate reactor, this occurs at Peclet number 33.3 (see FIG. 29). On the other hand, high cell viability was observed throughout a membrane reactor with a Sherwood number of 0.2. This may be explained with reference to Eqn (24) and FIG. 28 which indicate that minimum oxygen tension at the hepatocyte surface was roughly 61 mm Hg, well within the physiological range. Wall shear stresses corresponding to Pe<33.3 resulted in increased albumin and urea synthesis in the membrane based bioreactor. It has also been demonstrated that an impermeable plate reactor containing porcine hepatocytes is oxygen depleted at Pe=33.3, while high oxygen tensions were maintained in a membrane based reactor. The findings of these studies are in qualitative agreement with the model predictions presented herein.

For porcine or rat hepatocytes, the conditions under which the cells encounter hypoxia in the membrane bioreactor are at Da<0.25 (H=100μm). According to the diffusion solution (Eqn. (24)), the cells will not be hypoxic if inlet and gas phase oxygen tensions are 10% (of ambient) or more. If the inlet tension falls below 10% (Da will increase), adequate oxygenation can still be maintained by increasing the molar ratio of oxygen in the gas. Similarly, increasing the channel height will increase Da and Sh numbers. Hypoxia will occur when Da>1 or H>1000 μm. Such large channel heights are undesirable because of the associated high fluid volumes within the bioreactor. To maintain physiological oxygen tensions, the bioreactor is preferably operated with 50<H<100 μm, 75<$C_{in}$, $C_g$<100 mmHg.

The diffusion solution (Eqn. (24)) allows for a reactor to be optimized to maintain a minimum desirable oxygen tension. In principle, this means that the length of a reactor can be made arbitrarily large. However, in practice the growth of the diffusion boundary layer for certain cell secreted species as a function of flowrate and aspect ratio may create mass transfer inhomogeneties within the reactor (see Peng and Palsson, *Industrial & Engineering Chemistry Research*, 34:3239 (1995)). In light of this, the length of the bioreactor channels will also have to be optimized for maximum cellular function and viability. Moreover, high oxygen tensions within the reactor may result in oxygen-induced free radical toxicity.

The implications of these model predictions are best understood in the context of scale up to a BAL device for human applications. The adult human liver contains 250 billion hepatocytes. A BAL support device can contain roughly 25 billion cells or 10% of the total cell mass. At a cell seeding density of 1×10$^5$ cells/cm$^2$, roughly 200 (30 cm by 40 cm by 0.01 cm ) reactor modules can be operated in parallel. In each module, oxygen will be supplied to 120 million cells. To reduce large inlet lengths, each module can contain smaller interconnected channels where oxygen depletion is predicted to occur in the absence of membrane oxygenation. By using a suitable membrane (e.g., polyurethane) in conjunction with a perforated support plate whose porosity can be varied, we can effectively vary the membrane Sherwood number. This reactor configuration will provide enhanced control of oxygen gradients. If the incoming plasma has 10% oxygen tension and the same is maintained in the gas phase, the oxygen gradients within the reactor will be in the physiological range. Thus, by closely mimicking the in vivo oxygen microenvironment of hepatocytes, a BAL device may exhibit improved cellular function and provide adequate support to patients with compromised liver functions.

Example 11

In Vitro and In Vivo Evaluation of Porcine Hepatocyte Function in a Flat-Plate Bioreactor A flat-plate bioreactor containing an internal membrane oxygenator was used to evaluate cultured porcine hepatocyte viability and synthetic function in both in vitro and in vivo flow circuit models. Albumin produced by cultured porcine hepatocytes in the bioreactor was measured by an enzyme linked immunosorbent assay (ELISA) as a marker of liver-specific function in the samples.

Bioreactor Design

Figure 32:
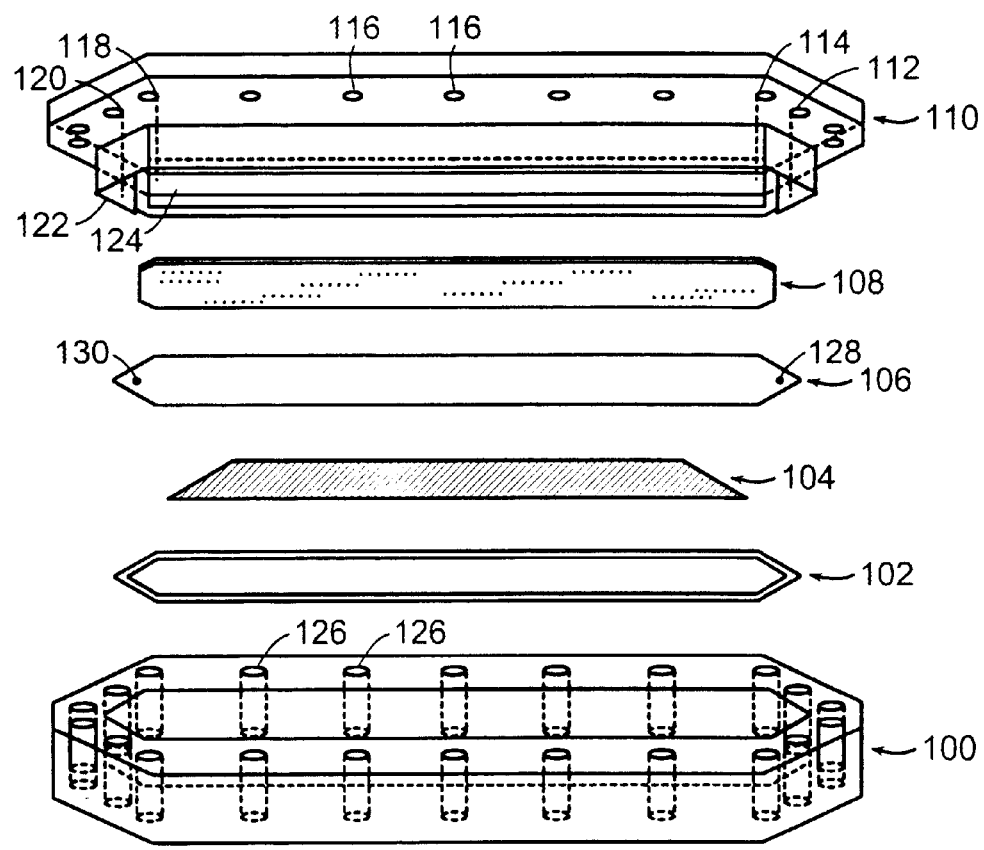
FIG. 32 is a schematic diagram of a flat plate bioreactor configuration containing an internal membrane oxygenator.

The flat-plate bioreactor configuration used in this investigation is shown in FIG. 32. The bioreactor was fabricated from polycarbonate (Laird Plastics, Rancho Dominguez, Calif.). The outside perimeter of the bottom half of the reactor was 2.54 cm thick and a compartment 1.90 cm deep was formed within this perimeter. The floor of this compartment served as the floor of the fluid compartment. Within the floor, an additional 0.076 cm inset was placed to accommodate a 7.62 cm×12.70 cm×0.076 cm soda-lime glass slide 104 (Erie Scientific, Portsmouth, N.H.), which served as the cell contact substrate. A through window in the polycarbonate allowed for viewing of the cells during static culture. The glass slide 104 was affixed to the bottom portion 100 of the reactor with a silicone sealant (734 RTV Sealant, Dow Corning, Midland, Mich.), so as to place the glass slide 104 flush with the floor of the bioreactor.

The cell-containing compartment of the reactor was formed by the juxtaposition of the top portion 110 of the reactor with the bottom portion 100. A seal was accomplished via a 0.076 cm thick gasket of silicone sheeting 102 (Applied Silicone, Ventura, Calif.) that was fixed in a groove machined 500 μm deep, surrounding the glass slide 104 as well as the triangles at either end (for flow development) with silicone sealant. Surrounding the gasket groove, along the walls of the bottom portion 100 of the bioreactor a lip was raised 100 μm off the bioreactor floor. This lip prevented the intrusion of the top portion 110 of the reactor below the level of the lip, thereby assuring that the cell-containing compartment did not go below 100 μm in height. Surrounding and adjacent to this lip was a 1.90 cm high wall that allowed the bottom portion 100 of the reactor to also serve as a culture dish. This wall had 22 evenly spaced through holes 126 threaded for 10-32 screws, which corresponded to clearance holes 116 along the perimeter of the top of the reactor.

The top portion 110 of the reactor was 2.54 cm thick, with the perimeter being 0.63 cm thick and having 22 clearance holes 116 for 10-32 threaded screws. Within the top, on the inside surface, there was a triangular area at each end in the long direction, in which were through holes 0.16 cm in diameter, which served as the inlet 112 and outlet 120 for media or plasma. On the outside surface the inlet 112 and outlet 120 through holes were enlarged for a length of 0.70 cm and threaded to fit 10-32 threaded Luer barbs (Small Parts Inc., Miami Lakes, Fla.). Between the two triangles on the inside surface there were 0.16 cm deep insets 122 to accommodate the membrane support 108. Within the boundaries defined by the area of the membrane support 108, the inside surface was machined a further 0.25 cm deep, with 0.25 cm×0.25 cm posts left at intervals to support the membrane support 108 and prevent it from bowing out into the gas compartment and causing an increase in the fluid channel height. Within this area at both long ends, through holes were machined to serve as the inlet 118 and outlet 114 to the gas compartment. On the outside surface these through holes 118 and 114 were enlarged, threaded and fitted with 10-32 Luer barbs in the same manner as the inlet 112 and outlet 120 for the media.

The membrane support 108 was a perforated aluminum plate 0.16 cm thick with 0.084 cm diameter holes spaced at 0.14 cm centers for an open area of 28% (Small Parts Inc.). The membrane support 108 was fixed into place at the perimeter of the support with silicone sealant, which also served to occlude the holes at the perimeter. When the membrane support 108 was in place, it was flush with the triangles at either end, thereby creating a flat surface. The oxygen permeable membrane 106 was then adhered to the membrane support 108 as well as to the triangles in one piece, serving to create a complete separation of the gas and fluid compartments. Holes in the membrane 128 and 130 were cut at the inlet 112 and outlet 120 for the fluid compartment. When ready for either in vitro or in vivo flow experiments the top portion 110 was fitted into the bottom portion 100 and secured with 22 2.54 cm long 10-32 threaded hex screws.

Hepatocyte Isolation and Culture

Porcine hepatocytes were isolated according to the methods described in Example 5 Type I collagen was prepared from adult female Lewis rat (Charles River Laboratories, Boston, Mass.) tail tendons (see Dunn et al. (1991) *Biotechnol. Prog.* 7:237–45). The bioreactor cell glass surface was coated with 25 ml of collagen coating solution and incubated at 37° C. for 1 hour. The collagen solution was then aspirated off and the surface was then washed twice with Earle's Balanced Salt Solution (Gibco BRL, Gaithersburg, Md.). The hepatocytes were suspended in culture medium ($5.0 \times 10^5$ cells/ml) and seeded into the bioreactor cell culture housing at a density of 15 million cells per bioreactor, in 30 ml of media per seeding. Two seedings were done separated by an hour. The cultured hepatocytes were maintained in an incubator set at 37° C. under a humidified gas mixture of 90% air/ 10% $CO_2$ overnight.

The following day, the media was aspirated off and replaced with 20 ml of fresh culture media. The cultured hepatocytes were maintained in an incubator at 37° C. under a humidified gas mixture of 90% air/ 10% $CO_2$. The media was collected daily and replaced with 20 ml of fresh culture medium. The collected samples were kept at 4° C. until quantitative analysis of albumin production.

Measurement of Porcine Albumin

Albumin, produced by porcine hepatocytes in the bioreactor, was measured by ELISA as a marker of liver-specific function in the samples. The primary antibody used in the ELISA was specific for porcine albumin. Media samples from the in vitro experiments were stored at 4° C. until the ELISA was performed. For the in vivo analysis, plasma was extracted from blood samples and was stored immediately at −80° C. until the ELISA was performed. The sensitivity of the ELISA was 3.12 $\mu$g/ml.

In Vitro Flow Experiments

On either the third or fourth day post isolation, the medium was aspirated from the bottom of the bioreactor and the cells were washed 3 times with 20 ml of fresh medium. The third wash was sampled for later testing for residual albumin content. 12–13 ml of the final wash was placed into the reservoir as the circulating medium. The top portion 110 of the bioreactor was then placed into position and secured with hex screws on the perimeter. The reservoir was then attached to the bioreactor medium inlet Luer barb and outlet Luer barb via #13 Masterflex silicone tubing (Masterflex L/S, Cole-Palmer Instrument Co., Vernon Hills, Ill.).

The in vitro flow experiments were performed in a humidified warm room at 37° C. The medium in the reservoir was then pumped through the flow circuit via digital variable-speed pump (Masterflex L/S) at 0.30 ml/min. Additional #13 tubing was attached to the Luer barbs at the inlet 118 and outlet 114 to the gas compartment and humidified gas composed of 10% $CO_2$, 21% $O_2$ and 69% $N_2$ was then passed through the gas compartment of the reactor in the countercurrent direction with respect to the medium flow. The end of the tubing at the outlet of the gas compartment was submerged in a small vial of water so that gas flow could be confirmed easily by the appearance of bubbles. Typically, 13 ml of media would be distributed as follows: 2 ml in the inlet, outlet and tubing; 6 ml in the reservoir and 5 ml in the flow channel of the reactor.

The flow experiment was continued for 3–4 days. Every 24 hours approximately 5 ml of medium was removed from the reservoir, sampled and replaced with fresh medium. Any evaporative losses, typically 0.5–1.0 ml per day, was also replaced to keep the reservoir at the same level as at the start of the in vitro flow experiment.

Figure 33:
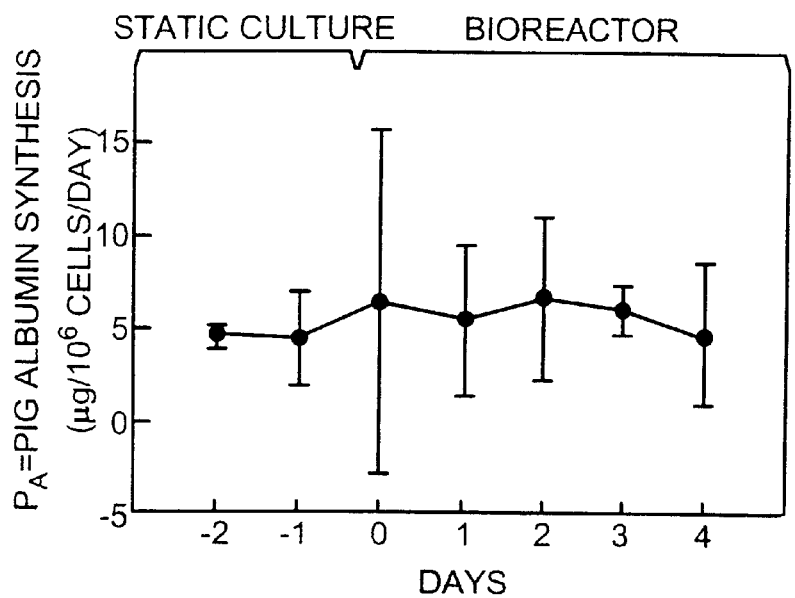
FIG. 33 is a graph of albumin production by porcine hepatocytes in a flat plate bioreactor in vitro.
Figure 34:
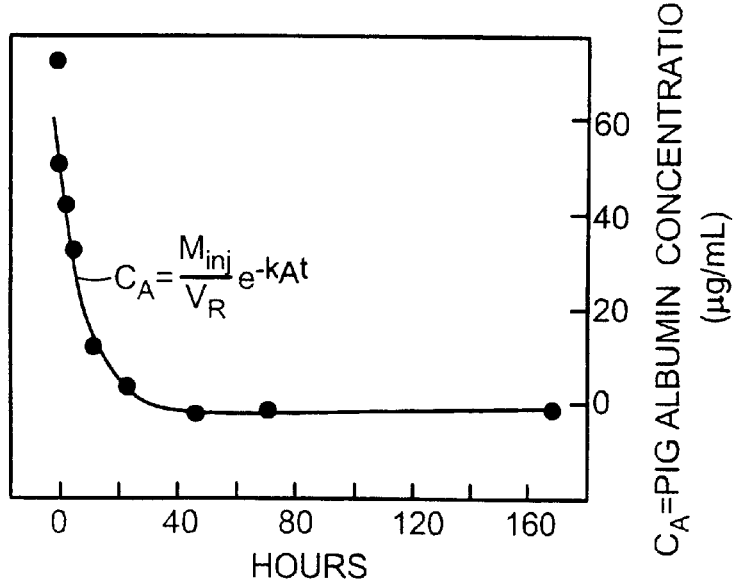
FIG. 34 is a graph of porcine albumin disappearance measured data points against a fitted regression curve.

Albumin production by porcine hepatocytes is widely accepted as an indicator of hepatic stability and adaptation within a culture environment. Albumin production from the hepatocytes in the bioreactor was shown to be maintained for up to 4 days under flow at a rate of 0.3 ml/min (FIG. 33). The daily average production of albumin was steady, between 4.35 and 6.41 $\mu$g/$10^6$ cells/day, for the entire duration of flow with an average of 5.45 $\mu$g/$10^6$ cells/day. Though albumin production was widely variable between reactors prior to the start of the flow experiment, resulting in wide standard deviation bars, the differences in albumin production between reactors narrowed under flow.

Experimental Animals

Male Sprague-Dawley rats (Charles River Laboratories), weighing 200–300 g, were used for this study. All animals were acclimated to the animal research laboratory for 5 days prior to experiments and were maintained in a light-controlled room (12-hour light-dark cycle) at an ambient temperature of 25° C. with chow diet and water ad libitum.

Surgical Procedures

Cannulation of the carotid artery and the jugular vein was performed as previously described (Stefanovich et al. (1996) *J. Surg. Res.* 66:57–63). The rats were anesthetized with intraperitoneal injections of ketamine (Abbott Laboratories, N. Chicago, Ill.) and xylazine (Phoenix Pharmaceutical Inc., St. Joseph, Mo.) at 110 and 0.4 mg/kg, respectively. The shaven neck of the animal was disinfected with iodine prep solution. An incision just above the clavicle was made and then the right jugular vein and the left carotid artery were free and exposed. A small incision was made in the skin between the scapulae and two 40 cm lengths of PE 50 polyethylene tubing (Becton Dickinson & Co., Sparks, Md.) were tunneled subcutaneously on either side of the neck and externalized through the dorsal incision. The lines were then passed through a flexible, hollow tether, fitted with 23 gauge luer stub adapters (Becton Dickinson & Co.) and three-way stopcocks (Cole-Parmer Instrument Co.) at one end, and filled with heparinized (20 U/ml) saline solution. The jugular vein was cannulated with a 2 cm silicone tubing (VWR Scientific Products, Boston, Mass.) extension of the polyethylene tubing to prevent damage to the vessel. The carotid artery was cannulated to a depth of 2 cm. After wound closure, the tether was attached to a fitted rat jacket (Lomir Biomedical Inc., Malone, N.Y.). The animal was transferred into a metabolism cage (Fisher Scientific, Pittsburgh, Pa.), and the tether and associated three-way stopcocks were passed through the cover. This arrangement allowed the animal complete freedom of movement within the cage and access to food and water ad libitum. To prevent blood clotting, heparinized (20 U/ml) saline solution was continuously infused at a rate of 0.2 ml/h through the artery line by a syringe infusion pump (Fisher Scientific) until the extracorporeal perfusion experiments were initiated.

The surgical procedures and extracorporeal perfusion were well tolerated by the animal as demonstrated by behavior such as normal food and water intake observed after surgery as well as during the perfusion. Initial technical difficulties such as twisting of the catheters, bleeding from the wound, clotting circuits and hemolysis during plasmapheresis were avoided by the following: careful observation, beginning perfusions 20–24 hours after vessel cannulation, and the continuous administration of heparin throughout the duration of extracorporeal perfusion.

Porcine Albumin Disappearance in the Rat

To verify albumin biokinetics in the animal model, a rat was injected with 0.5 ml of porcine albumin (Sigma Chemical Co., St. Louis, Mo.) (10 mg/ml diluted with saline) into the penis vein. Cannulation of the right jugular vein for blood sampling was performed in a similar manner as described previously, 20–24 hours prior to porcine albumin injection. Blood samples (0.25 ml each) were collected at time (just before the injection), then 15 minutes, followed by 1, 3, 6, 12, 24, 48, 72 and 168 hours following injection. Heparinized saline solution (10 U/ml) was continuously infused at a rate of 0.2 ml/h through the venous access line by syringe infusion pump to prevent extracorporeal line thrombosis. At the completion of the experiment, the animal was sacrificed by intravenous administration of pentobarbital (Abbott Laboratories) at 50 mg/body.

Figure 36:
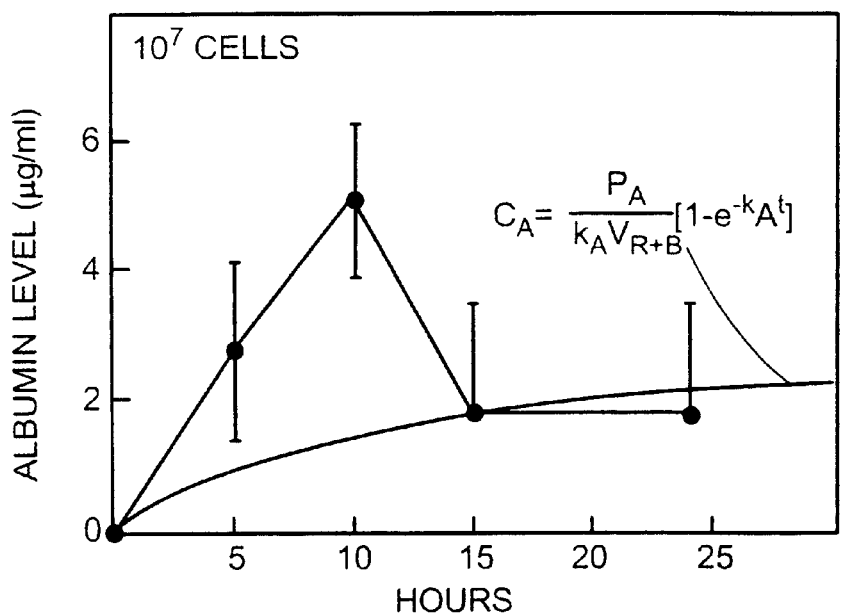
FIG. 36 is a graph of (1) porcine albumin concentration in a rat connected to a flat plate bioreactor containing porcine hepatocytes; and (2) a predicted concentration curve based upon the data from FIG. 34.

Pharmacokinetics of porcine albumin in the rat model is shown in FIG. 36, which displays the measured data simultaneously with the fitted curve of the pharmocokinetic model for porcine albumin in this model. The model fitted the data with a correlation coefficient of 0.99. Measured albumin levels in rat plasma reached a peak at 15 minutes, and then decreased following administration. From 48 to 168 hours, its concentration was below the lower limit of detection (3.12 μm/ml) in rat plasma samples. The decay constant, $k_A$, is calculated to be 0.1329 hr$^{-1}$. The volume of the rat vasculature, $V_R$, is calculated from this information to be 14.1 ml.

In Vivo Extracorporeal Perfusion Experiments

On day 3 or 4 after isolation of the hepatocytes, the medium was aspirated and the top of the bioreactor was assembled with the bottom of the bioreactor. The bioreactor was then primed with 6 ml of sterile, heparinized Sprague-Dawley rat plasma (Rockland, Gilbertsville, Pa.), which was filtered immediately prior to its use.

Figure 35:
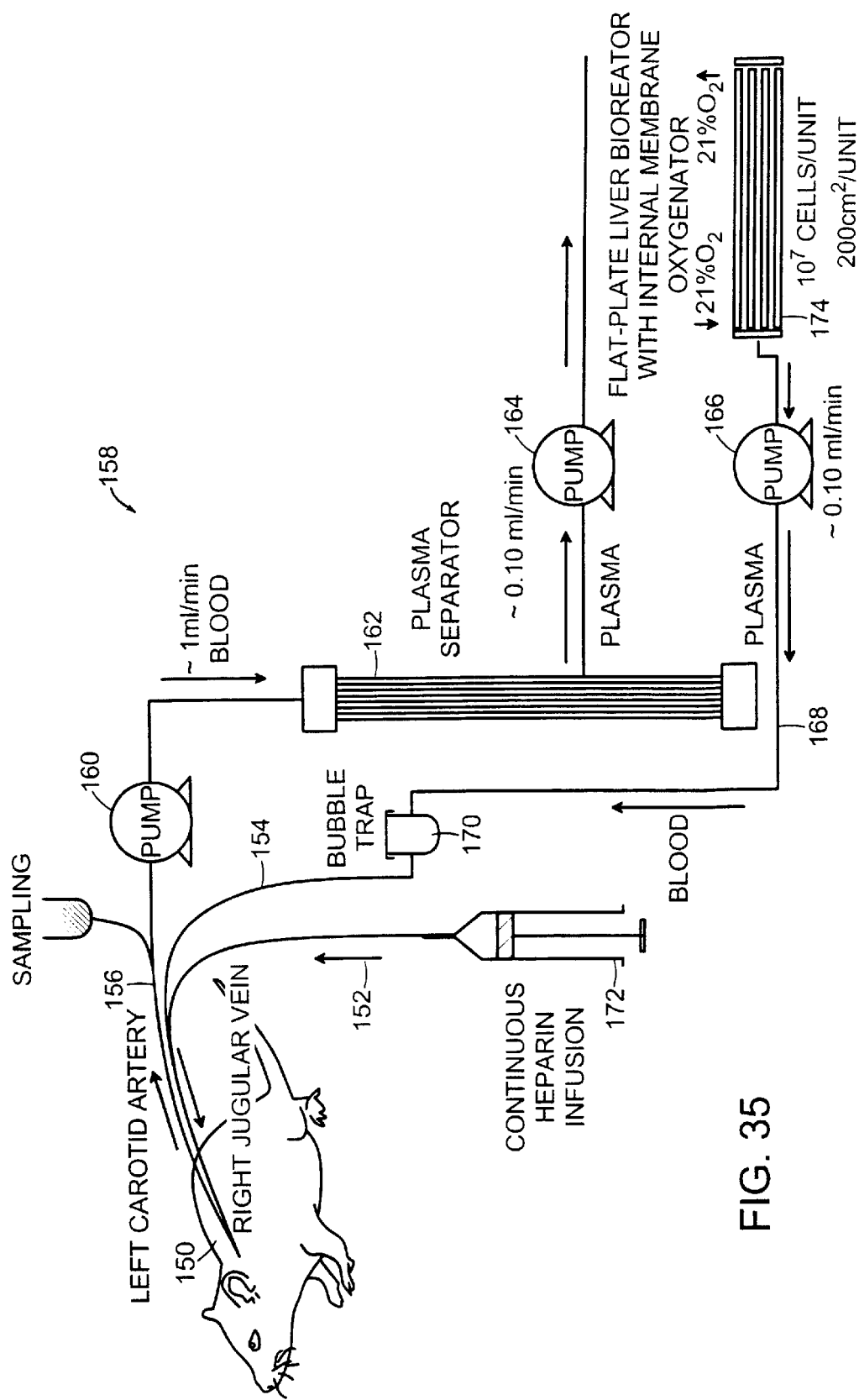
FIG. 35 is a schematic diagram of an extracorporeal perfusion system in a rat.

The extracorporeal perfusion system (FIG. 35) was also primed with the same plasma. The rat 150 was administered 100 U heparin 152 (0.1 ml) systemically through the venous line 154 five minutes prior to the start of perfusion. The arterial 156 and venous 154 lines were subsequently connected to the extracorporeal circuit 158. Arterial blood was pumped at 0.8–1.2 ml/min through #13 Masterflex silicone tubing by a digital variable-speed peristaltic pump 160 (Masterflex L/S) drive. A plasma separator 162 (MicroKros™, membrane material: mixed esters of cellulose, membrane pore size: 0.2 μm, membrane surface: 16 cm$^2$) (Spectrum Laboratories Inc., Laguna Hills, Calif.) was placed after the pump 160. Separated plasma was pumped though the bioreactor 174 by means of second 164 and third 166 peristaltic pump at a flow rate of 0.1 ml/min. The separated plasma and remaining blood components were reunited 168 before entering a bubble trap 170, which was constructed by adding a 0.5 ml microcentrifuge tube and two connectors (Small Parts Inc.) with silicone sealant (Dow Corning). Reconstituted blood returned to the animal through the venous cannula. During the perfusion, heparin (43.5 U/ml) with 5% dextrose solution was administered 152 continuously through the venous line 154 at a rate of 0.2 ml/h, via a syringe infusion pump 172. In this configuration, the dead volume of the entire perfusion system 158 was 10 ml, of which 6 ml was accounted for by the bioreactor 174.

For extracorporeal perfusion experiments, the animals were cannulated and allowed to recover from anesthesia and surgery for 20–24 hours. The animals were then attached to the bioreactor with (n=3) or without (n=4) porcine hepatocytes 30 minutes following commencement of extracorporeal perfusion, and remained connected for 24 hours. The plasma separator was changed around 12 hours following the initiation of perfusion. Blood samples (0.8 ml/each) were collected from the arterial line at 0, 5, 10, 15 and 24 hours following attachment to the bioreactor. An equivalent volume of sterile heparinized rat plasma was replaced during each sampling. At the completion of experiments, animals were sacrificed via intravenous administration of pentobarbital at 50 mg/body.

Mathematical Modeling of Porcine Albumin Kinetics In Vivo

A simple first-order decay model was developed to follow the kinetics of porcine albumin disappearance in a rat.

$$p_A$$

$$V_R \frac{dc_A}{dt} = M_{B,A}\delta(t) - k_A V_R c_A$$

$$c_A = \left(\frac{M_{B,A}}{V_R}\right)e^{-k_A t}$$

Where $V_R$=volume of rat vasculature (ml)

$k_A$=decay constant of albumin (hr$^{-1}$)

$M_{B,A}$=bolus albumin mass (μg)

CA=concentration of porcine albumin in the rat (μg/ml)

t=time (hr)

=porcine albumin production rate (/hr)

$V_{R+C}$=volume or rat vasculature and reactor circuit (ml)

The value of the decay constant, $k_A$, was estimated by fitting the model to the porcine albumin disappearance data using the method of least squares. The amount of porcine albumin in the animal vasculature, when the animal was connected to the bioreactor, was predicted using $k_A$ and assuming constant rate of production of porcine albumin by the bioreactor (5.45 µg/10⁶ cells/day) during the duration of the in vivo experiment.

Porcine Albumin Measurement in the In Vivo Extracorporeal Perfusion System

Porcine albumin was below the lower limit of detection in rat plasma samples at any time point where the bioreactor was functioning without porcine hepatocytes. Porcine albumin was detected at 10 hours in case 1 and was 6.99 µg/ml. In case 2, it was detected at 5 hours (3.88 µg/ml) and 10 hours (3.19 µg/ml). In case 3, it was detected in all samples taken, 3.76 µg/ml at 5 hours, 5.02 µg/ml at 10 hours, 5.32 µg/ml at 15 hours, and 4.72 µg/ml at 24 hours. FIG. 36 shows the average of the measured data points with the model's prediction of the concentration of porcine albumin in the rat vasculature. Two curves are shown: the first was generated using the average porcine albumin production (5.45 µg/10⁶ cells/day); and the second was generated using the maximum observed in vitro output (27.3 µg/10⁶ cells/day) of the bioreactor. They predict an initial increase in the level of porcine albumin in the animal followed by a plateau level around 24 hrs, at approximately 0.82 µg/ml for the first case and 4.12 µg/ml for the second case.

For the initial testing, the duration of perfusion for the experimental in vivo model was chosen to be 24 hours. This study demonstrated that porcine albumin in rat plasma samples was detected from 5 to 24 hours while attached to the BAL extracorporeal perfusion system with porcine hepatocytes.

Pharmacokinetics of porcine albumin in the rat was demonstrated and modeled in this study, and $k_A$ calculated from the data. Using this model we have predicted the concentration of porcine albumin in the circuit using both our average albumin production rate, as well as our maximum observed albumin production rate of 27.3 µg/10⁶ cells/day. Both the measured albumin concentrations in the in vivo circuit and the predicted concentrations are graphed together in FIG. 36, which demonstrates that the measured data is initially higher than predicted values, but then fall within the range of the two predicted curves. The initial high measured values at hours 5 and 10 may be due to rapid release of albumin from the hepatocytes. This may be due to cell death and lysis, which would allow a rapid release of intracellular albumin. Subsequent measured data points at hours 15 and 24 falls between the two predicted curves suggesting that the albumin production rate of the hepatocytes in the in vivo circuit is higher than the measured average in the in vitro experiments of this study.

Induction of Fulminant Hepatic Failure

D-galactosamine (GalN) (Sigma Chemical Co, St. Louis, Mo.) was freshly dissolved in 0.5 ml of physiological saline and adjusted to pH 6.8 with 1N NaOH. To examine the survival rates of rats following injection, GalN was twice administered at a 12 hour interval at a dose 1.2 g/kg to induce fulminant hepatic failure. The animals were observed every 12 hours for 7 days after the GalN injections and their survival was measured. The animals were attached to a BAL (with or without hepatocytes) 12 hours after the seconf GalN injection. The animals were connected to the BAL for a 10 hour period. Control animals had an equivalent volume of saline injected intraperitoneally. After injection, the rats had free access to food and water until they were sacrificed. Anesthesia was maintained with inhalation of halothane (Ayerst Laboratories Inc., Philadelphia, Pa.).

Figure 37:
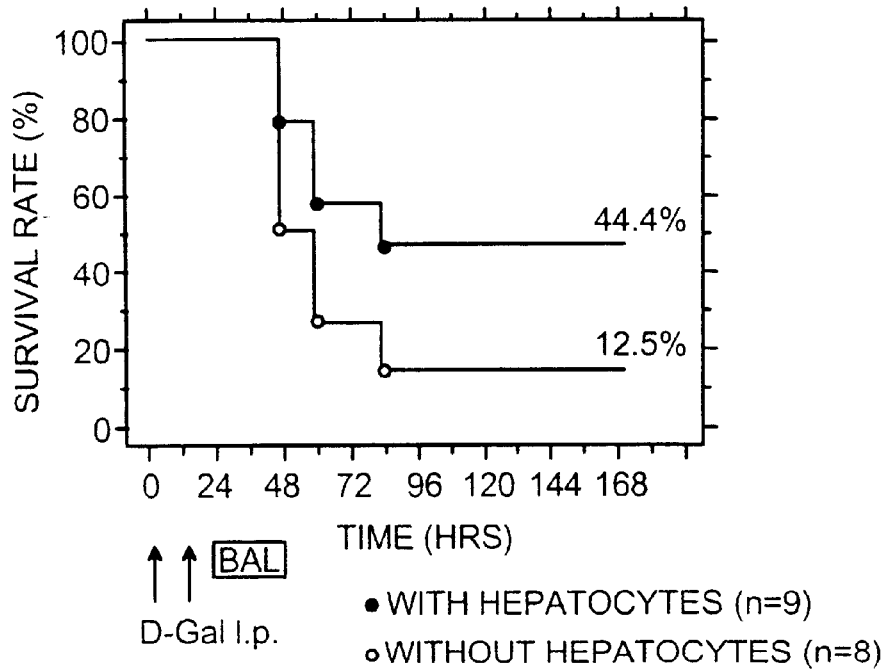
FIG. 37 is a graph of one week survival rates of rats following hepatic failure induced by D-galactosamine injections.

FIG. 37 shows the survival rate of GalN-intoxicated rats treated with or without porcine hepatocytes of the bioreactor. The survival rates at day 7 after the first injection of GalN are 44.4% with hepatocytes and 12.5% without hepatocytes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A flow-through cell culturing device comprising
a housing with an inlet and an outlet;
a first plate arranged within the housing; and
a second plate arranged within the housing substantially in parallel with the first plate to create a chamber therebetween having a height of between about 25 and 500 microns, wherein the chamber has a fluid entry and a fluid exit positioned such that fluid entering the housing through the inlet flows through the fluid entry of the chamber, flows through the chamber, exits the chamber through the fluid exit, and flows out of the housing through the outlet.

2. A device of claim 1, further comprising a first manifold controlling the flow of liquid from the housing inlet directly to the fluid entry of the chamber; and
a second manifold controlling the flow of liquid from the fluid exit of the chamber to the housing outlet.

3. A device of claim 1, further comprising third through tenth plates, all arranged within the housing substantially in parallel, stacked one on top of the other.

4. A device of claim 3, wherein each plate has a hole which serves as a fluid entry for the chamber below the plate, and as a second fluid exit from the chamber above the plate.

5. A device of claim 3, further comprising eleventh through twentieth plates, all arranged within the housing in parallel, stacked one on top of the other.

6. The device of claim 1, further comprising spacer elements that maintain the first and second plates at a uniform distance of 50 to 100 microns.

7. The device of claim 6, wherein each plate is associated with at least three spacer elements located at three points in a plane on the plate, and wherein all elements have the same height.

8. The device of claim 6, wherein the spacer elements are formed from the same material as the plates.

9. The device of claim 6, wherein the spacer elements are formed from a different material than the plates.

10. The device of claim 6, wherein the spacer elements comprise polymethylmethacrylate (PMMA), UV-cured acrylate adhesives, visible light curable adhesives, or polyurethane.

11. The device of claim 1, wherein the chamber height is 100 microns.

12. The device of claim 1, wherein the plates comprise glass, polymethylmethacrylate, or polycarbonate.

13. The device of claim 1, wherein the housing is cylindrical and the plates are circular disks.

14. The device of claim 1, wherein the total dead volume of the device is 250 to 2000 ml.

15. The device of claim 1, further comprising a cell seeded onto a plate.

16. The device of claim 15, wherein the cell is a hepatocyte.

17. The device of claim 15, wherein the cell is preserved.

18. The device of claim 1, wherein the chamber has a height of between 50 to 400 microns.

19. The device of claim 18, wherein the chamber has a height of between 50 to 200 microns.

20. The device of claim 19, wherein the chamber has a height of between 50 to 100 microns.

21. A liver assist system comprising
- a flow-through cell culturing device of claim 1;
- a first conduit for conducting liquid from a patient to the housing inlet;
- a second conduit for conducting plasma from the cell culturing device to the patient; and
- a pump for moving liquid through the conduits and cell culturing device.

22. The system of claim 21, further comprising a plasma separator to remove blood cells from whole blood to provide plasma that is passed through the cell culturing device.

23. The system of claim 21, further comprising a bubble trap, to remove bubbles from the plasma in the first conduit prior to entering the cell culturing device.

24. A method of filtering a bodily fluid, the method comprising
- seeding a cell culturing device of claim 1 with hepatocytes;
- introducing the bodily fluid into the inlet of the device; and
- allowing the bodily fluid to flow through the device and exit through the outlet, thereby filtering the bodily fluid.

25. The method of claim 24, further comprising seeding the device with fibroblasts.

26. The method of claim 24, wherein the device is seeded with 2 to 25 billion hepatocytes.

27. The method of claim 24, wherein the device is seeded with porcine, human, bovine, ovine, equine, or murine hepatocytes.

28. The method of claim 24, wherein the device is seeded with human hepatocytes.

29. The method of claim 24, wherein the bodily fluid is introduced into the inlet at a flow rate of 0.05 to 20 ml/minute.

30. The method of claim 24, further comprising passing the bodily fluid through a filter prior to introducing the bodily fluid into the inlet of the device.

31. The method of claim 24, wherein the bodily fluid is blood plasma.

32. A flow-through cell culturing device comprising
- a housing with an inlet and an outlet;
- a first plate arranged within the housing;
- a second plate arranged within the housing substantially in parallel with the first plate to create a chamber therebetween; and
- a gas-permeable, liquid-impermeable membrane arranged between the first and second plates to create first and second compartments within the chamber, the first compartment having a height of about 5 microns to 5.0 millimeters, and the second compartment having a height of between about 25 and 500 microns, wherein the first compartment has a gas entry and a gas exit, and the second compartment has a liquid entry and a liquid exit positioned such that liquid entering the housing through the inlet flows through the liquid entry of the second compartment, flows through the second compartment, exits the second compartment through the liquid exit, and flows out of the housing through the outlet, and wherein the first compartment and the second compartment are not in liquid communication.

33. The device of claim 32, wherein the gas-permeable, liquid-impermeable membrane comprises polyurethane, polyolefin, polyethylene, polypropylene, polyvinylidene fluoride, polystyrene, nylon, silicone rubber, or mixtures or copolymers thereof.

34. The device of claim 32, further comprising a substrate to support the membrane.

35. The device of claim 32, wherein the height of the second compartment is 50 to 100 microns.

36. The device of claim 32, further comprising additional plates and membranes arranged in a stack of alternating plates and membranes.

37. The device of claim 32, wherein the height of the first and second compartments is maintained by spacer elements.

38. A modular device comprising a plurality of units, a fluid inlet conduit, and a fluid outlet conduit, each unit comprising
- a plate; and
- a gas-permeable, liquid-impermeable membrane arranged substantially in parallel with the plate and connected to the plate by an exterior wall to create a chamber therebetween having a height of between about 25 and 500 microns, wherein the chamber has a fluid entry connected to the fluid inlet conduit and a fluid exit connected to the fluid outlet conduit and positioned such that fluid entering the chamber flows through the chamber, exits the chamber through the fluid exit, and flows out of the modular device through the outlet.

39. The modular device of claim 38, further comprising a substrate to support the gas-permeable, liquid-impermeable membrane.

40. The device of claim 38, wherein the gas-permeable, liquid-impermeable membrane comprises polyurethane, polyolefin, polyethylene, polypropylene, polyvinylidene fluoride, polystyrene, nylon, silicone rubber, or mixtures or copolymers thereof.

41. The modular device of claim 38, wherein the device is enclosed in a sealed container, the container having a gas entry and a gas exit.

42. The device of claim 38, wherein the fluid inlet conduit and fluid outlet conduits comprise a plurality of valves adapted for connection to individual units.

* * * * *